(12) United States Patent
Koop et al.

(10) Patent No.: US 7,371,923 B2
(45) Date of Patent: May 13, 2008

(54) PROCESS OF GENERATING TRANSPLASTOMIC PLANTS OR PLANT CELLS DEVOID OF A SELECTION MARKER

(75) Inventors: Hans-Ulrich Koop, München (DE); Stefan Mühlbauer, Freising (DE); Sebastian Klaus, Gräfelfing (DE); Christian Eibl, Ismaning (DE); Fong-Chin Huang, Taipei (TW); Timothy J. Golds, Freising (DE)

(73) Assignee: Icon Genetics AG, Munich (DE)

( * ) Notice: Subject to any disclaimer, the term of this patent is extended or adjusted under 35 U.S.C. 154(b) by 106 days.

(21) Appl. No.: 10/482,549

(22) PCT Filed: Apr. 30, 2002

(86) PCT No.: PCT/EP02/04777

§ 371 (c)(1),
(2), (4) Date: Aug. 19, 2004

(87) PCT Pub. No.: WO03/004658

PCT Pub. Date: Jan. 16, 2003

(65) Prior Publication Data

US 2005/0015829 A1    Jan. 20, 2005

(30) Foreign Application Priority Data

Jul. 6, 2001    (DE)    ............................... 101 32 780

(51) Int. Cl.
*C12N 15/82*    (2006.01)

(52) U.S. Cl. .................................... 800/278; 435/320.1

(58) Field of Classification Search ..................... None
See application file for complete search history.

(56) References Cited

U.S. PATENT DOCUMENTS

| | | | |
|---|---|---|---|
| 5,139,812 A | 8/1992 | Lebacq | |
| 5,474,925 A | 12/1995 | Maliyakal et al. | |
| 5,576,198 A | 11/1996 | McBride et al. | |
| 5,627,059 A | 5/1997 | Capecchi et al. | |
| 5,670,623 A | 9/1997 | Shoseyov et al. | |
| 5,723,765 A | 3/1998 | Oliver et al. | |
| 5,877,402 A | 3/1999 | Maliga et al. | |
| 6,100,448 A | 8/2000 | Thompson et al. | |
| 6,147,278 A | 11/2000 | Rogers et al. | |
| 6,174,700 B1 | 1/2001 | Haynes et al. | |
| 6,300,545 B1 | 10/2001 | Baszczynski et al. | |
| 6,331,416 B1 | 12/2001 | Shani et al. | |
| 6,331,661 B1 | 12/2001 | Baszczynski et al. | |
| 6,781,033 B2* | 8/2004 | Staub et al. ................. | 800/278 |
| 2003/0188337 A1* | 10/2003 | Day et al. .................... | 800/279 |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |
| 2005/0014150 A1 | 1/2005 | Atabekov et al. | |
| 2005/0015829 A1 | 1/2005 | Koop et al. | |
| 2005/0015830 A1 | 1/2005 | Dorokhov et al. | |
| 2005/0059004 A1 | 3/2005 | Atabekov et al. | |
| 2005/0066384 A1 | 3/2005 | Klimyuck et al. | |
| 2005/0091706 A1 | 4/2005 | Klimyuck et al. | |

FOREIGN PATENT DOCUMENTS

| | | |
|---|---|---|
| EP | 0270 248 | 6/1988 |
| EP | 1 045 037 | 10/2000 |
| WO | WO 87/00551 | 1/1987 |
| WO | WO 94/16089 | 7/1994 |
| WO | WO 95/34668 | 12/1995 |
| WO | WO 96/17954 | 6/1996 |
| WO | WO 98/09505 | 3/1998 |
| WO | WO 98/44097 | 10/1998 |
| WO | WO 98/54342 | 12/1998 |
| WO | WO 99/25821 | 5/1999 |

(Continued)

OTHER PUBLICATIONS

El-Sheekh, 2000, Folia Microbiol. 45:496-504.*
Mühlbauer et al, 2002, Plant J. 32:175-184.*
Albert et al. (1995) "Site-specific integration of DNA into wild-type and mutant lox sites placed in the plant genome" The Plant Journal 7:649-659.
Allison et al., "Deletion of rpoB Reveals a Second Distinct Transcription System in Plastids of Higher Plants," The EMBO Journal, 15:11 2802-2809 (1996).
Altschul et al. "Basic Local Alignment Search Tool," J. Mol. Biol., 215:403-410 (1990).

(Continued)

*Primary Examiner*—Anne Kubelik
(74) *Attorney, Agent, or Firm*—Myers Bigel Sibley & Sajovec, P.A.

(57) ABSTRACT

A process of generating transgenic plants or plant cells transformed on their plastome and being devoid of a selection marker, comprising the following steps: (a) transforming plastids of a plant or plant cell with a DNA comprising: (i) a nucleotide sequence conferring replication of said DNA in a plant cell, (ii) at least one sequence of interest, (iii) sequences flanking said at least one sequence of interest necessary for stable integration of said at least one sequence of interest into the plastid genome, and (iv) a selection marker outside of said sequences flanking said sequence(s) of interest; (b) allowing integration of said at least one sequence of interest into the plastome in the presence of selective pressure; (c) allowing loss of said selection marker sequence by releasing selective pressure; and (d) recovering cells and/or plants being genetically transformed on their plastomes and being devoid of said selection marker.

14 Claims, 17 Drawing Sheets

FOREIGN PATENT DOCUMENTS

| | | |
|---|---|---|
| WO | WO 99/25855 | 5/1999 |
| WO | WO 99/36516 | 7/1999 |
| WO | WO 01/11020 | 2/2000 |
| WO | WO 00/17365 | 3/2000 |
| WO | WO 00/20611 | 4/2000 |
| WO | WO 00/32799 | 6/2000 |
| WO | WO 00/68391 | 11/2000 |
| WO | WO 00/68431 | 11/2000 |
| WO | WO 00/70019 | 11/2000 |
| WO | WO 00/77174 | 12/2000 |
| WO | WO 00/77175 | 12/2000 |
| WO | WO 00/78985 | 12/2000 |
| WO | WO 01/59138 | 8/2001 |
| WO | WO 01/81600 | 11/2001 |
| WO | WO 02/12522 | 2/2002 |
| WO | WO 02/29068 | 4/2002 |
| WO | WO 02/46438 | 6/2002 |
| WO | WO 02/46440 | 6/2002 |
| WO | WO 02/055651 | 7/2002 |
| WO | WO 02/057466 | 7/2002 |
| WO | WO 02/068664 | 9/2002 |
| WO | WO 02/077246 | 10/2002 |
| WO | WO 02/079481 | 10/2002 |
| WO | WO 02/088369 | 11/2002 |
| WO | WO 02/101060 | 12/2002 |
| WO | WO 03/001900 | 1/2003 |
| WO | WO 03/004658 | 1/2003 |
| WO | WO 03/020927 | 3/2003 |
| WO | WO 03/020928 | 3/2003 |
| WO | WO 03/020938 | 3/2003 |

OTHER PUBLICATIONS

Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.

Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.

Bergamini et al. "Picornavirus IRESes and the Poly(A) tail Jointly Promote Cap-Independent Translation in a Mammalian Cell-free System," RNA, 6:1781-1790 (2000).

Bogorad, Lawrence, "Engineering Chloroplasts: an Alternative Site for Foreign Genes, Proteins, Reactions and Products," TIBTECH, 18:257-263 (Jun. 2000).

Bouchez et al. (1993) "A binary vector based on Basta resistance for in planta transformation of Arabidopsis thaliana" C. R. Acad. Sci. Paris, Science de la vie 316:1188-1193.

Boynton et al., "Chloroplast Transformation in Chlamydomonas with High Velocity Microprojectiles," Science, 240:1534-1538 (1988).

Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present In Linked Multiple Copies Greatly Enhances IRES Activity," PNAS, 97(4):1536-1541 (Feb. 15, 2000).

Clelland et al. (1999) "Hiding Messages in DNA Microdots," Nature 399:533-534.

Coutts et al. "Development of Geminivirus-based Gene Vectors for Dicotyledonous Plants" Australian Journal of Plant Physiology 17:365-375 (1990).

Dale et al. "Intra- and intermolecular site-specific recombination in plant cells mediated by bacteriophage P1 recombinase" Gene 91:79-85 (1990).

Dale et al. "Mutations in the CRE/LOX Recombination Site Enhance the Stability of Recombination Products: Applications for Gene Targeting in Plants" Journal of Cellular Biochemistry 50 (S16S):206 (1992).

Daniell, "New Tools for Chloroplast Genetic Engineering," Nature Biotechnology, 17:855-856 (Sep. 1999).

De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).

Domingo et al. (1999) "Identification of a novel peptide motif that mediates cross-linking of proteins to cell walls" The Plant Journal 20:563-570.

Dorokhov et al. "Polypurine (A)-Rich Sequences Promote Cross-Kingdom Conservation of Internal Ribosome Entry" PNAS 99(8):5301-5306 (Apr. 16, 2002).

Drescher et al., "The Two Largest Chloroplast Genome-Encoded Open Reading Frames of Higher Plants are Essential Genes," The Plant Journal, 22(2):97-104 (2000).

El-Sheekh, M.M. (2000) "Stable Chloroplast Transformation in *Chlamydomonas reinhardtii* using Microprojectile Bombardment" Folia Microbiol. 45(6) 496-504.

Gatz et al. (1991) "Regulation of a modified CaMV 35S promoter by the Tn10-encoded Tet repressor in transgenic tobacco" Mol. Gen. Genet. 227:229-237.

Hager at al., "Enslaved Bacteria as New Hope for Plant Biotechnologists," Appl. Microbiol. Biotechnol., 54:302-310 (2000).

Heifetz, Peter B., "Genetic Engineering of the Chloroplast," Biochimie, 82:655-666 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IRESs): Reality and Use" Transgenic Research, 8:157-177 (1999).

Ivanov et al. "A Tobamovirus Genome That Contains an Internal Ribosome Entry Site Functional In Vitro," Virology, 232:32-43 (1997).

Jeon et al. (2000) "T-DNA insertional mutagenesis for functional genomics in rice" Plant J. 22:561-570.

Kofer et al., "PEG-Mediated Plastid Transformation in Higher Plants," In Vitro Cell. Dev. Biol.- Plant, 31:303-309 (1998).

Koshinsky et al. (2000) "Cre-lox site-specific recombination between Arabidopsis and tobacco chromosomes" The Plant Journal 23:715-722.

Kozak, "Initiation of Translation in Prokaryotes and Eukaryotes" Gene 234:187-208 (1999).

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant staphylococci on cotton fibers by functional display of a fungal cellulose-binding domain" FEMS Microbiology Letters 195:197-204.

Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use In Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts"Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85:2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure in Poly(A)-tail-promoted Translation In Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat × Tripsacum Crosses" Crop Science 33:973-976.

Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of Saccharomyces cerevisiae" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170 (1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al., "Expression of a Chimeric uidA Gene Indicates that Polycistronic mRNAs are Efficiently Translated in Tobacco Plastids," The Plant Journal, 7(5):845-848 (1995).

Suzuki et al., "Engineering of the rp123 Gene Cluster to Replace the Plastid RNA Polymerase α Subunit with the Escherichia coli Homologue," Curr. Genet., 38:218-225 (2000).

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Urwin et al. (2000) "Functional characterization of the EMCV IRES in plants" Plant J. 24:583-589.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in Arabidopsis thaliana by transient expression of cre" Plant Molecular Biology 38:393-406 (1998).

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

Hagemann et al. "Extranuclear Inheritance: Plastid Genetics" Progress in Botany, vol. 55, 260-275 (1994).

Klaus et al. "Generation of Marker Free Plastid Transformants Using a Transiently Cointegrated Selection Gene" Nature Biotechnology 22: 225-229 (2004).

Ruf et al. "Stable Genetic Transformation of Tomato Plastids and Expression of a Foreign Protein in Fruit" Nature Biotechnology 19: 870-875 (2001).

Sanz et al. "Altered local and systemic spread of movement deficient virus in transgenic tobacco plants expressing the cucumber mosaic virus 3a protein" Arch Virol. 145:2387-2401 (2000).

Shimada et al. "Fine Structural Features of the Chloroplast Genome: Comparison of the Sequenced Chloroplast Genomes" Nucleic Acids Research 19: 983-995 (1991).

Shinozaki et al. "The Complete Nucleotide Sequence of the Tobacco Chloroplast Genome: Its Gene Organization and Expression" The EMBO Journal 5: 2043-2049 (1986).

Sidorov et al. "Stable Chloroplast Transformation in Potato: Use of Green Fluorescent Protein as a Plastid Marker" The Plant Journal 19: 209-216 (1999).

Parry et al. "Construction of a bidirectional promoter probe vector and its use in analyzing nod gene expression in Rhizobium loti" Gene 150:105-109 (1994).

Derbyshire et al. "Lightning strikes twice: Intron-intein coincidence" Proc. Natl. Acad. Sci. USA 95:1356-1357 (1998).

Lustig et al. "Long Poly(A) Tracts in the Human Genome are Associate with the Alu Family of Repeated Elements" J. Mol. Biol. 180:753-759 (1984).

Wu et al. "Markerless Deletions of pil Genes in Myxococcus xanthus generated by Counterselection with the Bacillus subtilis sacB Gene" Journal of Bacteriology 178(19):5817-5281 (1996).

Scharff et al. "Linear molecules of tobacco ptDNA end at known replication origins and additional loci." Plant Mol. Biol. 62, pp. 611-621 (2006).

Donson et al. "Systemic expression of a bacterial gene by a tobacco mosaic" Proc. Natl. Acad. Sci. USA 88: 7204-7208 (1991).

Murakami et al. "High-level expression of exogenous genes by replication-competent retrovirus vectors with an internal ribosomal entry site" Gene 202: 23-29 (1997).

Attal et al., "The efficiency of different IRESs (Internal Ribosomes Entry Site) in monocistronic mRNAs," Molecular Biology Reports 27: 21-26 (2000).

Skulachev et al., "Internal Initiation of Translation Directed by the 5'-Untranslated Region of the Tobamovirus Subgenomic RNA $I_2$," Virology 263: 139-154 (1999).

Bateman et al. (2000) "Tools for chloroplast transformation in Chlamydomonas: expression vectors and a new dominant selectable marker" Mol. Gen. Genet. 263:401-410.

Fischer et al. (1996) "Selectable marker recycling in the chloroplast" Mol. Gen. Genet. 251:373-380.

Iamtham et al. (2000) "Removal of antibiotic resistance genes from transgenic tobacco plastids" 18:1172-1176.

Staub et al. (1994) "Extrachromosomal elements in tobacco plastids" Proc. Natl. Acad. Sci. 91:7468-7472.

Suzuki et al. (1997) "Generation and maintenance of tandemly repeated extrachromosomal plasmid DNA in Chlamydomonas chloroplasts" Plant J. 11:635-648.

Valancius et al. (1991) "Testing an "In-Out" Targeting Procedure for Making Subtle Genomic Modifications in Mouse Embryonic Stem Cells" Molecular and Cellular Biology 11:1402-1408.

* cited by examiner

1)

2)

SEQ. ID. No. 1 (tobacco plastome sequence 109986 to 111112 and 131514 to 132640):

gctcagaggattagagcacgtggctacgaaccacggtgtcgggggttcgaatccctcctcgcccacaaccggcccaaaagggaagtaccttc
cctctgggggtaggaaaatcatgatcgggatagcgaaccaaaagctatggaacttgggtgtgggtcttttgtcgaaatggaatggcttttcttttct
cttttatttatcgtgaatgggggaatcattacacatagtatgcccggtcagcatattttttgttttacgccccgtaactcttcctcagccaggcttggg
cagaatagcagagcaagtattagtagcataacaaaaaagccttcctcgtcattaatatctttgctcgcggcaattgtgacctctcgggagaatcgat
gactgcatctttgatgcagtgctagtatatctgagacttcttaattggctagttgtaaatagcccccagggctatggaacaaaggattatctcggacct
agaccgaggtattgatggtgattttctaatctcgcagaacagaatgtgatacgatgagatagaatgcaatagaaacaaagacagggaacggggtta
cctactcttaacgggcaaagcgagcccctttattctgaattctttaattcagaatcaatcaaatctccccaagtaggattcgaacctacgaccaatcg
gttaacagccgaccgctctaccactgagctactgaggaacaacaggagattcgatctcatagagttcaattcccgttcccaacccatgaccaatat
gagctcgaagcttccttcgtaactcccggaacttcttcgtagtggctcccttacatgcctcatttcagagggaacctcaaagtggctctatttcattat
attccatccatatcccaattccattcatttaatatcccttttggtgtcattgacataacagatgtcgtttctagtctatctctttctatttcttttctatatatgga
aagttcaaaaatcatcatataataatccagaaattgcaatagaaaagaaataagggaggtttgtgatgattttcaatcttttctactaggtaatctagt
atccttatgcatgaagataatcaattcggtcgttgtggtcggactc SEQ. ID. No. 2 (tobacco plastome sequence 112061 to 113058):

gaatttgattcacaaagttgaaaagagtaagtaataaactaataaaaagattgaaacataagctaaatacaagaaaagataagaagagatgcgtc
cgccccctatatatttgataccttctcctacaatgaaactaataaccccaaccccgttagtcatcccatcaattactcgtcgatcaaaaaaatgagtaa
attcagctaatcctcttatcccaccaactaagaatcttgtataaaaagcatctatgtaagcacgattatatgaccaatcatatgccatttataattttgt
cccacagaattctcttaggacccttttaacaaaagaattaattaactcaaaattttttaaagaagaataaatgggtttatataaaaaggatgctataaa
tattccgaaataagctatactgactgaaagaactgcatccttaaaaattcattccaatccatcgaattattcgacttttgatgcaaaagatttatagatg
gagctaaccatttcgataatatatccaaattccctccctcttggttgaaaggaattcctatagatccaacaaacaaagtaaagagtcctaatacaaat
attgggaatagcatagtattgtccgattcataaggataggaataaaccgctttatgctcaaaatgagcaatagtcataaaaggtcgtgtcatctttctt
ccattttatcaattggatatttagttttgcaaaaaaataagtactttcattattattcatagttaataaacaagagttttcttaactccgttttaccccata
gagatattgaatagaaggggggttttttgtttcccaccataatttggaaaatgagcgtttaaatgcccttcaaaagtaagtaaatagatccgaaacatat
aaaatgcggttaatcccgccgtggcccaagctattattgcgaaaattggcgaatacaaccaactatcattaagaatttcatctttggaccaaaaaca
agcaagaggtggaataccaca

Fig. 25

PROCESS OF GENERATING TRANSPLASTOMIC PLANTS OR PLANT CELLS DEVOID OF A SELECTION MARKER

CROSS-REFERENCE TO RELATED APPLICATIONS

The present application is a 35 § U.S.C. 371 National Phase Application of International Application Serial No. PCT/EP02/04777, filed Apr. 30, 2002 and published in English as PCT Publication No. WO 03/004658 A2 on Jan. 16, 2003, which claims priority to German Patent Application Serial No. DE 101 32 780.3, filed Jul. 6, 2001, the disclosures of each of which are incorporated herein by reference in their entireties.

FIELD OF INVENTION FIELD OF INVENTION

The present invention relates to plant biotechnology in general and more particularly to novel methods and vectors for plastid transformation. Specifically, the present invention provides a process of genetic transformation of plant plastids, vectors for the process, and plants or plant cells obtainable according to the process of the invention. Moreover, the present invention relates to vectors containing sequences conferring, preferably autonomous, replication capabilities useful in the process of the invention. The present invention also relates to a process of generating transgenic plants or plant cells transformed on their plastome and being devoid of a selection marker.

BACKGROUND OF THE INVENTION

According to generally accepted knowledge, two classes of cell organelles, i.e. plastids and mitochondria, are derived from initially independent prokaryotes that were taken up into a predecessor of present day eukaryotic cells by separate endosymbiotic events (Gray, 1991). As a consequence, these organelles contain their own DNA, DNA transcripts in the form of messenger RNA, ribosomes, and at least some of the necessary tRNAs that are required for decoding of genetic information (Marechal-Drouard et al., 1991).

While, shortly after endosymbiotic uptake, these organelles were genetically autonomous since they contained all the elements necessary to drive prokaryotic life, this autonomy was reduced during evolution by transfer of genetic information to the cell's nucleus. Nevertheless, their genetic information is of sufficient complexity to make recent cell organelles an attractive target for gene technology. This is particularly the case with plastids, because these organelles still encode about 50% of the proteins required for their main function inside the plant cell, photosynthesis. Plastids also encode their ribosomal RNAs, the majority of their tRNAs and ribosomal proteins. In total, the number of genes in the plastome is in the range of 120 (Palmer, 1991). The vast majority of proteins that are found in plastids are, however, imported from the nuclear/cytosolic genetic compartment.

Plastids Can Be Genetically Transformed

With the development of general molecular cloning technologies, it became soon possible to genetically modify higher plants by transformation. The main emphasis in plant transformation was and still is on nuclear transformation, since the majority of genes, ca. 26.000 in the case of *Arabidopsis thaliana*, the complete sequence of which was recently published (The *Arabidopsis* Genome Initiative, 2000), is found in the cell's nucleus. Nuclear transformation was easier to achieve, since biological vectors such as *Agrobacterium tumefaciens* were available, which could be modified to efficiently enable nuclear transformation (Galvin, 1998). In addition, the nucleus is more directly accessible to foreign nucleic acids, while the organelles are surrounded by two envelope membranes that are, generally speaking, not permeable to macromolecules such as DNA.

A capability of transforming plastids is highly desirable since it could make use of the high gene dosage in these organelles that bears the potential of extremely high expression levels of transgenes. In addition, plastid transformation is attractive because plastid-encoded traits are not pollen transmissible; hence, potential risks of inadvertent transgene escape to wild relatives of transgenic plants are largely reduced. Other potential advantages of plastid transformation include the feasibility of simultaneous expression of multiple genes as a polycistronic unit and the elimination of positional effects and gene silencing that may result following nuclear transformation.

Methods that allow stable transformation of plastids could indeed be developed for higher plants. To date, two different methods are available, i.e. particle bombardment of tissues, in particular leaf tissues (Svab et al., 1990), and treatment of protoplasts with polyethylene glycol (PEG) in the presence of suitable transformation vectors (Koop et al., 1996). Both methods mediate the transfer of plasmid DNA across the two envelope membranes into the organelle's stroma.

Conventional plastid transformation technology is described in Heifetz, 2000 and Koop et al., 1996.

Conventional plastid transformation vectors usually need to serve at least two purposes: (1) introduction of one or more desired foreign genes to be expressed by the genetic machinery of the plastids, and (2) selection of cells containing transformed plastomes by inhibitor selection and/or by screening for a detectable phenotype. Plastid transformation vectors usually contain complete gene cassettes consisting of four operable linked elements: a promoter sequence, a 5' untranslated region, a coding region, and a 3' untranslated region.

These cassettes, however, do not make use of the potential to co-express several genes in an operon under the control of a single promotor.

Selection is achieved either by replacing a complete resident plastid gene by a mutant gene, which confers resistance to selection inhibitors (U.S. Pat. No. 5,451,513) or by introducing a complete expression cassette, which leads to enzymatic inactivation of an inhibitor (U.S. Pat. No. 5,877,402). These marker genes that are needed for the selection of transgenic plant cells from a vast background of untransformed cells code for antibiotic or herbicide resistance genes. Examples for plastid resistance genes are aadA conferring resistance to spectinomycin and streptomycin (Svab & Maliga, 1993), or nptII conferring resistance to kanamycin (Carrer et al., 1993). As these marker genes are stably integrated into the genome together with the genes of interest (GOI), they will stay in the homoplastomic transgenic plants although they are not required for GOI function. These remaining marker genes are a main issue of criticism of plant biotechnology as they could theoretically increase antibiotic resistance of pathogens or herbicide resistance of weeds. Construction of a selection system which does not result in a resistance gene in the transgenic plant is, therefore, highly desirable (Iamtham and Day, 2000).

In addition to the two or more gene cassettes, transformation vectors usually contain flanking regions of the insertion site, which are necessary for the stable introduction of engineered sequences into the plastome by two reciprocal homologous recombination events. To this end, chloroplast transformation vectors contain chloroplast genome sequences to serve as homologous flanks. Since the chloroplast genomes of different species differ in their sequences, species-specific transformation vectors have to be used. This requires substantial effort, when cloning transformation vectors, and is in contrast to the situation in nuclear transformation.

In all conventional transformation vectors, the selection marker is flanked by sequences homologous to plastid DNA; therefore, it is stably integrated into the plastome, although it is not needed for the desired function of the sequence(s) of interest. These remaining marker genes could theoretically spread to other organisms by giving a selective advantage. Increased antibiotic resistance in pathogens might cause problems in clinical treatment. Thus, the development of a system which results in transplastomic plants not containing any selection marker is highly desirable. A further advantage of such a system would be the possibility of re-using the same marker gene for subsequent transformations, which is at present difficult due to the limited number of efficient selection markers.

Furthermore, the copy number of any transgene stably integrated into plastome molecules can obviously never exceed the plastome copy number, thus limiting the potential transgene expression level to a certain degree. Consequently, the copy number of the transgene(s) can be further increased when located on an extra-chromosomal element.

U.S. Pat. No. 5,693,507 discloses a process for introducing a heterologous DNA into a chloroplast whereby the heterologous DNA contains operably linked control elements allowing for expression in the chloroplast. The process according to U.S. Pat. No. 5,693,507 has not provided long-term maintenance of the heterologous DNA in a plastid. Moreover, the expression of the heterologous DNA in the plastid is insufficient for practical application.

Therefore, it is an object of the invention to provide an efficient and highly versatile process of genetic transformation of plant plastids whereby genetically stable transgenic plants may be produced.

It is another object of the invention to provide a process of genetic transformation of plant plastids, which gives stably transformed plants and allows very high transgene expression levels.

It is another object of the invention to provide a process of genetic transformation of plant plastids, which allows expression of multiple genes of interest (polycistronic expression).

It is a further object of the invention to provide a novel process of genetic transformation of plant plastids, which gives transgenic plants not containing a marker gene such as an antibiotic resistance gene.

It is a further object to provide vectors capable of replicating in plant cells, preferably in plastids, whereby the replication frequency of the vector is tuneable.

GENERAL DESCRIPTION OF THE INVENTION

The present invention provides a process of plastid transformation of plants or plant cells by transforming said plant or cells of said plant with a DNA or a vector capable of replicating in said cells, preferably in plastids of said cells. Replication of said DNA in said plastids can be achieved by including in said DNA a nucleotide sequence conferring replication to said DNA.

The present inventors have found that replication of said DNA in plant cells, notably in plastids, may take place by at least one of the following two mechanisms:

(i) said nucleotide sequence conferring replication may be sufficiently homologous to a plastome sequence leading to reversible integration of said DNA into the plastome by homolgous recombination. Thus, said DNA or said vector may be replicated indirectly or non-autonomously with said plastome (cf. FIG. 2). Since said integration is reversible, said DNA may be excised from the plastome, whereby indirectly replicated DNA is produced;

(ii) said nucleotide sequence conferring replication may comprise an origin of replication causing autonomous replication of said DNA independent of plastome replication.

When mechanism (ii) is active, replication according to mechanism (i) may be active concomittantly if said nucleotide sequence conferring replication and/or said origin of replication is sufficiently homologous to a plastome sequence for reversible integration according to mechanism (i).

Based on the above mechanisms, the inventors of this invention have found that it is possible to create vectors with an extremely broad range of replication frequencies, i.e. the replication frequency of a vector may be designed to be at a suitable level for a desired purpose. In said range of replication frequencies, the lowest replication frequency is achieved according to mechanism (i) with a nucleotide sequence conferring replication that is devoid of a sequence having the function of an origin of replication. Replication of said DNA preferably occurs by integration into a plastome, replication with said plastome and excision of said DNA out of said plastome (reversible integration mediated by recombination via a single homologous flank). Thus, in mechanism (i), the replication frequency of said DNA (or said vector) is limited by the replication frequency of the plastome.

The replication frequency of said DNA may be increased by including in said DNA a nucleotide sequence conferring autonomous replication, e.g. an origin of replication functional in the cells, notably in plastids, transformed. Typically, a functional origin of replication in said DNA will share homology with a natural origin of replication of said plastome, thereby potentially mediating reversible integration of said DNA into the plastome. Therefore, autonomous and non-autonomous replication of said DNA may both be active at the same time. The autonomous replication frequency may be modulated by selecting an origin of replication with the desired activity. The maximum autonomous replication frequency is given by the most active known origins of replication active in said cells. Alternatively, said nucleotide sequence conferring replication may have an origin of replication not having homology to the plastome. Such an origin of replication allows autonomous replication according to mechanism (ii), whereby mechanism (i) is not active.

This invention discloses embodiments where a very high replication frequency is desired. Further, embodiments are disclosed where the replication frequency is low, e.g. where non-autonomous replication takes place exclusively. Between these extremes, the replication frequency of said DNA may be adjusted to the requirements of the particular case.

PREFERRED EMBODIMENTS OF THE INVENTION

This invention provides a process of genetic transformation of plant plastids, comprising the following steps:
(a) providing a plant plastid with DNA, which:
  (i) comprises a nucleotide sequence conferring autonomous replication of said DNA in a plant cell,
  (ii) comprises at least one sequence of interest; and
  (iii) said DNA is for transcription
    (α) devoid of transcription initiation and/or termination control elements operably linked to said at least one sequence of interest; or
    (β) devoid of transcription termination control element operably linked to said at least one sequence of interest, while it comprises a transcription intitiation control element operably linked to said at least one sequence of interest,
(b) allowing for replication of said DNA; and
(c) recovering cells and/or plants carrying genetically transformed plastids.

The process of the invention can lead to exceptionally high expression levels of at least one sequence of interest. At the same time, the process of the invention allows expression of multiple sequences of interest (polycistronic expression).

According to the invention, the DNA comprises a nucleotide sequence conferring preferably autonomous replication to said DNA in a plant cell, which leads to the production of many copies of said DNA. Said nucleotide sequence conferring replication may be any sequence which allows replication of said DNA in a plant cell, preferably in plastids. Examples for such sequences are the plastid origins of replication oriA and oriB. Further examples are novel nucleotide sequences conferring replication in plastids according to SEQ. ID. No: 1 and SEQ. ID. No: 2. Autonomous replication of said DNA means that said DNA can be replicated inside the plant cell independent of the replication of other DNA in said cell, notably without integration in the plastome.

The process of the invention may be used in cases when integration of a sequence of interest into the plastome is desired (case α), whereby said integration is preferably stable. For this purpose, it is preferred that (vectorial) DNA is devoid of transcription initiation and/or termination control elements operably linked to said at least one sequence of interest. In this case, transcription of said sequence of interest may rely fully on control elements (for initiation and termination) already present in the plastome (plastomal). Alternatively, only the control element for initiation of transcription may be plastomal, while the control element for termination may be provided in the (vectorial) DNA. Alternatively, only the control element for termination of transcription may be plastomal, while the control element for initiation may be provided in the (vectorial) DNA. In any event, the (vectorial) DNA lacks at least one of the control elements for transcription. This renders the transformation of case (α) more efficient and stable.

The process of the invention may further be used in cases when integration of a sequence of interest into the plastome is not desired (case β). For this purpose, it is preferred that the (vectorial) DNA is devoid of a transcription termination control element operably linked to said at least one sequence of interest, while it comprises a transcription intitiation control element operably linked to said at least one sequence of interest. In this case transcription proceeds with an autonomous DNA without integration. Therefore, a transcription initiation element is provided in the DNA and operably linked to the sequence of interest. However, no transcription termination element operably linked to said sequence of interest is provided in said DNA. This means that transcription occurs in a "rolling circle" fashion and termination occurs without termination control element, but rather on a statistical basis.

In one preferred embodiment said at least one sequence of interest has no operably linked control element for transcription termination. Preferably, said DNA or a part thereof is not integrated into the plastome. Once transcription of said DNA or a sequence of interest has started, it is not or rarely terminated. This leads to very long transcripts comprising multiple units of RNA corresponding to said DNA or, preferably, multiple units of the transcribed sequence(s) of interest. As a result, the amount of transcripts of said sequence(s) of interest is increased compared to the conventional case where a sequence of interest has an operably linked transcription terminator. Consequently, translation will be enhanced as well.

The presence of features (i), (ii), and (iii) is multiplicative, thus potentiating the expression level of said sequence(s) of interest. Furthermore, multiple sequences of interest may be expressed from said DNA from the same promoter.

The at least one sequence of interest may generate a desired function by interaction with any component of the plant cell, preferably a component of the plastid like the plastid genome or an expression product of the plastid genome. Alternatively, an expression product of said at least one sequence of interest may generate a desired function by the above-mentioned interaction. Such interactions may be used for the construction of two-component transgenic plant expression systems. These contribute enormously to the biological safety of transgenic plants, since expression is only functional if two artificial components are present in the same plant.

Expression comprises at least transcription e.g. if RNA is a desired product (e.g. for anti-sense technology). Preferably, expression comprises transcription and translation for the production of a polypeptide or protein. In the case of polypeptide expression, "sequence of interest" preferably relates to the coding part of the polypeptide.

It is preferred that said DNA is circular. It should preferably be able to replicate autonomously. Replication may occur in plastids and/or outside plastids. In the case of one sequence of interest to be expressed, this sequence will preferably have an operably linked transcription initiation element but no transcription termination element (case β). Generally speaking, in the case of several sequences of interest, it is preferred that only one, preferably the first one, has a transcription initiation element, while no termination element is present. Alternatively, several or all sequences of interest may have initiation elements, but transcription termination elements are absent. It is thus preferred that initiation element(s) is (are) present, while termination elements are absent.

For efficient translation, each sequence of interest preferably has a ribosome binding site. Other sequences for promoting translation like translation enhancers may be operably linked to one or more sequences of interest.

According to the invention, plant plastids are genetically transformed with DNA (a vector) by providing a plastid with said DNA. Said providing a plastid with said DNA may be indirect or direct. An example of indirectly providing said DNA is the case wherein said DNA is autonomously replicated outside of the plastid (e.g. in the cell nucleus), thus generating multiple copies of said DNA. These copies may subsequently be transferred to the plastids. Preferably, said providing a plastid with said DNA is direct and said DNA is autonomously replicated in plastids. The type of nucleotide sequence used for conferring replication of said DNA is preferably adjusted to the compartment where the autonomous replication of said DNA is supposed to take place. For autonomous replication in plastids for example, said nucleotide sequence conferring replication has to be functional in plastids.

Said nucleotide sequence conferring autonomous replication of said DNA may be any known origin of replicaion, or any other nucleotide sequence having the function of conferring autonomous replication. Depending on the specific embodiment, it may be advantageous to modulate the capability of said nucleotide sequence to confer replication. For example, a very active origin of replication (high frequency of replication) may allow the maintain of said DNA in a plant cell without selecting for maintenance of said DNA. An origin of replication with limited capability of conferring replication may allow to remove said DNA from a plant cell when selection pressure is lifted. Modulation of said capability or said frequency may be achieved by selecting such a nucleotide sequence from a suitable plant species. Alternatively, a given origin of replication may be modified e.g. by mutations, truncation, combination or shuffling and recombination of more than one origin of replication etc. in order to achieve a capability of conferring replication which is suitable for a given embodiment or purpose.

Said DNA may further contain one or more sequences providing for selection (selectable marker) of transformed plants, plant cells or plastids. Such a selectable marker may be an antibiotic or inhibitor resistance gene. Alternatively, a plastid gene required for growth under certain conditions may have been rendered dysfunctional or may have been eliminated in a previous step. Inclusion of said plastid gene in said DNA in a form functional for allowing positive selection of said transformation may be used as a selectable marker. Examples for such a gene are genes directly or indirectly related to photosynthesis like rpoA or petA. The latter procedure has the great advantage that the process of the invention may be performed without introducing an antibiotic resistance gene into a plant.

In one general embodiment of the invention, said DNA replicates autonomously in plastids, i.e. it is an extrachromosomal or episomal element in plastids. Said DNA preferably does not contain a transcription termination element operably linked to a sequence of interest, thus enabling polycistronic expression of multiple genes of interest. Compared to conventional plastid transformation strategies, this process may lead to a much higher expression level, as the copy number of the autonomously replicating plasmids can strongly exceed the copy number of the plastome molecules leading to a increased gene dosage of said at least one sequence of interest. In this embodiment, vectors may be constructed which are not species-specific, as the use of homologous flanks for recombination with the plastome are not needed. Thus, the effort for vector cloning is strongly reduced, which represents an enormous advantage of this process. Furthermore, due to the near absence of sequences homologous to plastome sequences, the resulting transgenic plants are genetically very stable.

Vectors or said DNA containing plastome sequence elements, which serve as replication initiation start sites are maintained in the plastids, if appropriate selection is applied, or if the replication frequency of the extra-chromosomal DNA exceeds the respective replication frequency of the plastome molecules.

It is evident that autonomously replicating elements are lost without selection, if the replication frequency of the plasmid is below the replication frequency of the plastome. In order to preserve the presence of the autonomously replicating DNA, even if it has a replication frequency below that of the plastome, a selectable marker can be included with said DNA. As mentioned above, a photosynthesis related gene (e.g. petA) may be removed from the plastome or rendered dysfunctional in a first step of transformation. In a second step, the missing gene may be supplied with an autonomously replicating element according to the process of this invention. Using this procedure, the plants growing on soil are 'forced' to maintain the introduced element(s). The efficiency of said second step may be improved by using a selectable marker on said DNA and appropriate selection pressure, whereby said marker is located outside of homologous flanks and may get lost as described in detail below. This procedure allows the generation of transplastomic higher plants, that do not carry any antibiotic resistance or herbicide resistance marker gene.

In a second general embodiment of the invention, said DNA further contains sequences allowing stable integration of at least a portion of said DNA into the plastome by homologous recombination. Said DNA may be used as a shuttle for the introduction of a sequence portion of said DNA, preferably of a sequence of interest, into the plastome. At present, plastid transformation is dependent on the use of antibiotic resistance genes as selection markers, which are retained in the end product as an unwanted and strongly controversial side effect. To solve this problem, said DNA may be provided with a plastome integration cassette, i.e. a sequence to be integrated into the plastome flanked by sequences allowing stable integration (sequences homologous to parts of the plastome). Preferably, the selectable marker gene of said DNA is positioned outside of this integration cassette. Selection is preferably sustained until the sequence to be integrated (preferably a sequence of interest) is stably integrated into a sufficient number of plastome copies. Then, selection is released, leading to loss of the autonomously replicating DNA containing the selectable marker, thus allowing the generation of marker-free transplastomic plants. To ensure loss of the autonomously replicating extrachromosomal plasmid, the plasmid (DNA) is preferably provided with a sequence conferring autonomous replication at an adequate frequency, i.e. a frequency which is not too high such that loss of said DNA is not prevented. Such sequences conferring replication can be created easily by using a well defined part of the sequences described herein (SEQ ID NO:1 and SEQ ID NO:2) which confer autonomous replication at high frequencies.

Another way of achieving marker-free transformants is described herein, in which a selection marker is removed from the shuttle plasmid using homologous recombination mediated by a direct repeat of the plasmid vector sequence flanking a non-integrateable marker gene.

This invention further provides vectors for the above-mentioned processes. Particularly, a vector is provided which contains a nucleotide sequence conferring the capability of autonomous replication in a plant plastid, said nucleotice sequence selected from the following group:
(a) sequence of SEQ ID NO:1 or a functionally conservative variant or part thereof;
(b) the sequence of SEQ ID NO:2 or a functionally conservative variant or part thereof;
(c) sequence which hybridizes under stringent conditions to a sequence which is complementary to a sequence of (a) or (b);

(d) a sequence according to (a) or (b) containing selected mutations for attenuating or promoting said capability of conferring autonomous replication to said DNA;
(e) a sequence which is at least 80% identical to SEQ ID NO:1 or SEQ ID NO:2;
(f) a sequence orthologous to the sequence of SEQ ID NO:1 or to SEQ ID NO:2, or a part thereof.

It has been surprisingly found that the sequences of SEQ ID NO:1 or SEQ ID NO:2 provide for efficient replication of DNA in plant plastids. Most surprisingly, said sequences do not contain any known plastid origin of replication. The sequences of SEQ ID NO:1 or SEQ ID NO:2 or variants thereof may e.g. be used in a process of conferring the capability of autonomous replication to a DNA. The frequency with which these sequences confer autonomous replication may be modulated as mentioned above. Particularly, homologous sequences or orthologous sequences from other organisms may be used in such a process.

This invention further provides a process of generating transgenic plants or plant cells transformed on their plastome and being devoid of a selectable marker, comprising the following steps:
(1) transforming plastids of a plant or plant cell with a DNA comprising:
  (i) a nucleotide sequence conferring replication of said DNA in a plant cell,
  (ii) at least one sequence of interest,
  (iii) sequences flanking said at least one sequence of interest necessary for stable integration of said at least one sequence of interest into the plastid genome, and
  (iv) a selection marker outside of said sequences flanking said sequence(s) of interest;
(2) allowing integration of said at least one sequence of interest into the plastome in the presence of selective pressure;
(3) allowing loss of said selection marker sequence by releasing selective pressure; and
(4) recovering cells and/or plants carrying genetically transformed on their plastome and being devoid of said selection marker.

This process allows the generation of transgenic plants which are devoid of a selectable marker. Such processes are highly desirable for reasons of biological safety and containment of antibiotic resistance genes. Where applicable and unless specified differently below, the information given above applies to this process. Said process of generating transgenic plants requires transformation of plastids with a DNA having a plastid integration cassette comprising at least one sequence of interest which is flanked by sequences necessary for stable integration of said at least one sequence of interest into the plastome by homologous recombination. Said DNA further has a selectable marker, e.g. an antibiotic resistance gene, which is preferably used to secure maintenance of said DNA in a plastid. Said selectable marker is positioned outside of said integration cassette. Consequently, it is not integrated into the plastome, notably it is not stably integrated. After integration, release of selective pressure allows loss of DNA that is not stably integrated. Said DNA may further have a nucleotide sequence conferring replication of said DNA allowing for propagation of said DNA.

Said nucleotide sequence conferring replication of said DNA may confer replication of said DNA outside of the plant plastid (e.g. in the nucleus or the cytoplasm) for subsequent transfer into plastids. Preferably, however, said nucleotide sequence confers replication of said DNA in plastids.

Said replication, notably in plastids, may be non-autonomous by reversible (or transient) integration of said DNA into the plastome. In this case, said nucleotide sequence conferring replication of said DNA provides for reversible integration of said DNA into the plastome. Said reversible integration may be provided by an integration sequence of said DNA which is sufficiently homologous to a sequence of the plastome for homologous recombination, preferably leading to integration of the complete vector (said DNA) into the plastome. Integrated in the plastome, said DNA may be replicated together with the plastome. Reversion of the recombination (see item 2a in FIG. 2) may lead to excision of the vector. The function of said integration sequence may be provided by one or both of said sequences flanking said sequence of interest (iii) or by a further sequence other than said flanking sequence. A further sequence capable of functioning as an integration sequence is preferably located outside said sequences flanking said sequence of interest. Consequently, said DNA has at least two sequences that are potentially capable of performing the function of said nucleotide sequence conferring replication. Additionally, said DNA may have one or more further sequences having said function.

Said replication may additionally be autonomous. In this case, said nucleotide sequence conferring replication of said DNA has an origin of replication in said plastids. Said origin of replication may be contained in one or both of said sequences flanking said sequence of interest. Preferably, said DNA has one or more further nucleotide sequence(s) conferring replication of said DNA and containing an origin of replication. Said one or more further nucleotide sequence(s) are preferably located outside of said sequences flanking said sequence of interest.

The process of generating transgenic plants or plant cells devoid of a selection marker may be used for many different purposes. It may be used for introducing one or more transgenes into plant plastids, e.g. for conferring the plant with a useful trait. In this case, said sequence of interest may contain a sequence coding for a polypeptide, optionally with regulatory elements that may be necessary for expression of said coding sequence.

Said process may also be used for introducing one or more mutations into the plastid genome, e.g. for changing the properties of a plastid encoded protein or RNA or for changing a regulatory sequence of a plastid gene. Such mutations may be introduced using said DNA, whereby said sequence of interest consists of the bases to be changed in the plastome flanked by said sequences flanking said sequence of interest. Said process may be used to change a single base in the target plastome in which case said sequence of interest may consist of a single base. Preferably, at least two, more preferably at least three bases are mutated, whereby said sequence of interest may consist of these at least two or three bases, respectively.

Further, said process may be used for deleting a desired sequence of the plastome. This may be done with concomitant insertion of a sequence of interest (sequence replacement) or without concomitant sequence insertion. In the latter case, said DNA may not have a sequence of interest and said flanking sequences are homologous to plastome sequences that flank said nucleotide sequence of the plastome to be deleted.

Said sequence of interest may further contain a sequence which allows visual identification of cells containing transformed plastomes, e.g. GFP. Step (d) of said process, may comprise allowing segregation of leaf sectors each containing a particular type of plastome. Leaf sectors identified visually identified may be used for selection, thus accelerating the process of reaching a homoplastomic state and the process of regenerating transgenic plants.

The invention also relates to a plant or plant cell comprising plastids obtained or obtainable by a process of this invention including products derived from such plants. Further vectors are provided having a sequence of interest, sequences flanking said sequence of interest necessary for stable integration of said sequence of interest into the plastid genome, and a selection marker outside of said sequences flanking said sequence(s) of interest.

DEFINITIONS

3'-UTR: transcribed but not translated region of a (→) gene, downstream of a (→) coding region;
5'-UTR: transcribed but not translated region of a (→) gene, upstream of a (→) coding region; in (→) plastid (→) genes, the 5'-UTR contains sequence information for translation initiation (ribosome binding site, (→) RBS) close to its 3' end;
aadA: (→) coding region of bacterial aminoglycoside adenyl transferase, a frequently used protein, that detoxifies the antibiotic (→) selection inhibitors spectinomycin and/or streptomycin;
aphA-6 (–>) coding region of bacterial aminoglycoside phosphotransferase A-6, a protein that detoxifies the antibiotic (–>) selection inhibitor kanamycin
chloroplast: (→) plastid containing chlorophyll;
coding region: nucleotide sequence containing the information for a) the amino acid sequence of a polypeptide or b) the nucleotides of a functional RNA; coding regions are optionally interrupted by one or more (→) intron(s);
desired gene (sequence): modified or newly introduced sequence: the purpose of a (→) transformation attempt;
flank, flanking region: DNA sequences at the 5' and 3' ends of inserts in a (→) plastid (→) transformation (→) vector, which mediate integration into the target (→) plastome of sequences between the flanks by double reciprocal (→) homologous recombination. By the same mechanism, sequences can be modified or removed from the target (→) plastome. Thus, the flanks of the (→) plastid (→) transformation (→) vector determine, where changes in the target (→) plastome are generated by (→) transformation;
gene expression: process turning sequence information into function; in (→) genes encoding polypeptides, gene expression requires the activity of a (→) promoter, which initiates and directs RNA polymerase activity, leading to the formation of a messenger RNA, which is subsequently translated into a polypeptide; in (→) genes encoding RNA, the (→) promoter-mediated activity of RNA polymerase generates the encoded RNA;
gene(s): nucleotide sequence(s) encoding all elements, which are required to secure function e.g. expression independently; genes are organised in (→) operons, which contain at least one complete (→) coding region; in (→) genes encoding polypeptides, these elements are: (1) a (→) promoter, (2) a 5' untranslated region ((→) 5'-UTR), (3) a complete (→) coding region, (4) a 3' untranslated region ((→) 3'-UTR); in (→) genes encoding RNA, the (→)5'-UTR, and the (→)3'-UTR are missing; in (→) operons consisting of more than one (→) coding region, two subsequent complete (→) coding regions are separated by a (→) spacer, and (→) promoter, (→) 5'-UTR and (→) 3'-UTR elements are shared by the (→) coding regions of that (→) operon;
genome: Complete DNA sequence of a cell's nucleus or a cell organelle;
GFP green fluorescent protein
homologous recombination: process leading to exchange, insertion or deletion of sequences due to the presence of (→) flanks with sufficient sequence homology to a target site in a (→) genome;
intron: sequence interrupting a (→) coding region;
operon: organisational structure of several (→) genes sharing a promoter;
plant(s): organism(s) that contain(s) (→) plastids in its (their) cells; this invention particularly relates to multi-cellular (→) plants; these include the group of gymnosperms (such as pine, spruce and fir etc.) and angiosperms (such as the monocotyledonous crops maize, wheat, barley, rice, rye, Triticale, sorghum, sugar cane, asparagus, garlic, palm tress etc., and non-crop monocots, and the dicotyledonous crops tobacco, potato, tomato, rape seed, sugar beet, squash, cucumber, melon, pepper, Citrus species, egg plant, grapes, sunflower, soybean, alfalfa, cotton etc.), and no-crop dicots as well as ferns, liverworts, mosses, and multicellular green, red and brown algae;
plastid(s): organelle(s) with their own genetic machinery in (→) plant cells, occurring in various functionally and morphologically different forms, e.g. amyloplasts, (→) chloroplasts, chromoplasts, etioplasts, gerontoplasts, leukoplasts, proplastids etc;
plastome: complete DNA sequence of the (→) plastid;
promoter: nucleotide sequence functional in initiating and regulating transcription;
RBS, ribosomal binding site: DNA sequence element upstream of the (→) translation start codon of a (→) coding region, that mediates ribosome binding and translation initiation from the respective RNA transcript; RBS elements are either part of (→) 5'-UTRs or of (→) spacers;
selection inhibitor: chemical compound, that reduces growth and development of non-transformed cells or organelles stronger than that of transformed ones;
sequence of interest modified or newly introduced sequence of any length: the purpose of a (–>) transformation attempt; if introduction of a sequence is not intended, the length of the sequence of interest can be zero, i.e. it can be of interest not to have a sequence of interest.
termination: in the description of this invention, "termination" relates to discontinuation of transcription of RNA from a DNA sequence;
Terminator: sequence element responsible for (→) termination;
transformation vector: cloned DNA molecule that was generated to mediate (→) transformation of a (→) genome;
transformation: process leading to the introduction, the excision or the modification of DNA sequences by treatment of (→) plants or plant cells including the use of at least one (→) transformation vector;
transgene: DNA sequence derived from one (→) genome, introduced into another one;
uidA: (→) coding region of bacterial β glucuronidase, a frequently used reporter protein.

SHORT DESCRIPTION OF THE FIGURES

FIG. 1 Scheme of recombination events in conventional plastid transformation: double recombination in two flanking regions of homology. Integration of the selection marker and sequences of interest without vector sequences. Bottom: pattern definition as used in FIG. 1 and FIG. 2.

FIG. 2 Scheme of recombination events for transient marker integration: selection marker outside of homologous flanks, sequence of interest between flanks.
1) primary recombination: integration of the complete vector sequence via one region of homology.
2) secondary recombination due to direct repeats: a) excision of vector sequence (reversion of primary recombination). b) excision of selection marker and vector backbone; sequence of interest remains in the plastome FIG. 3 Map of plastid transformation vector pKCZ.

FIG. 4 Schematic drawing illustrating complete pKCZ vector integration into the plastid genome. The unstable intermediate can give rise to two possible recombination products resulting from duplicated flanks, either wild type (case I) or a stably integrated selection cassette (case II). The positions for primers used for PCR analysis are indicated by filled triangles.

FIG. 5 PCR analysis of tobacco transformants containing pKCZ. Gel A (cycle 0), Gel B (cycle I) and Gel C (cycle II) show the products obtained using primers oSH3 and oSH58 which are specific for detecting complete pKCZ integration. Gel D, illustrates that with the primer combination oFCH60 and oSH58 all the cycle-II lines still contain the aadA selection cassette even though not all carry complete vector insertion events.

Figure 17:
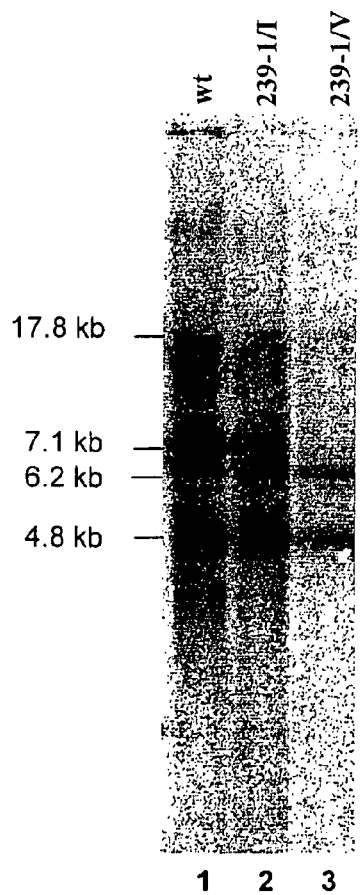

FIG. 17 shows a Southern analysis of plants transformed with pICFB1. NcoI-restricted total splant DNA was separated on a 1% agarose gel and hybridized with a labeled probe corresponding to tobacco plastome sequence 109986 to 111112. Lane 1: DNA from untransformed plants (*Nicotiana tabacum* cv. Petite Havana); lane 2: DNA from transplastomic line 239-1 after one cycle of shoot regeneration; lane 3: DNA from transplastomic line 239-1 after five cycles of shoot regeneration.

Figure 18:
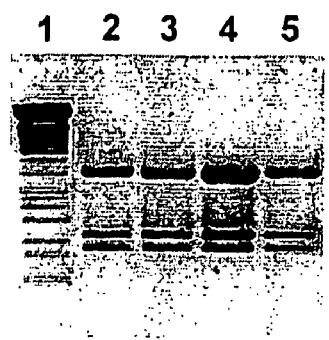

FIG. 18 shows a restriction analysis of pICFB1 recovered from transplastomic plants. Lane 1: DNA standard Lambda DNA/Eco1301-Mlul (MBI Fermentas, Vilnius, Lithuania) showing fragments of 956, 1268, 1489, 1882, 2205, 2419, 2690, 3472, 4254, 5090, 6223, 7743, 9824, 19329, and 26287 bp; lane 2: plastid transformation vector pICFB1, HindIII-restricted, showing fragments of 1276, 1507, and 3428 bp; lanes 3 to 5: HindIII-restricted plasmid DNA from three individual colonies obtained after transformation of *E. coli* with DNA isolated from transplastomic plant line 239-2.

Figure 19:
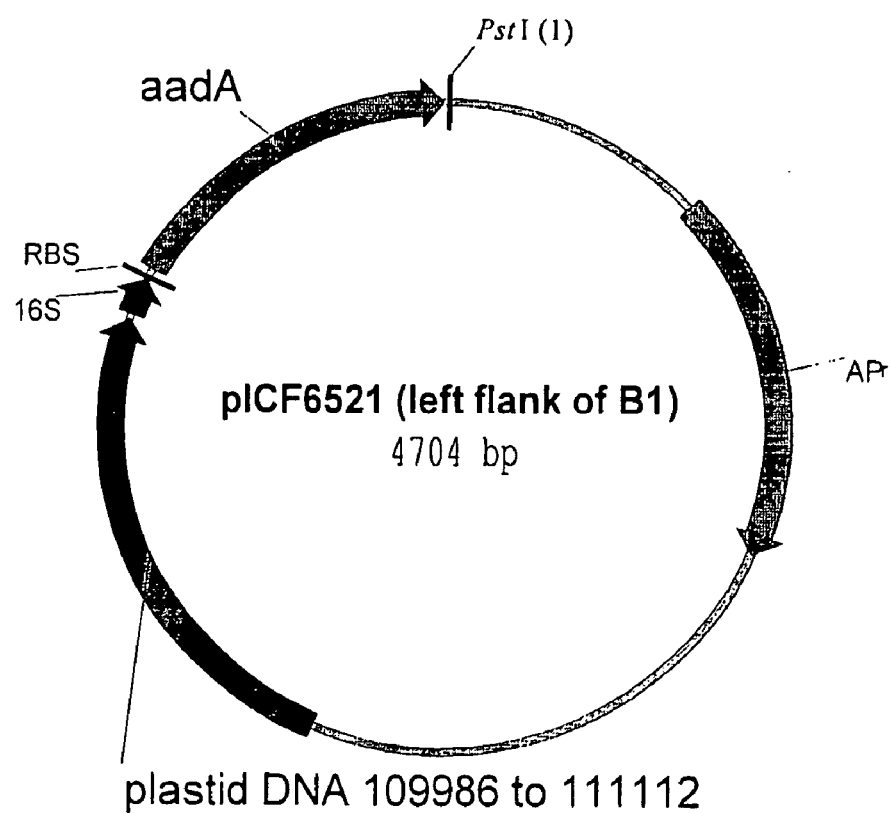

FIG. 19 shows a map of plastid transformation vector pICF652.

Figure 20:
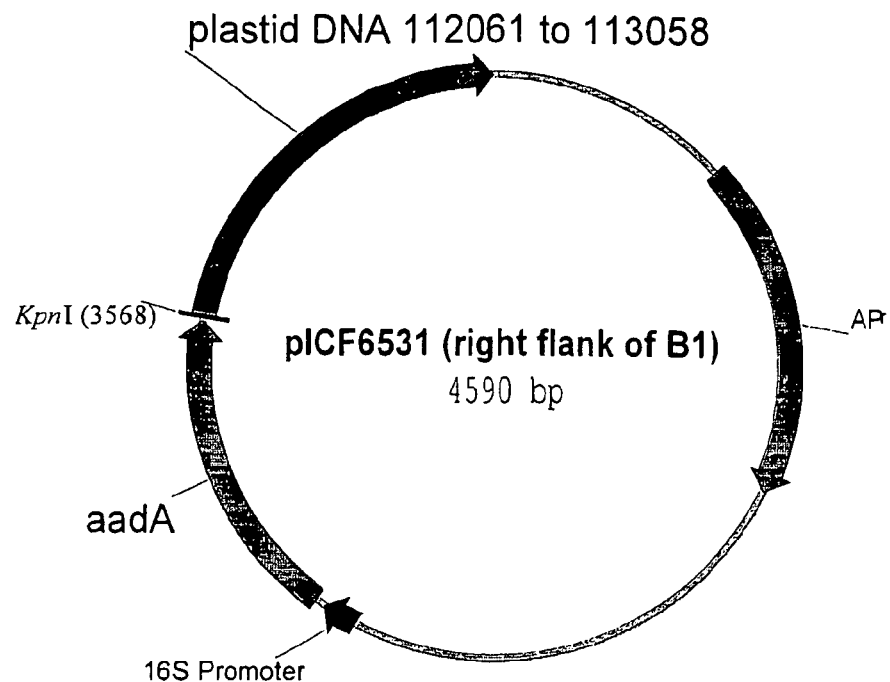

FIG. 20 shows a map of plastid transformation vector pICF653.

Figure 21:
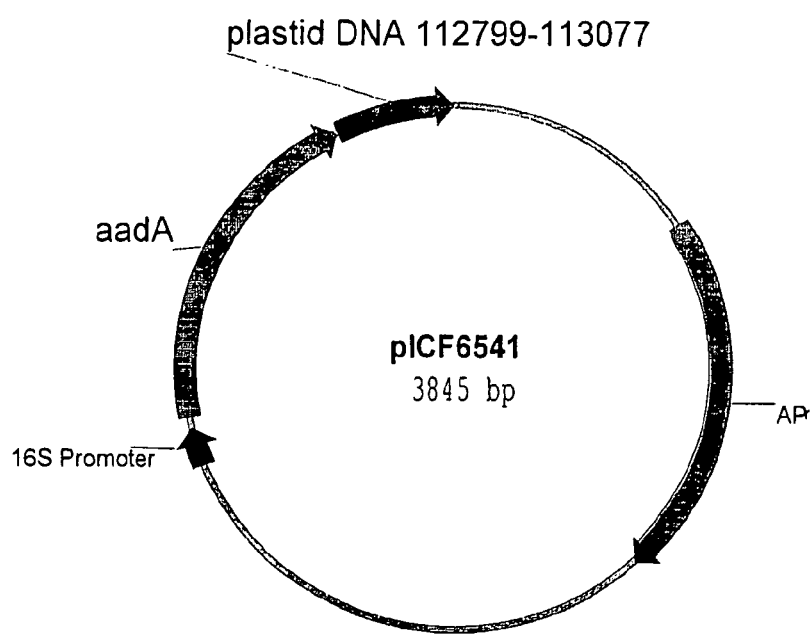

FIG. 21 shows a map of plastid transformation vector pICF654.

Figure 22:
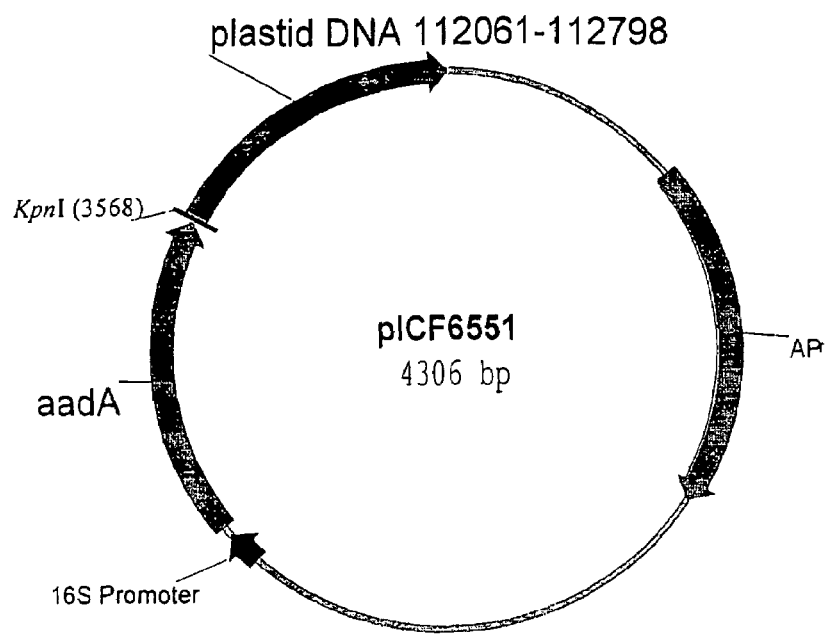

FIG. 22 shows a map of plastid transformation vector pICF655.

Figure 23:
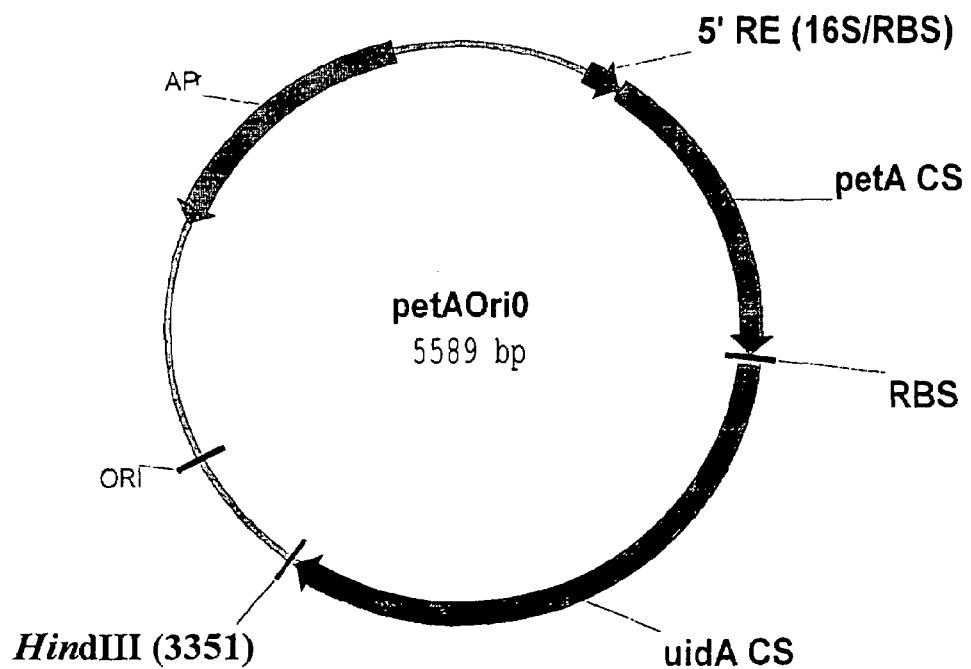

FIG. 23 shows plastid transformation vector petAOri0; the HindIII site is the cloning site for the 4 derivates petAOri1, petAOri2, petAOri3, and petAOri4.

Figure 24:
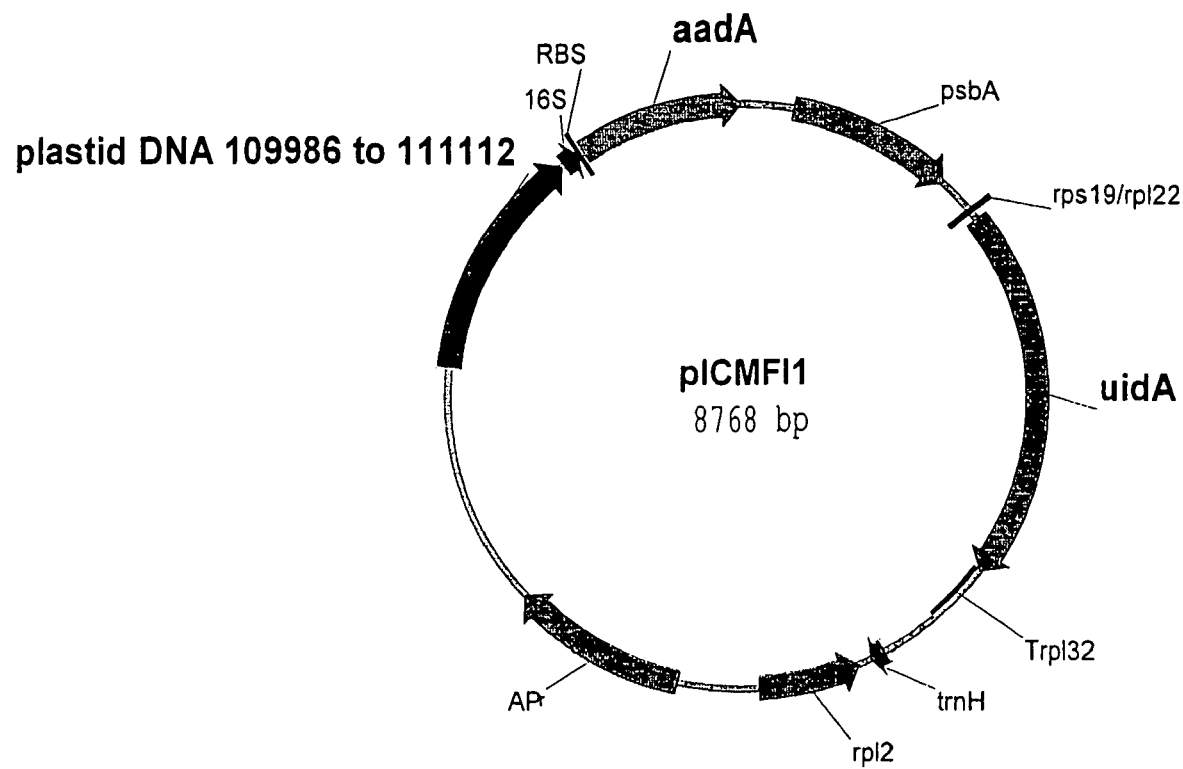

FIG. 24 shows plastid transformation vector pICMFI1.

FIG. 25 shows SEQ. ID. NO:1 and SEQ. ID. NO:2.

DETAILED DESCRIPTION OF THE INVENTION

Conventional Plastid Transformation Vectors Share a Common Structure

Besides the development of methods to introduce DNA into plastids, two further requirements had to be met for achievement of plastid transformation, namely the use of plastid sequence elements regulating gene expression, and enabling site directed integration of novel or modified sequences by homologous recombination. Conventional plastid transformation vectors contain flanks that are derived from plastome sequences upstream and downstream of the targeted insertion site (Zoubenko et al., 1994). As a consequence of these requirements, plastid transformation vectors used for the introduction of foreign genes into the plastome of higher plant plastids share the following elements: (1) a 5' flank, (2) a promoter sequence, (3) a 5' untranslated region, (4) a coding region, which encodes the complete sequence of a protein gene or a non protein gene (such as an RNA gene), (5) a 3' untranslated region, and a 3' flank. In addition (7), a plastid origin of replication was postulated to facilitate integration of sequences into the plastome (U.S. Pat. No. 5,693,507).

This general structure imposes some limitations on the use of these vectors: (1) These vectors are species specific, (2) a selection marker remains in the transplastomic plants, (3) every gene has to be transcribed from a separate promotor due to the terminator element, (4) the various plastid control elements, which are needed for the expression of several genes at the same time, may lead to genetic instabilities due to unwanted homologous recombination events, (5) the copy number of the transgene(s) can never exceed the copy number of the plastome.

This invention describes a new method for plastid transformation, which overcomes the limitations described above.

The Novel Vectors of this Invention Make Use of Plastome Sequence Elements, Which Serve As Replication Initiation Site, "Origins of Replication"

The understanding of replication of higher plant plastid chromosomes can be summarized as follows: the circular, double-stranded molecules (ca. 130-150 kbp) consist of four regions, a 'large single copy region', a 'repeat A', a 'small single copy region', and a 'repeat B', which is identical in sequence but inverted in orientation relative to repeat A. Replication is presumed to start from sequence elements called 'ori A' and 'ori B'. Since these elements are located within the repeated regions in the tobacco plastome, there are two copies of each of the elements. Characteristic of early replication are 'displacement loops'. These are converted to 'rolling circles' as replication proceeds (reviewed by Kunnimalaiyaan and Nielsen, 1997).

Vectors which contain plastid replication start sequences but which do not lead to stable integration of foreign sequences into the chloroplast genome, can be maintained in the plastids, if appropriate selection is applied, or if the replication frequency of the extra-chromosomal plasmids exceeds the respective replication frequency of the plastome molecules. Indeed, such plasmid-like structures have been reported in the literature. Staub and Maliga (1994), performing chloroplast transformation experiments, observed the spontaneous formation of 'NICE1', a plasmid-like molecule which was much smaller than the originally used transformation vector. If supplied also with an appropriate bacterial replication signal, it could even be used as a shuttle vector between E. coli and higher plant chloroplasts. The NICE1 element was lost, once selection pressure was omitted. Sequences on the shuttle vectors showed recombination with homologous sequences in the plastome (Staub and Maliga 1995); this observation favors the explanation that these elements are not replicated autonomously, but are integrated in the plastome during replication and excised by recombination events. This interpretation is also most likely true for the case of high-copy extra-chromosomal elements found in Chlamydomonas reinhardtii chloroplasts as an unexpected result of plastid transformation (Suzuki et al. 1997). These elements were accompanied by plastome rearrangements and could not be used as the basis for shuttle vectors; secondary transformation destabilized the occurrence of these elements.

Use of 'ori' sequence elements for plastid transformation is also described in a different context (Daniell et al. 1990; U.S. Pat. No. 5,693,507). Here, sequences containing the pea 'oriA' element are used in short term (up to 120 hrs) expression studies in cultured tobacco cells, which were mainly carried out in vitro. Concepts of chloroplast gene technology do, however, require long term and stable expression of foreign genes in vivo.

We have now surprisingly observed long term (more than one year; up to nine cycles of repeated regeneration from leaf explants in the presence of selection pressure) maintenance of plasmids in transformed tissues (see example 7). Transformation of bacteria with total DNA extracted from transformed tissues yields plasmids, which are identical to the chloroplast transformation vector in size and restriction pattern. As the transformation vector contained an integration cassette, integration of sequences into the plastome at the predicted sites was shown by Southern analysis as well as the presence of plasmid-like molecules. Southern analysis revealed increased copy number of the plasmids compared to the copy number of the plastome molecules.

The sequences responsible for the maintenance of the extra-chromosomal plasmids could be identified. Surprisingly, it was found that the sequences, which appeared to be essential for long-term maintenance, did not contain any known plastid replication origin sequences. We used vectors do not carry any terminator or 3'-UTR structures, thus creating long polycistronic transcription units.

The Novel Vectors of This Invention Enable Polycistronic Expression of Genes

The vectors described in this invention do not contain transcription termination and/or initiation sequences for the plasmid-encoded genes. Preferably, they lack terminator sequences. Several genes may be transcribed from one functional promotor as an artificial operon. To ensure an effective translation of every single sequence of interest of the polycistronic transcript adequate ribosome binding sites are preferably inserted into the spacer elements separating the respective sequence of interest. The cloning effort for the construction of the expression cassettes is substantially reduced. Moreover, as the extra-chromosomal elements are circular, continuous transcription can occur ("rolling-circle"-like), allowing higher expression levels of sequences of interest.

Surplus Stretches of Homology Lead to Genetic Instability—the Novel Vectors of This Invention Avoid Surplus Homologous Sequences Homologous sequences required for expression of transgene(s) may cause genetic instability, particularly as long as transformed and untransformed plastomes coexist inside the same organelle (Eibl et al., 1999).

The novel vectors consist of fewer elements than conventional plastid transformation vectors. As a consequence, due to the use of less homologous sequences, this invention allows more stable plastid modifications, such that they can be functionally inherited and can be incorporated in stable cell lines and plants. This strategy is also applied to the "removable shuttle" vectors containing integration cassettes (see below).

The Novel Vectors of This Invention Show Increased Copy Numbers

Gene expression is influenced by a vast number of parameters including promoter strength, RNA-stability, translation efficiency and protein turnover. Another important parameter is the copy number of the coding DNA sequence. A linear dependence between copy number and expression may be assumed to a certain degree. The plasmids used in this invention show significantly increased copy numbers compared to the plastome molecules (2-5-fold increase). Consequently, these plasmid vectors provide an optimal basis for extremely high transgene expression levels in plastids. Very high expression levels of recombinant genes may be extremely useful for a number of applications, such as for the production of protein-based pharmaceutical substances, biodegradable raw materials or any other protein in the plastid compartment. Making use of both strong regulatory elements and high copy number, extra-chromosomal plasmids in plastids may lead to extraordinary high concentrations of foreign protein(s) which cannot be achieved by conventional plant transformation methods.

Novel Vectors of This Invention are Not Species Specific

Conventional chloroplast transformation vectors contain chloroplast genome sequences isolated from the target plant species to serve as homologous flanks for integration of the trangenes via homologous recombination. Usually the expression cassette(s) are flanked by two plastome sequences from the desired integration site. The plastomes of different species show significant variations in both general structure and sequences imposing the need on the design of transformation vectors to use species-specific flanks. Moreover, the plastid DNA sequence and gene arrangement of most plant species is not known yet. This requires additional effort during the construction of cloning transformation vectors for various plant species. The novel method described in this invention—at least in some embodiments —circumvents the need to clone flanks for the stable insertion of the transgene. Also, integration into plastid DNA may result in unwanted effects on plastid gene expression, even if so-called intergenic sequences are targeted which may contain regulatory elements.

The Novel Plastid Transformation Method Described Herein Combines Several Advantages In some embodiments, the invention describes the use of a new plastid transformation method using vectors, that (1) do not essentially contain plastid flanks for homologous recombination, that (2) allow unusual high expression levels by increasing the copy number of the DNA-template AND by making use of a "rolling-circle like" polycistronic transcription without terminator elements, and that (3) circumvent the occurrence of marker genes in the transgenic plants at least in some of the embodiments.

The teaching of this invention may be used to produce plant cells and plants having stably or non-stably transformed plastids. Plastids of many different plant species may be transformed. The invention is applicable to monocots and dicot plants. Crop plant are particularly preferred. Examples of such crop plants are maize, rice, wheat, oat, rye, barley, soybean, tobacco, tomato, potato, grape, peanut, sweet potato, alfalfa, sorghum, pea, and cotton.

Generation of Transplastomic Plants Devoid of a Selection Marker

One major criticism on plant biotechnology is the presence of—mostly bacterial—antibiotic marker gene(s) in the transformed plants. There are concerns that uncontrolled release of such genes into the environment could either appear through undesired outcrossing to wild type species or via horizontal gene transfer mediated by soil bacteria. Although the first scenario (outcross) is unlikely to happen with the predominantly maternally inherited plastome trangenes, the later (horizontal gene transfer) cannot absolutely be excluded. It is therefore highly desirable to establish methods for gene transfer, that result in antibiotic marker-free transgenic plants. One possibility to achieve this goal was previously demonstrated by (Iamtham and Day, 2000) who could show that it is possible to remove an antibiotic marker from plastome transformants by screening for excision events mediated by repeated elements on the transformation vector. In this invention, several different procedures yielding transplastomes which do not contain an antibiotic selection marker are described.

Figure 2:
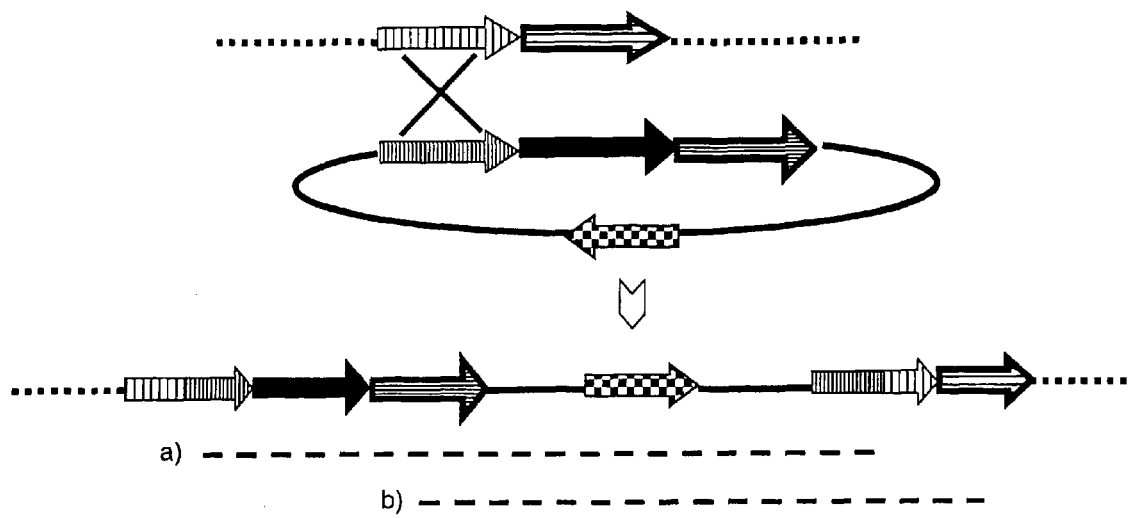
Figure 2:
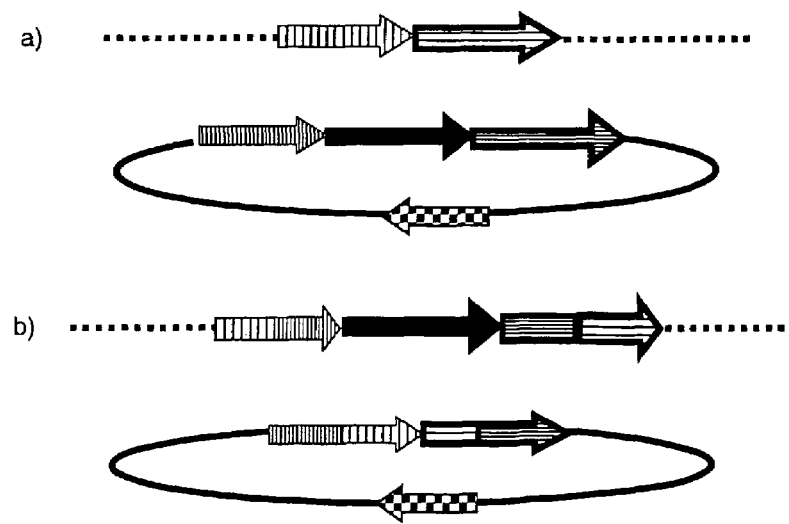

A preferred embodiment of the process of generating selection marker-free transgenic plants comprises stable insertion of one or more sequence(s) of interest into the plastome. Transformation vectors designed for this application contain the sequence of interest flanked by plastid DNA sequences, as in conventional plastid transformation vectors. In contrast to these, however, the selection marker sequence is located outside of the flanking plastid DNA sequences (FIG. 2). Double reciprocal recombination in both flanks would allow insertion of only the sequence(s) of interest into the plastome; cells containing such plastomes can, however, not be selected, since they do not contain the selection marker. Therefore, in said process of generating transgenic plants, this invention makes use of transient plastome integration of the selection marker. Non-stable integration of the selection marker is provided when the complete transformation vector sequence is integrated into the plastome via a single region of homology. We were able to show that integration of the complete transformation vector occurs with a very high frequency by analyzing plastomes transformed with conventional transformation vectors (example 1). This finding provides a model for the technique utilized in this invention: as maintenance of the selection marker is preferably achieved exclusively by integration of the complete transformation vector sequence via a single recombination event (FIG. 2), this recombination event is selected for by keeping cells or tissue under selection pressure after application of the transformation vector; only cells containing the selection marker are able to proliferate and produce cell lines or plant regenerates. Thus, the sequences of the vector responsible for integration confer replication to the vector, notably via transient integration into the plastome. In plastome molecules showing integration of the complete transformation vector, the sequences used as homologous flanks in the vector are present twice in close vicinity (one copy each from the transformation vector and the original plastid DNA sequence, compare FIG. 2). This causes an instable situation, as the very active recombination system of the chloroplast will lead to homologous recombination between the repeated sequences; such recombination events lead to excision of the selection marker sequence from the plastome. Therefore, once a primary transformant with plastomes containing the complete transformation vector sequence is established, selection pressure is removed in order to allow proliferation of plastomes showing the second recombination event. Two possibilities of recombination can occur (FIG. 2): recombination between the two copies of the plastid sequence which was the site of the first recombination event (where the transformation vector was integrated) leads to reversion of the first recombination, i.e. excision of the complete transformation vector. Thereby the original plastome sequence is restored and indirectly replicated vector is produced. However, a second possibility exists, wherein recombination between the two copies of the second flank occurs. This second recombination event leads to excision of the vector sequence including the selection marker, whereas the sequence(s) of interest remain(s) within the plastome at the targeted site between the two flanks. By regeneration of cells with such plastomes, plants containing any desired modification of the plastome, but being devoid of selection marker genes can be generated. Random segregation of plastomes during plastid and cell division leads to sectors containing only one type of plastome (homoplasmic sectors), which can be characterized by molecular analysis and used for regeneration of plants. If the two plastid DNA flanks are of about the same size, as is the case in the transformation vectors described here, and as is generally the case in conventional transformation vectors, the two possibilities of recombination events occur with roughly the same probability. Therefore, about 50% of analyzed sectors will contain the desired plastome, which allows efficient identification. For increased efficiency, this invention further describes techniques which allow visual identification of cells containing the desired plastome (see below).

A further embodiment of this invention provides a technique where transient integration of the selection marker can occur at an additional site different from the integration site of the gene of interest. For this purpose, the transformation vector contains an additional integration sequence homologous to plastid DNA, providing a further site for recombination with the plastome for integration of the complete transformation vector. Copies of the selection marker which are integrated at the second targeting site (said additional integration sequence) may provide resistance during selection. Therefore, at the first targeting site (e.g. said sequences flanking said sequence of interest), stable integration of the sequence of interest can occur without marker integration. In addition, the integrated copy of the transformation vector can provide a long-time source for an integration cassette of the sequence(s) of interest. Selection can be sustained until a sufficient number of plastomes shows stable integration of the sequence of interest. Upon release of selection pressure, the non-stable integration of the transformation vector at the second targeting site is lost. Due to the two different targeting sites (first targeting site: said sequences flanking said sequence of interest; second targeting site: additional integration sequence), this excision does not concern the stably integrated sequence(s) of interest. Applications of this embodiment are described in examples 3 and 4.

The principle of utilizing recombination of sequences of said DNA (the transformation vector) with sequences of the original plastome in order to remove sequences which are no longer needed is completely novel. In contrast to the method described by Iamtham and Day (2000) (WO0181600), where short sequence repetitions flanking the selection marker on the transformation vector were used to mediate marker excision after plastome integration, the principle described herein allows much longer regions of homology; therefore, recombination can occur with much higher probability (Maliga et al., 1993; Zoubenko et al., 1994). In addition, loss of the selection marker happens after successful plastome integration, notably exclusively after successful plastome integration, as the second region of homology is located on the plastome.

Generation of Plastome Mutants Devoid of Selection Marker

This invention can also be applied in cases where no sequence of interest is to be inserted into the plastome, e.g. for the generation of plastome deletion mutants devoid of selection marker genes. In this case, two plastid DNA sequences which flank the sequence to be deleted in the plastome are located on the transformation vector in direct vicinity. While in conventional deletion vectors the sequence to be deleted is replaced by the selection marker, in our system the selection marker is not flanked by plastid DNA sequences. The generation of marker-free mutants may be achieved by the same principle as described above using transient integration of the selection marker: primary transformants are established under selection pressure and therefore contain plastomes showing integration of the complete transformation vector due to a first recombination event via one of the flanking plastid DNA sequences. After removal of selection pressure, a secondary recombination event between the two copies of the second plastid DNA segment leads to excision of the vector sequence with the selection marker. This technique allows genuine deletion rather than replacement of plastome sequences. In addition, as the mutant plant does not contain the selection marker, further transformations can be made with the same selection marker. Moreover, the same technique can further be used to introduce modifications of existing plastome sequences like amino acid changes or modified regulatory elements.

An endogenous plastid gene which is directly or indirectly functionally involved in photosynthesis may be used as selection marker. An example for a gene directly involved into photosynthesis is petA which is essential for photosynthetic electron transport (an example for a gene indirectly involved into photosynthesis is rpoA, which encodes for the plastid encoded RNA-polymerase. Knock-out mutants of rpoA are not able to perform photosynthesis, because transcription of genes directly involved in photosynthesis is blocked). In a first step, the photosynthesis-relevant gene may be interrupted. This material is then used as a recipient line for a second plastid transformation, in which selection for plastids containing the transformation vector is achieved by using the restored photosynthetic function as a marker. This novel type of "marker" is not flanked by any homologous sequences for integration, but remains in the plastids on a preferably autonomously replicating plasmid. As photosynthesis is essential for plants growing on soil, there is constant selection for the maintenance of the plasmid carrying the photosynthesis relevant function. The respective photosynthetic gene is not fused to a terminator element in order to enable transcription of one or more gene(s) of interest and in order to achieve a very high expression level via "rolling-circle-like" transcription.

Another procedure (cf. example 11) uses an autonomously replicating plasmid as a shuttle vector which mediates integration of the gene(s) of interest, but not of the selection marker. The selection marker remains on the autonomously replicating plasmid vector, as it is not flanked by homologous sequences. When removing the selection pressure after the transformed plant material has reached the homoplastomic state, the vector is lost, whereas the gene(s) of interest is stably integrated into the plastome. This procedure is based on modified sequences conferring autonomous replication, as a complete element would mediate an undesirable high replication frequency. A replication frequency, which exceeds the frequency of the plastome replication leads to the stabilization of the plasmids even in the absence of selection pressure (such a high replication frequency is mediated by the elements conferring autonomous replication described herein). Consequently, loss of the plasmid in the absence of selection pressure is preferably achieved by using deletion-mutants of the described sequence elements, leading to a reduced replication speed.

A variant of this methods allows for the generation of selection marker-free transformants even if elements mediating a very high replication frequency are used: The marker cassette—e.g. the aadA-gene in example 11—is flanked by a direct repeat of sequences, which are non-homologous to the plastome. In example 11, the direct repeat is included in the vector by a sequence element originating from the bacterial vector. Homologous recombination will lead to excision of the marker gene from the shuttle plasmids. This procedure shows some similarities to the marker removal described by Iamtham and Day (2000). In contrast, however, the marker gene is not removed from the plastome after an integration event, but it is excised from an autonomously replicating plasmid.

Visual Identification of Desired Transplastomic Material by Insertion of Additional Sequences This invention further provides techniques for more efficient identification of transformants generated by the method of transient marker integration. One possibility is the insertion of a sequence that allows visual identification of transformants. An example for such a sequence is a sequence encoding Green Fluorescent Protein (GFP) that can be expressed in plastids, as described in example 6. This sequence is inserted in the transformation vector between the plastid DNA flanks along with the sequence(s) of interest and can therefore become stably integrated into the plastome. As plastids expressing GFP show green fluorescence (Khan and Maliga, 1999; Sidorov et al., 1999), cells or sectors containing such plastids can be readily identified. If the secondary recombination event removes the complete transformation vector sequence, also the GFP coding sequence is removed, and sectors containing such plastomes do not show fluorescence anymore. In contrast to this, plastomes showing the desired secondary recombination event (excision of the vector sequence with the selection marker, but integration of the sequence(s) of interest), still cause a fluorescent phenotype. Thus, identification of selection marker-free transplastomic cells or tissue is greatly simplified. This procedure can be performed with any sequence allowing visual identification of sectors containing said sequence. Since genes like the GFP gene do not give a selective advantage to transformed material, the risk of uncontrolled spreading by horizontal gene transfer is greatly reduced. Moreover, such genes do not contain any foreseeable risk to humans, other organisms, or the environment in general, in case of uncontrolled spreading.

Visual Identification of Desired Transplastomic Material by Restoration of a Mutant Phenotype In addition to this, the invention also provides a method where the only foreign sequences remaining in the transplastomic plant are the sequence(s) of interest. This method is based on a two-step procedure, requiring two transformations. In a first step, a plastid mutant showing a readily distinguishable phenotype is produced. Preferably, this phenotype is caused by altered pigmentation. Examples for such mutants are plants deficient in rpoA gene function, showing a white phenotype (see example 5), or plants deficient in petA gene function, showing a pale green phenotype accompanied by high chlorophyll fluorescence (hcf) (see example 2). Further examples include inactivation mutants of ycf3 (example 3), and ycf9, respectively. Disruption of the gene function can for instance be achieved by disruption or deletion of the gene or parts of it. Generation of such a mutant is preferably achieved by plastid transformation using the method of transient selection marker integration as described above, resulting in plants devoid of selection marker. The mutant phenotype of cells allows visual identification of desired plant material after segregation without selection. Material obtained from such a mutant plant can now serve as a substrate for a second transformation, where one or more sequence(s) of interest are introduced into the plastome. Transformation vectors for this purpose have the same structure as described above in this invention, but in addition contain a sequence which restores the disrupted gene function of the mutant. This restoring sequence may be inserted in the transformation vector between the plastid DNA flanks along with the sequence(s) of interest, while the selection marker sequence is outside of the flanks. Cells containing transformed plastomes can easily be identified, as they show the wild-type phenotype. If the complete transformation vector is excised by a secondary recombination event, the mutant genotype is formed again, so that sectors containing such plastomes show the mutant phenotype. In contrast to this, plastomes showing the desired secondary recombination event (excision of the vector sequence with the selection marker, but integration of the sequence(s) of interest), have the wild-type phenotype, which simplifies the identification of tissue with the desired transplastome. In addition, transplastomic plants produced by this method do not contain any additional sequences apart from the desired sequence(s) of interest. Once a plastome mutant appropriate for this method has been generated, it can be propagated and used for introduction of any desired sequence of interest; therefore, this method does not require two transformations for every new sequence of interest, but the desired transplastomic plant can be generated in a single transformation step.

Process of Using aphA-6 for Plastid Transformation of Higher Plants

So far, aadA and nptII are the only selection marker genes that can be routinely used for plastid transformation of higher plants. Therefore, there is a need for further selection markers for plastid transformation of higher plants.

This invention solves this problem by providing a process of generating a transgenic multi-cellular multi-plastidal plant or cells thereof transformed in their plastomes by the following steps:
(a) transforming plastids of cells or protoplasts of said multi-cellular plant with a DNA comprising as selectable marker a sequence coding for bacterial aminoglycoside phosphotransferase A-6 (aphA-6);
(b) allowing propagation of said transformed cells or protoplasts under conditions of exposing said propagating cells or protoplasts to an aminoglycoside antibiotic at a predetermined concentration;
(c) allowing for segregation of transformed and non-transformed plastomes as well as for segregation of transformed or non-transformed plastids during repeated cycles of regeneration under conditions of exposing to an aminoglycoside antibiotic at a predetermined concentration; and
(d) recovering cells and/or plants being genetically transformed in their plastomes.

This process is preferably performed in combination with PEG-mediated transformation of protoplasts of higher plants. The above process is applicable to all multi-cellular multi-plastidal plants or cells thereof. *Nicotiana* species are most preferred.

The gene aphA-6 is derived from *Acinetobacter baumanii* (Bateman and Purton, 2000; Martin et al., 1988). It has been been previously used for plastid transformation of the unicellular alga *Chlamydomonas reinhardtii* (Bateman and Purton, 2000). It has now been surprisingly found that aphA-6 can be used for plastid transformation of higher plants if an elaborate selection protocol with well-controlled antibiotic concentrations as disclosed herein are used. As antibiotics, aminoglycoside antibiotics are used. The most preferred antibiotic is kanamycin.

The aminoglycoside antibiotic concentration, notably the kanamycin concentration, to be used in this process are 20 to 500 µg/ml, preferably, 25 to 250 µg/ml, more preferably 50 to 200 µg/ml depending on the transformation method (cf. example 12).

Herein, said the nucleotide sequence of *A. baumanii* may be use. Further, sequences coding for the same amino acid sequence of aphA-6 of *A. baumanii* according to the degeneracy of the genetic code may be used. Also, nucleotide sequences coding for aphA-6 variants having at least 50%, preferably 75% sequence homology to the *A. baumanii* aphA-6 amino acid sequence may be used. Most advantageously, nucleotide sequences coding for aphA-6 variants having at least 50%, preferably 75% sequence identity to the *A. baumanii* aphA-6 amino acid sequence are be used. Additionally, sequences hybridising to the *A. baumanii* aphA-6 coding sequence under conditions of medium, preferably of high stringency conditions may be used.

The aphA-6 gene like nptII gene (aphA-2) encodes an enzyme which belongs to the aminoglycoside phosphotransferase family originating from different prokaryotic organisms (Shaw et al. 1993, Wright and Thompson 1999). Both enzymes have a similar catalytic activity, but the aphA-6 gene product is distinguished by having an extended resistance profile, being able not only to detoxify kanamycin and other common aminoglycosides but also others such as amikacin.

Herein, we show (example 12) that the aphA-6 is a versatile, efficient and reproducible marker for plastid transformation in higher plants, notably in tobacco. Even though the overall transformation efficiency using the aphA-6 gene is below that routinely obtained with the aadA gene, it is sufficiently high for routine production of transgenic plastid transformants. Published results from leaf bombardment with aadA constructs are in the range of 0.5-5 transformants per shot. Using the aphA-6 gene with grid bombardment we obtained 1 transformants from every 2 shots. The transformation efficiency with PEG transformation and the aadA gene is in the range of 10-40 transformants per $0.5 \times 10^6$ treated protoplasts (Koop et al. 1996, De Santis-Maciossek et al. 1999), whereas we obtained around 5 transformants from every PEG transformation. In contrast, with nptII only 1 plastid transformant was obtained from every 25 leaf bombardments. Furthermore, numerous nuclear transformants were found in the regenerated lines with nptII, whereas herein, with aphA-6, 29 of the 30 PCR-tested lines were positive plastid transformants and no nuclear transformants were detected. This improved efficiency is totally surprising. Factors contributing thereto include the use of a more stringent selection system, protoplast-derived target tissues and an alternative kanamycin-detoxifying enzyme.

For the first time we have established a useful additional antibiotic plastid marker to the universally used aadA gene. Another important aspect of our work is the description of 3 new insertion sites for tobacco plastome. In two cases a chimeric aphA-6 expression cassette was introduced neutrally into intergenic regions between the genes trnR-trnN and petA-orf99, respectively. In the third case, the aphA-6 coding region was introduced in front of the ycf3 coding sequence generating an artificial operon such that both genes are finally under the control of ycf3 regulatory elements.

Variations in kanamycin resistance were observed in plants containing the aphA-6 gene under the control of different plastid promoters. The upper limits of tolerance were 500 mg/l and 50 mg/l kanamycin, respectively, for transformants containing the aphA-6 gene under the control of the 16S rRNA promoter or the ycf3 regulatory elements. In contrast, the T1 progeny obtained from plants carrying the newly created aphA-6-ycf3 operon were able to germinate normally on 200 mg/l kanamycin. Possible explanations for this apparent discrepancy on kanamycin, between explants and seedlings, are physiological differences in kanamycin uptake or variations in expression of the aphA-6 gene from the ycf3 regulatory elements.

Herein, it is shown that the aphA-6 gene can be used as a new dominant selection marker for plastid transformation in higher plants. An additional flexible marker should prove useful for plastid engineering strategies, particularly where stepwise plastome insertion of foreign genes in combination with marker recycling is required.

EXAMPLES

Example 1

Figure 3:
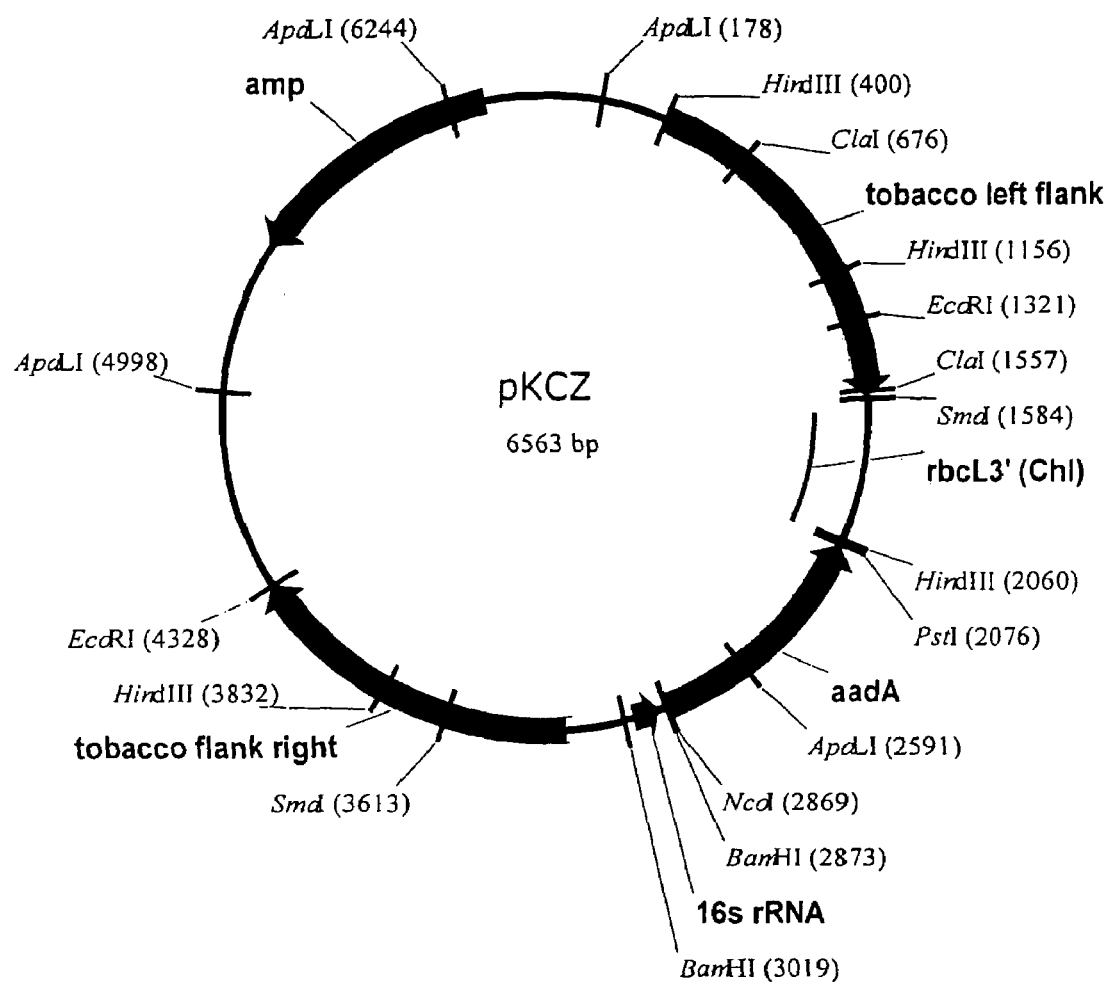

PCR Analysis of Complete Vector Integration (Via One Flank) Into the Plastid Genome Plastid Transformation Vector PKCZ pKCZ is a conventional plastid transformation vector where the selection marker is cloned between the two flanks used for homologous recombination. The vector is designed to make a neutral insertion between trnR and trnN in the inverted repeat region of the tobacco plastid genome (Zou, 2001). pKCZ comprises two flanking sequences for homologous recombination (corresponding to *Nicotiana tabacum* plastome sequences 31106-132277 and 132278-133396, according to GenBank accession number Z00044) and an aadA plastid expression cassette under control of the 16s rRNA promoter (Koop et al., 1996). A schematic drawing of the plasmid construct is shown in FIG. 3.

Generation of Primary Transformants and Subsequent Selection for Homoplastomic Lines Particle gun-mediated plastid transformation and subsequent selection were carried out as in example 3. Selection of transformants was based on the resistance to the antibiotics spectinomycin/streptomycin, conferred by the aadA gene product. In order to amplify transformed plastid genomes and to eliminate wild-type genomes, the primary transformants (cycle-0) were subjected to several additional rounds of regeneration (from small leaf explants) on selective media containing spectinomycin (here designated as cycle-I, cycle-II etc).

Analysis of Primary Transformants by PCR

Plastid transformants (cycle-0) were identified by PCR using total DNA isolated with the DNeasy Plant Mini Kit (QIAGEN, Hilden, Germany). To determine the presence of the aadA gene the primers oSH81 (SEQ ID:3)(5'-CTATCA-GAGGTAGTTGGCGTC-3') and oFCH60 (SEQ ID NO:4) (5'-CACTACATTTTCGCTCATCGCC-3') were used. The PCR program was as follows: 3 min at 94° C., 1 cycle; 45 sec at 94° C., 45 sec at 55° C., 2 min at 72° C., 30 cycles; final extension at 72° C. for 10 min. The results showed that 48 lines from 54 analysed (6 bombarded leaves) gave the expected amplification product of 504 bp. To prove correct integration of the aadA cassette within the tobacco plastome primers oSH58 (SEQ ID NO:5)(5'-TATTCCGACTTC-CCCAGAGC-3') and oFCH60 (SEQ ID NO:4)(5'-CACTA-CATTTCGCTCATCGCC-3') were used. Primer oSH58 is located outside (downstream) of the right flank of pKCZ in the tobacco plastome and in combination with oFCH60 can only give the expected product of 2106 bp upon integration of the aadA expression cassette between trnR and trnN in the inverted repeat. The PCR program was as follows: 5 min at 94° C., 1 cycle; 45 sec at 94° C., 45 sec at 55° C., 3.5 min at 72° C., 35 cycles; final extension at 72° C. for 7 min. All 48 of the aadA PCR positive lines showed the expected right-flank-aadA product of 2106 bp.

Ten of the cycle-0 transformants (1:1, 1:2, 1:3, 1:4, 1:5, 2:1, 2:4, 2:5, 2:6 and 2:7) were selected for further analysis.

PCR Analysis of Transformants Containing Completely Integrated Vectors

Figure 1:
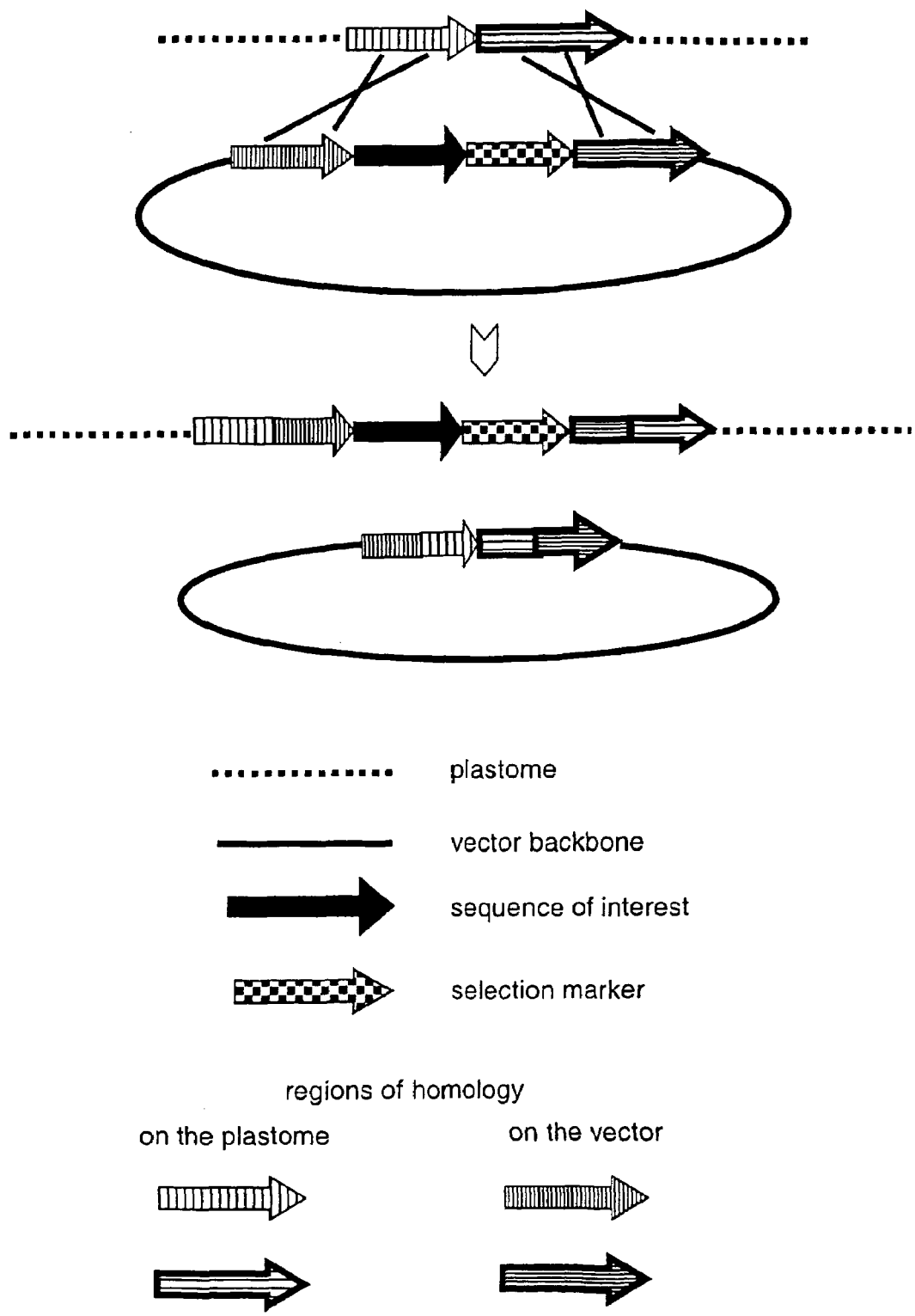
Figure 4:
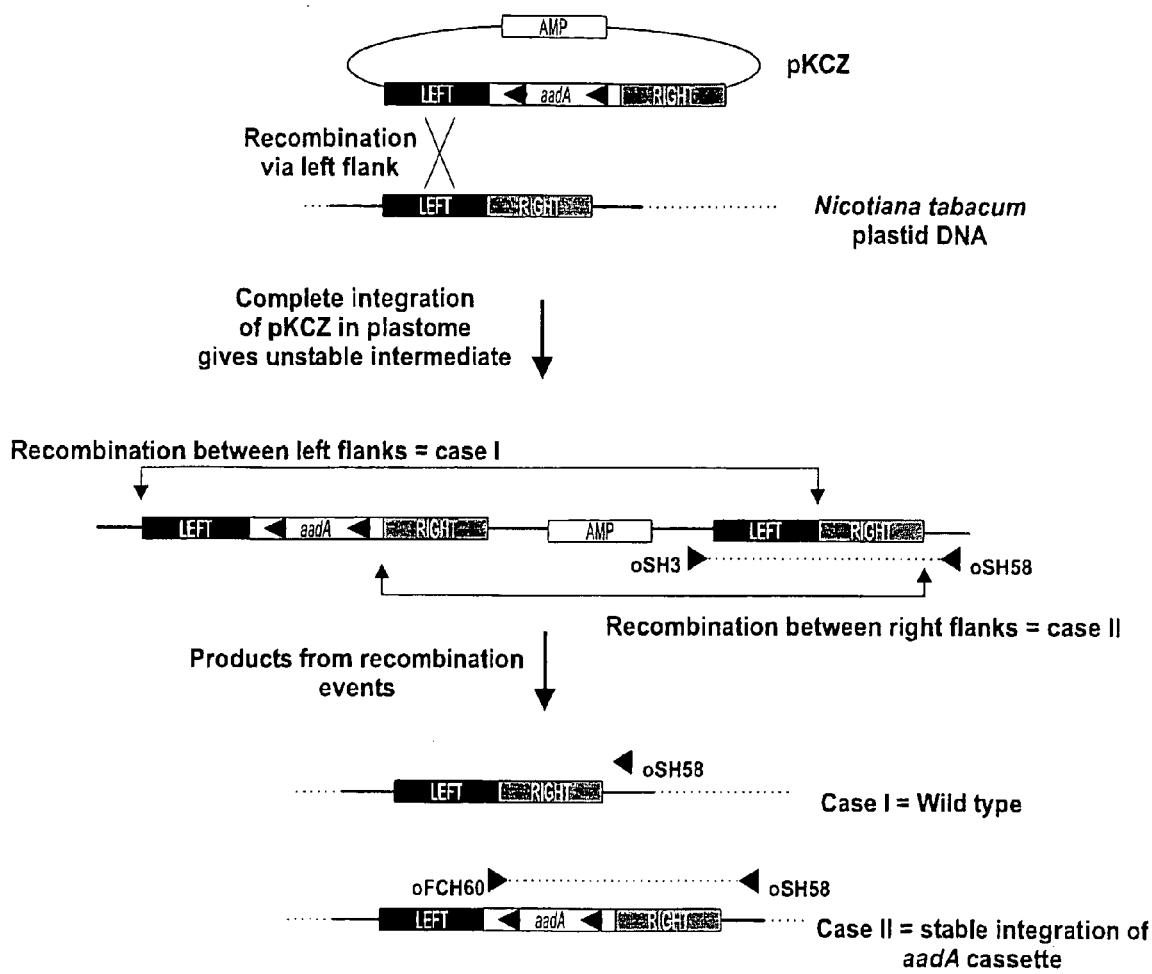
Figure 5:
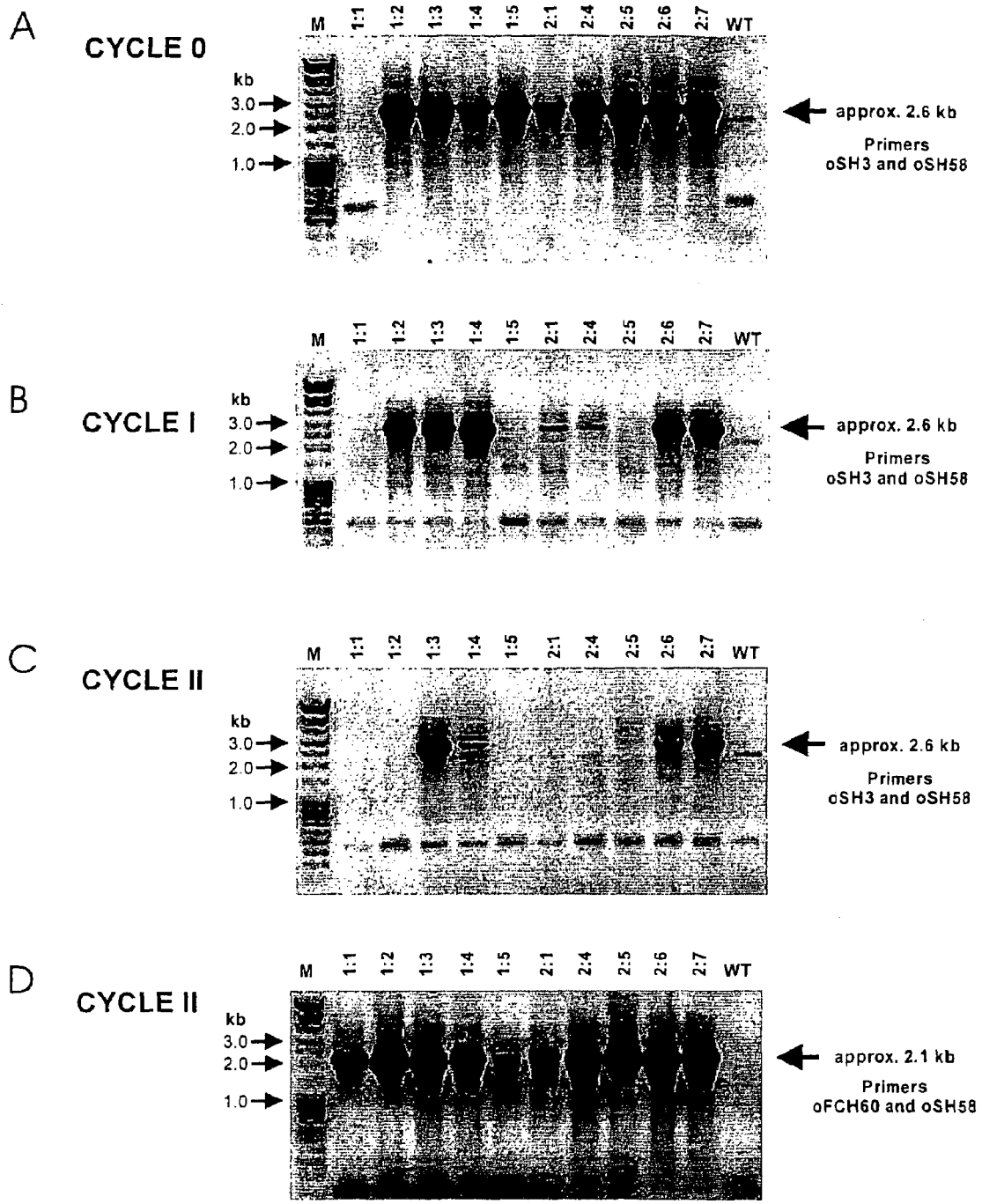

Normally, the production of stable plastid transformants is thought to occur via two simultaneous recombination events occurring between the left and right flanks of the transforming molecule and the plastome (as depicted in FIG. 1). An alternative mechanism is presented in FIG. 4 using the conventional plastid transformation vector pKCZ as an example. Here, complete integration of the pKCZ vector occurs first, via recombination with one flank only (either left or right) with the plastome, resulting in the generation of a hypothetical unstable intermediate. Subsequent additional recombination events can then take place between the duplicated flanks in this molecule to generate either the wild-type situation (case I) or a stably integrated aadA cassette (case II). In FIG. 4 only the situation resulting from recombination via the left flank of pKCZ is shown. However, a comparable situation can arise if the right flank is used for complete vector integration. In order to test for this possibility, PCR was performed using primers oSH3 (SEQ ID NO:6)(5'-GGCATCAGAGCAGATTG-3') and oSH58 (SEQ ID NO:5) (5'-TATTCCGACTTCCCCAGAGC-3'). Primer oSH3 is located within the vector backbone of pKCZ (pUC18) and primer oSH58 is located outside (downstream) of the right flank of pKCZ in the tobacco plastome. A product of 2638 bp can only be obtained with these two primers when complete pKCZ integration has occurred as shown in FIG. 4. No PCR product of the expected size will be obtained from the wild type plastome fragment (comprising left and right flanks) since the binding site for oSH3 is absent. The PCR program was as follows: 5 min at 94° C., 1 cycle; 45 sec at 94° C., 45 sec at 55° C., 3.5 min at 72° C., 35 cycles; final extension at 72° C. for 7 min. Nine of the 10 cycle-0 transformants analysed showed a PCR product of 2.6 kb which would be consistent with complete integration of pKCZ into the plastid genome within these lines (FIG. 5A). No product of the correct size was observed in the wild type control or in sample 1:1. Since complete integration of pKCZ results in the formation of an unstable intermediate it is to be expected that with increasing time additional recombination events between the duplicated flanks in this molecule will lead to either the wild-type situation (case I) or a stably integrated aadA cassette (case II). As such DNA samples prepared from cycle-I and cycle-II plant material were analysed by PCR with primers oSH3 and oSH58. If the model presented in FIG. 4 is correct the probability of amplifying the 2638 bp band with primers oSH3 and oSH58 should be reduced with each regeneration cycle on selection. The results suggest that this is indeed the case since only 5 of the 10 cycle-I lines analysed gave a strong PCR product of the expected size (FIG. 5B). Furthermore, in cycle-II the number of lines showing clear amplification of the expected 2638 bp band was further reduced.

The model presented in FIG. 4 also predicts that all cycle-II lines which are negative for complete vector integration should still show PCR signals consistent with a stably integrated aadA cassette (case II) due to the molecular rearrangements previously described. To prove integration of the aadA cassette within the tobacco plastome primers oSH58 (SEQ ID NO:5)(5'-TATTCCGACTTCCCCA-GAGC-3') and oFCH60 (SEQ ID NO:4)(5'-CACTA-CATTTCGCTCATCGCC-3') were used. The PCR program was as follows: 5 min at 94° C., 1 cycle; 45 sec at 94° C., 45 sec at 55° C., 3.5 min at 72° C., 35 cycles; final extension at 72° C. for 7 min. All 10 of the cycle-II transformants show the expected right-flank-aadA product of 2106 bp (FIG. 5D) which would be consistent with the case II scenario shown in FIG. 4.

Example 2

Construction of a Selection System Based on the Inactivation and Reconstitution of a Photosynthetic Gene Construction of Transformation Vector pICF558 for Inactivation of the Plastid petA Gene All cloning procedures were carried out using standard protocols as described in Ausubel et al., 1999.

Vector pICF558 comprises two flanking sequences (corresponding to Nicotiana tabacum plastome sequences 63335-64334 and 65598-66597, according to GenBank accession number Z00044) and an aadA-cassette (pUC16SaadA Sma vollst, Koop et al., 1996) in between. The homologous flanks for recombination are the 5' and 3' sequences of the petA gene, 1 kb each. The aadA-cassette replaces the petA gene (962 bp) and 300 bp of the petA 3' region.

Both flanking fragments were amplified by PCR using the following oligo pairs as primers: oSK13 (SEQ ID NO:7) (5'-GGAATTCCATATGGTATAAAACTCATGT-GTGTAAGAAA-3') and oSK14 (SEQ ID NO:8)(5'-TC-CCCCGGGGGTCCAATCATTGATCGCGAAA-3'), generating an NdeI and a SmaI site at the fragment ends, and oSK15 (SEQ ID NO:49) (5'-TTCCCCGGGTTCTAAATA-GAAAGMAAAG TCAAATTTG-3') and oSK16 (SEQ ID NO:3) (5'-CATGCATGCGAATGATAAGATTCTCT-TAGCTC-3'), generating a SmaI and a SphI site at the fragment ends. The PCR program used was as follows: 3 min at 94° C., 1 cycle; 45 sec at 94° C., 45 sec at 55° C., 1.5 min at 72° C., 30 cycles; final extension at 72° C. for 10 min. The digested fragments (left/right flank) and the aadA-cassette as SmaI fragment were cloned in one step into the pUC19 vector, which was opened with NdeI and SphI to give vector pICF558.

Construct pICF558 was analyzed by restriction digestion, and PCR-amplified fragments were sequenced to prove the correct sequence of the flanking regions.

Figure 6:
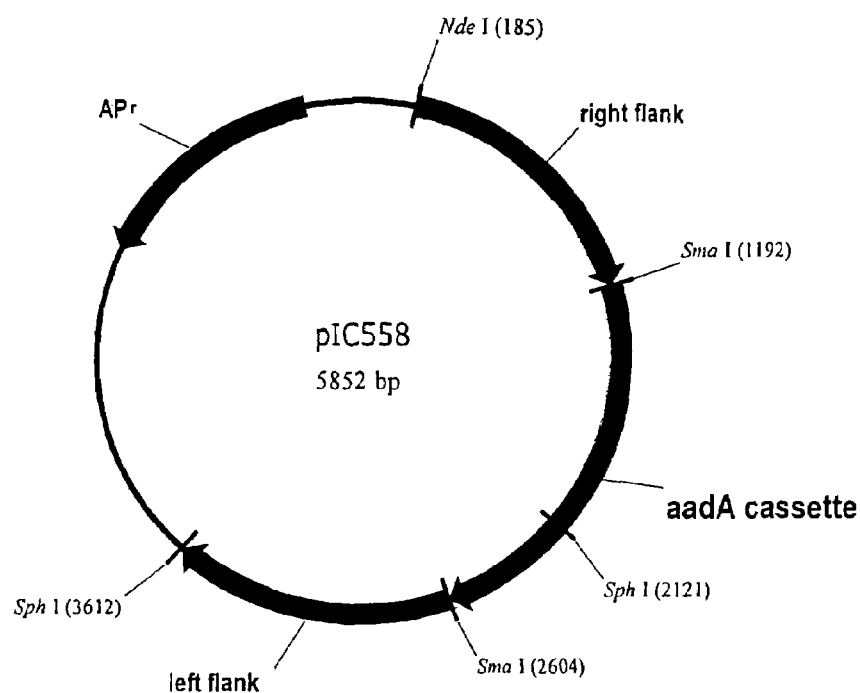
FIG. 6 shows a map of plastid transformation vector pICF558.
Figure 8:
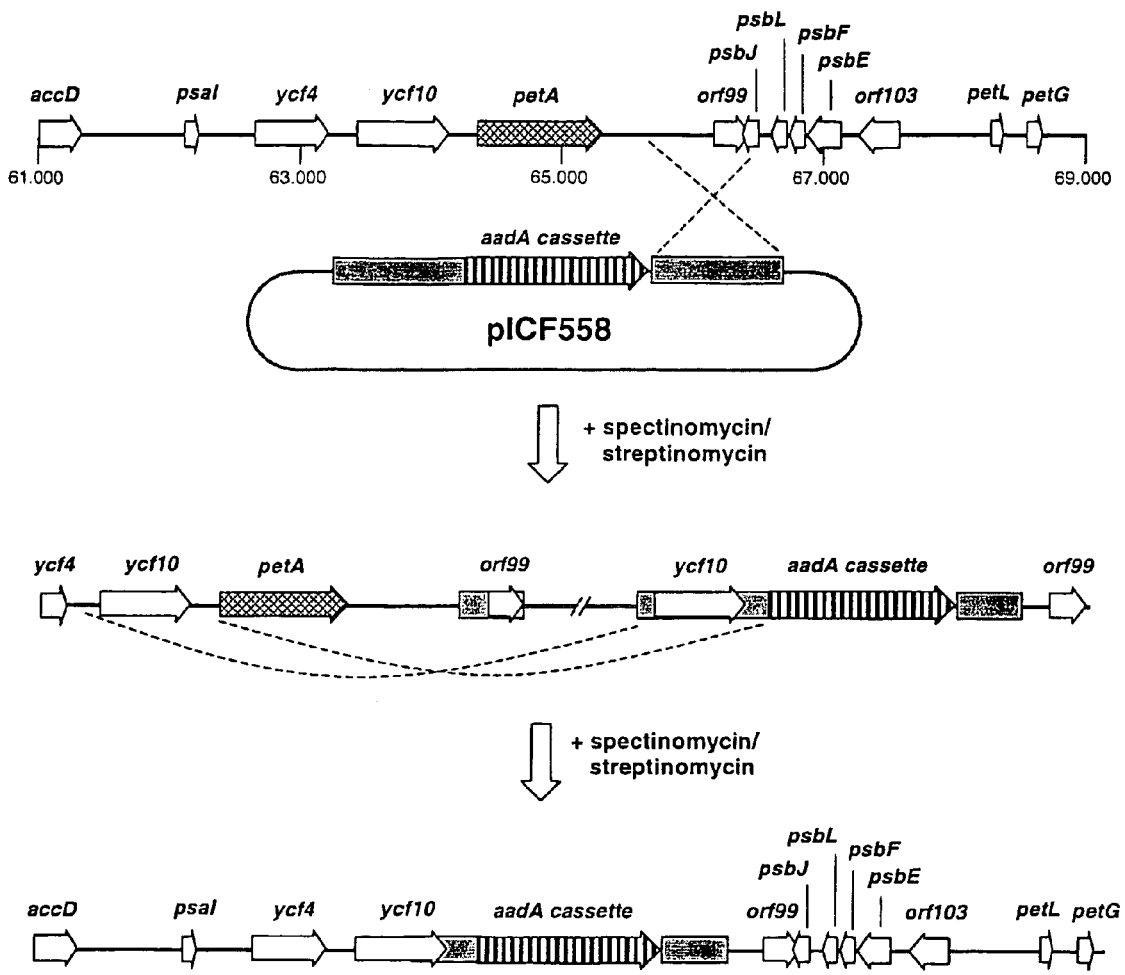
FIG. 8 shows a schematic drawing to illustrate plastid transformation using vector pICF558.

Transformation vector pICF558 is shown in FIGS. 6 and 8.

Construction of Transformation Vector pICF820

Vector pICF820 was constructed for the second transformation curing the deletion of the petA gene and simultaneously introducing a new gene of interest (uidA). Therefore, the petA coding sequence and a gene cassette (containing 5'/3' regulatory elements) were cloned in between the left/right flanking sequences (same as used for vector pICF558). Additionally, an aphA-6 expression cassette was cloned into the vector backbone for transient expression.

A fragment of ~2.2 kb containing 1 kb left flank, the petA gene sequence (962 bp) and 300 bp of the 3' region of the petA gene was amplified by PCR using the following oligo pair as primers: oSK13 (SEQ ID NO:7) (5'-GGAATTC-CATATGGTATAAAACTCATGTGTGTAAGAAA-3') and oSK71 (SEQ ID NO:10)(5'-TCCCCCGGGTAGAAAAC-TATTGATACGTCTTATGG-3'), generating an NdeI and a SmaI site at the fragment ends. The PCR program used was as follows: 3 min at 94° C., 1 cycle; 45 sec at 94° C., 45 sec at 55° C., 3 min at 72° C., 30 cycles; final extension at 72° C. for 10 min. This fragment and the right flank (same as in vector pICF558) were cloned together into an NdeI/SphI opened pUC19 vector to give vector pICF561. This vector comprises 1 kb left flank, the petA coding sequence, 300 bp of the petA 3' region and 1 kb right flank corresponding to Nicotiana tabacum plastome sequence 63335-66597 (GenBank accession number Z00044).

The gene of interest (uidA) was introduced as gene cassette (containing 5'/3' regulatory elements) between both flanking fragments, more precisely 300 bp downstream to petA coding sequence into the primer-generated SmaI site. The uidA-cassette was taken as SmaI fragment from vector pICF562 ('pUC16SRBSuidA3'rbcL', Koop et al., 1996) and cloned into the single SmaI site of vector pICF561 to give vector pICF597. The aphA-6 expression cassette was obtained as SmaI fragment from pICF599 (a preexisting derivative of vector pICF597 containing the aphA-6 coding sequence instead of the uidA coding sequence) and ligated into the blunted and dephosphorylated BgIII site in the backbone of vector pICF597 to give vector pICF820.

All constructs were analyzed by restriction digestion, and PCR-amplified fragments were sequenced to prove the correct sequence of the flanking regions.

Figure 7:
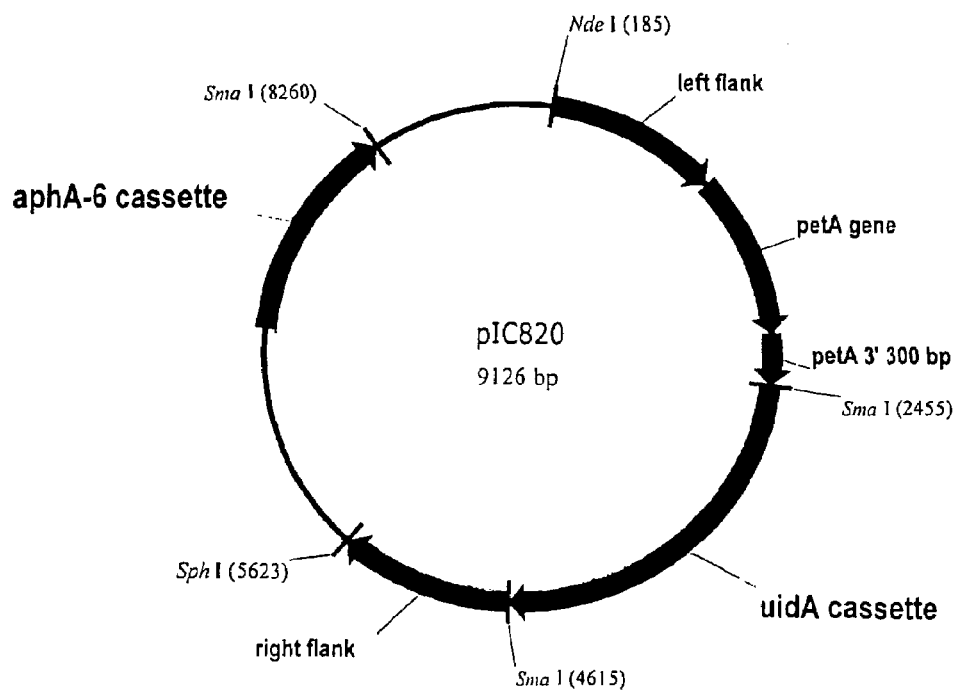
FIG. 7 shows a map of plastid transformation vector pICF820.
Figure 9:
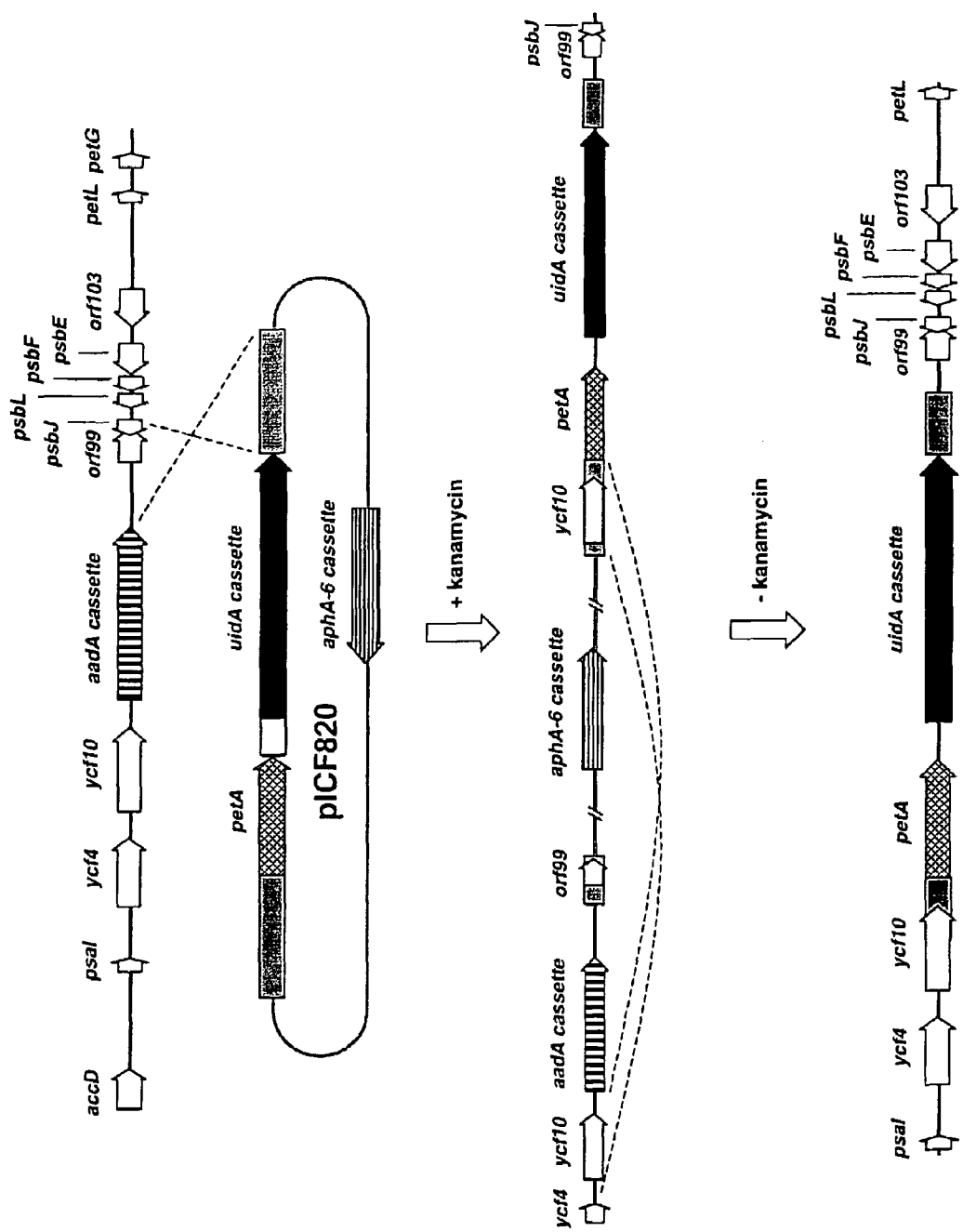
FIG. 9 shows a schematic drawing to illustrate plastid transformation using vector pICF820.

Transformation vector pICF820 is shown in FIGS. 7 and 9.

Primary Transformation and Selection of Homoplastomic ΔpetA Mutants

Plastid transformation by particle gun with vector pICF558 and selection were carried out as described in example 3. PEG-mediated plastid transformation with vector pICF558 and selection were carried out as described in example 3. Selection of transformants was done based on there resistance to spectinomycin/streptinomycin conferred by the aadA gene product.

Secondary Transformation and Selection of Homoplastomic Reconstituted Wild-Type Plants From ΔpetA Mutants Plastid transformation by particle gun with vector pICF820 was carried out as described in example 3. PEG-mediated plastid transformation with vector pICF820 was carried out as described in example 3. Selection of secondary transformants was done on kanamycin containing medium (25 mg/l) due to the transient expression of the aphA-6 gene in the transformed plastids (complete vector integration facilitates short-term expression of the kanamycin marker; see FIG. 9). In addition to the kanamycin resistance conferred by the aphA-6 expression, transformants display a dark-green, wild-type like phenotype showing the reconstitution of the petA gene. Dark-green regenerants were removed from selection medium and first shoots were transferred to B5 medium for rooting and plant development. Reconstituted lines develop normally on B5 medium, whereas ΔpetA mutants grow pretty poorly on B5 medium and do not root.

Analysis of Transformants by PCR and Southern Blot after Primary Transformation

For plant DNA isolation, PCR analysis and southern blotting standard protocols were used as described in example 3. To determine the presence of the aadA gene, primers oFCH59 (SEQ ID NO:11) (5'-TGCTGGCCGTA-CATTTGTACG-3') and oFCH60 (SEQ ID NO:12) (5'-CAC-TACATTTCGCTCATCGCC-3') were used. To prove the correct insertion of the aadA-cassette primers oFCH60 and oSK116 (SEQ ID NO:13)(5'-AATAGATTCATTAGTC-CGATACC-3') were used. Primer oSK116 is located upstream to the left flank. The PCR program used was as follows: 3 min at 94° C., 1 cycle; 45 sec at 94° C., 45 sec at 55° C., 2 min at 72° C., 30 cycles; final extension at 72° C. for 10 min. PCR results showed that 44 regenerated lines are carrying the aadA gene with correct plastome insertion (24 bombardments).

Additional analyses proved that for most ΔpetA lines it was possible to show the presence of the completely integrated transformation vector pICF558. This was done as well by PCR using primer combinations oSH2 (SEQ ID NO:14) (5'-CAGGAAAC AGCTATGACC-3'; located in the vector backbone) and oSK116 or oSH3 (SEQ ID NO:6) (5'-GGCATCAG AGCAGATTG-3', located in the vector backbone) and oSK253 (SEQ ID NO:15) (5'-GAC-TAGTCTAGAAA TTCATTTCGGCCAATTG-3'; located at the 3' end of the petA coding region). The PCR programs used were as follows: 3 min at 94° C., 1 cycle; 45 sec at 94° C., 45 sec at 55° C., 2,5 min at 72° C., 30 cycles; final extension at 72° C. for 10 min.

Further analysis by southern blotting showed whether the transformed lines were homoplastomic or heteroplastomic for the integration of the aadA cassette. DNA blot analysis was done as described in example 3: total plant DNA was NcoI or BglII digested, fragments gel-separated and blotted onto a membrane. For probing, DIG-labeled fragments (either left or right flank from the transformation vector) were used to distinguish between wild-type and transformed plastomes.

Analysis of Transformants by PCR and Southern Blot After Secondary Transformation For plant DNA isolation, PCR analysis and southern blotting standard protocols were used as described in example 3. To determine the presence of the uidA gene, primers oSM61 (SEQ ID NO:16) (5'-TCACACCGATAC-CATCAGCG-3') and oSM62 (SEQ ID NO:17) (5'-AT-TGTTTGCCTCCCTGCTGC-3') were used. To prove the correct insertion of the uidA-cassette primers oSM61 and oSK138 (SEQ ID NO:18) (5'-AATCGTACCAGTCTC-TACTGG-3') were used. Primer oSK138 is located downstream to the right flank. Reconstitution of the petA gene can be proven by PCR using primers oSK116 and oSM62 showing a PCR-amplified fragment containing sequences of the deleted petA gene/petA 3'UTR and new inserted uidA gene. The PCR programs used were as follows: 3 min at 94° C., I cycle; 45 sec at 94° C., 45 sec at 55° C., 2-3 min at 72° C., 30 cycles; final extension at 72° C. for 10 min.

Additional analyses proved that it was in most cases possible to show the complete integration of the transformation vector pICF820. This was done as well by PCR using again primer combinations oSH2/oSK116 or oSH3/oSK138. The PCR programs used were as follows: 3 min at 94° C., 1 cycle; 45 sec at 94° C., 45 sec at 55° C., 3 min at 72° C., 30 cycles; final extension at 72° C. for 10 min.

Further analysis by southern blot showed whether the transformed lines were homoplastomic or heteroplastomic. DNA blot analysis was done as described in example 3: total plant DNA was NcoI or BglII digested, fragments gel-separated and blotted onto a membrane. For probing, DIG-labeled fragments (either left or right flank from the transformation vector) were used to distinguish between wild-type and transformed plastomes.

Example 3

Inactivation/Reactivation of ycf3 and Stable Introduction of a Gus Gene by Transient Selection for a One Flank Mediated Integration of the aphA-6 Gene ycf3 has recently been shown to be required for stable accumulation of the photosystem I (PSI) complex in tobacco (Ruf et al., 1997). Disruption of this gene leads to a conditional pigment-deficient phenotype in the light. Homoplasmic Δycf3 plants displayed a complete white phenotype upon regeneration on drug- and phytohormone-free medium under standard light conditions (3.5-4 W/m$^2$), while the phenotype was much less severe (light green) under low light conditions (0.4-0.5 W/m$^2$).

Construction of Transformation Vector pICF577 for Targeted Inactivation of the ycf3 Gene A transformation vector, designed to inactivate the ycf3 gene by replacing the first exon and the splicing site of ycf3 (corresponding to plastome nucleotides 46042-46206, position numbers according to GenBank accession number Z00044.1) with the aadA coding region, was constructed. This vector does not contain any 3' regulatory elements (neither for the aadA marker gene, nor for the endogenous ycf3 or tRNA gene). In addition, no promoter elements were introduced, and the aadA gene is expected to be transcribed and translated by the endogenous ycf3 upstream regulatory element.

This vector contains the aadA coding region, flanked by 5'- and 3'-homologous sequences, which were amplified from the tobacco chloroplast genome by PCR using the following two pairs of primers: oFCH76 (SEQ ID NO:19) (5'-Nco I-GTA GCA ATC CAT TCT AGA AT-3', annealing with plastome nucleotides 46269-46288) and oFCH77 (SEQ ID NO:20) (5'-Sma I-CGG AAA GAG AGG GAT TCT AAC-3', annealing with plastome nucleotides 47205-46185); oFCH78 (SEQ ID NO:21(5'-Sph I-GAA GTT TCT TTC TTT GCT ACA-3', annealing with plastome nucleotides 45033-45053) and oFCH79 (SEQ ID NO:22)(5'-PstI-TAC GCT TTT T GA AGG TGA AGT-3', annealing with plastome nucleotides 46041-46021).

Figure 10:
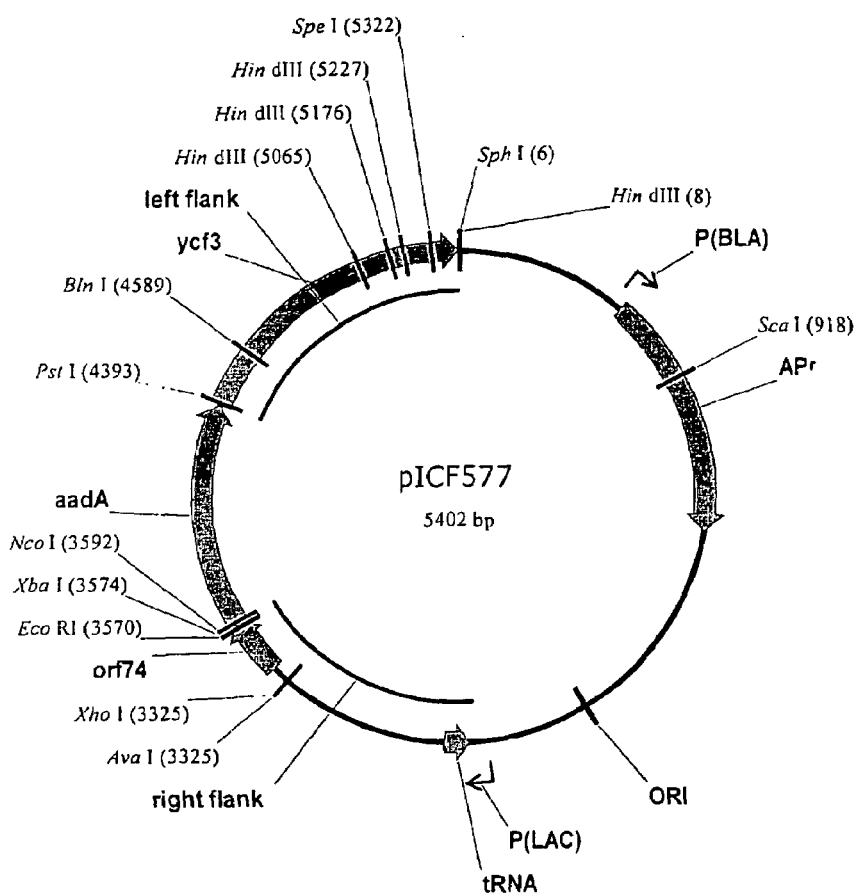
FIG. 10 shows a map of plastid transformation vector pICF577.
Figure 11:
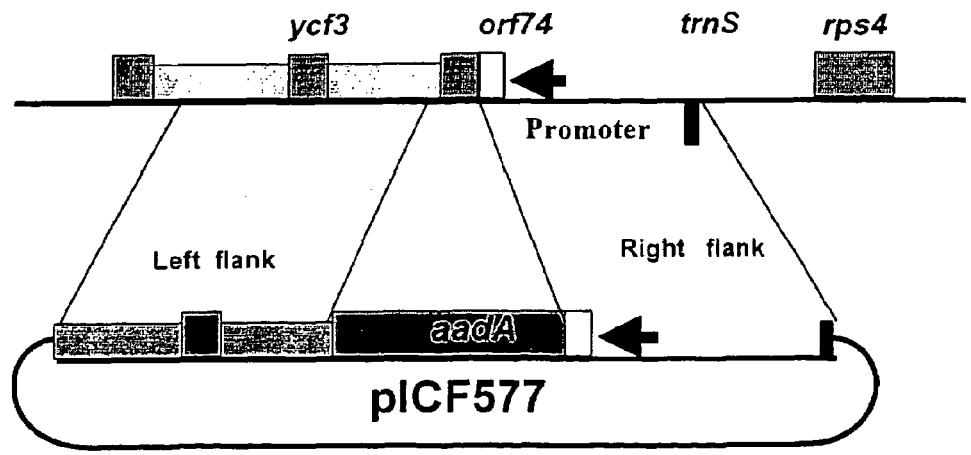
FIG. 11 shows a schematic view of vector pICF577.

The PCR amplification using Pfu polymerase (Promega) was performed as follows: 2 min at 94° C., 1 cycle; 45 sec at 94° C., 45 sec at 55° C., 2 min at 72° C., 30 cycles; final extension at 72° C. for 10 min. The amplified 5'-homologous fragment (corresponding to plastome nucleotides 46269-47205), containing 936 nucleotides upstream of the ycf3 start codon, was digested with Sma I and Nco I and then ligated into pUC16SaadA plasmid (Koop et al., 1996), which was digested with Eco RI, followed by a fill-in reaction using Klenow polymerase (Promega) and then digested with Nco I, generating pICF565. The amplified 3'-homologous fragment (corresponding to plastome nucleotides 45033-46041), containing 1000 nucleotides of the ycf3 gene, was digested with Pst I and Sph I, and then ligated into pICF565 cut with Pst I and Sph I, yielding the final transformation vector pICF577 (FIGS. 10 and 11). The identity of the plasmid insert was verified by sequencing (MWG, Munich).

Primary Transformation and Selection of Homoplastomic Δycf3 Mutants

Tobacco seeds (*Nicotiana tabacum* cv. *petit havanna*) were surface sterilized (1 min in 70% ethanol, 10 min in 5% Dimanin C, Bayer, Leverkusen, Germany), washed 3 times for 10 min in sterile $H_2O$ and put on B5 medium (preparation see below). Plants were grown at 25° C. in a 16 h light/8 h dark cycle (0.5-1 $W/m^2$, Osram L85W/25 Universal-White fluorescent lamps).

5 leaves from 4 weeks old, sterile grown *Nicotiana tabacum* cv. *petit havanna* plants were cut and transferred on RMOP-medium (preparation see below). 35 µl of a gold suspension (0.6 micron, Biorad, München; 60 mg/ml ethanol) was transferred into a sterile Eppendorf-cup (Treff, Fisher Scientific, Ingolstadt, Germany), collected by centrifugation and washed with 1 ml sterile $H_2O$. The gold pellet was resuspended in 230 µl sterile $H_2O$, 250 µl 2.5 M $CaCl_2$ and 25 µg DNA (transformation vector pICF577) were added. After thoroughly resuspending the mixture, 50 µl 0.1 M spermidin were added, mixed and incubated for 10 min on ice. Then the gold was collected by centrifugation (1 min, 10000 rpm) and washed twice with 600 µl ethanol (100%, p.A.). The gold was collected by centrifugation (1 min, 10000 rpm) and finally resuspended in 72 µl ethanol (100%, p.A.). A macrocarrier was inserted in the macrocarrier holder and 5.4 µl of the gold-suspension were applied. The bombardment was carried out with a Bio-Rad (Hercules, Calif., USA) PDS-1000/He Biolistic particle delivery system and the following parameters:

rapture disc 900 psi
helium pressure 1100 psi
vacuum 26-27 inches Hg
macrocarrier at the top level
leaf piece at the third level Six leaf pieces were bombarded each with 5.4 µl gold-suspension. After the bombardment the leaf pieces were incubated for 2 days at 25° C. on RMOP-medium.

Two days after bombardment, leaves were cut into small pieces (ca. 3×3 mm) and transferred to solid RMOP-medium containing 500 µg/ml spectinomycin. Leaf pieces were cut again and transferred to fresh medium after 2 weeks, then every 3 weeks until no further regenerates appeared. Primary Δycf3 transformants displayed spectinomycin-resistance and a green phenotype in the light, while still being heteroplastomic. In order to amplify transformed plastid DNA molecules and to eliminate wild-type genomes, the primary transformants were subjected to 3 additional rounds of regeneration on selective medium. Since segregation leads to the occurrence of white and green sectors, material from white sectors was subjected to several additional rounds of regeneration on non-selective medium in order to obtain homoplastomic mutant transformants. Homoplastomic transformed lines were rooted and propagated on solid VBW-medium (Aviv and Galun, 1985).

RMOP (pH5.8 with KOH): $NH_4NO_3$(1650 µg/ml), $KNO_3$ (1900 µg/ml), $CaCl_2 \cdot 2H_2O$ 440 (µg/ml), $MgSO_4 \cdot 7H_2O$ (370 µg/ml), $KH_2PO4$ (170 µg/ml), EDTA-Fe(III)Na (40 µg/ml), KI (0.83 µg/ml), $H_3BO_3$ (6.2 µg/ml), $MnSO_4 \cdot H_2O$ (22.3 µg/ml), $ZnSO_4 \cdot 7H_2O$ (8.6 µg/ml), $Na_2MoO_4 \cdot 2H_2O$ (0.25 µg/ml), $CuSO_4 \cdot 5H_2O$ (0.025 µg/ml), $CoCl_2 \cdot 6H_2O$ (0.025 µg/ml), Inositol (100 µg/ml), Thiamine-HCl (1 µg/ml), Benzylaminopurine (1 µg/ml), Naphthalene acetic acid (0.1 µg/ml), Sucrose (30000 µg/ml), Agar, purified (8000 µg/ml).

B5 (pH5.7 with KOH): $KNO_3$ (2500 µg/ml), $CaCl_2 \cdot 2H_2O$ (150 µg/ml), $MgSO_4 \cdot 7H_2O$ (250 µg/ml), $NaH_2PO_4 \cdot H_2O$ (150 µg/ml), $(NH_4)_2SO_4$(134 µg/ml), EDTA-Fe(III)Na (40 µg/ml), KI (0.75 µg/ml), $H_3BO_3$ (3 µg/ml), $MnSO_4 \cdot H_2O$ (10 µg/ml), $ZnSO_4 \cdot 7H_2O$ (2 µg/ml), $Na_2MoO_4 \cdot 2H_2O$ (0.25 µg/ml), $CuSO_4 \cdot 5H_2O$ (0.025 µg/ml), $CoCl_2 \cdot 6H_2O$ (0.025 µg/ml), Inositol (100 µg/ml), Pyridoxine-HCl (1 µg/ml), Thiamine-HCl (10 µg/ml), Nicotinic acid (1 µg/ml), Sucrose (20000 µg/ml), Agar, purified (7000 µg/ml).

VBW (pH5.8 with KOH): $NH_4NO_3$(1650 µg/ml), $KNO_3$ 1900 (µg/ml), $CaCl_2 \cdot 2H_2O$ (440 µg/ml), $MgSO_4 \cdot 7H_2O$ (370 µg/ml), $KH_2PO_4$ (170 µg/ml), EDTA-Fe(III)Na (40 µg/ml), KI (0.83 µg/ml), $H_3BO_3$ (6.2 µg/ml), $MnSO_4 \cdot H_2O$ (22.3 µg/ml), $ZnSO_4 \cdot 7H_2O$ (8.6 µg/ml), $Na_2MoO_4 \cdot 2H_2O$ (0.25 µg/ml), $CuSO_4 \cdot 5H_2O$ (0.025 µg/ml), $CoCl_2 \cdot 6H_2O$ (0.025 µg/ml), Inositol (100 µg/ml), Pyridoxin-HCL (0.5 µg/ml), Thiamine-HCl (1 µg/ml), Glycine (2 µg/ml), Nicotinic acid (0.5 µg/ml), Indolylacetic acid (2 µg/ml), Kinetin (0.2 µg/ml), Sucrose (30000 µg/ml), Caseinhydrolysat (500 µg/ml), Agar, purified (7000 µg/ml).

Analysis by PCR and Southern Blotting

Plastid transformants were identified by PCR amplification. The total DNA isolated from the first regenerates of 24 independent lines were used as a template for PCR. Two sets of primers (the sequences see example 3): oFCH59 and oFCH60; oFCH52 and oFCH53 were employed to analyze transplastomic plants. oFCH52 and oFCH53 should result in an amplification product of 900 bp from the wild-type plastome and a product of 1476 bp from transformed plastomes, whereas oFCH59 and oFCH60 should result in an amplification product of 480 bp from the transformed plants and no product from wild-type. The results show that 14 lines of transformants carry correct aadA insertions in the plastid genome. The data are also consistent with phenotypic appearance of the respective lines, which indicates that the pigment deficiency is correlated with deletion of ycf3.

Homoplasmy was verified by DNA gel blot analysis. Genomic DNAs isolated from young leaves of Δycf3 mutants (fourth cycle of regeneration) grown under low light conditions were used for DNA gel blot analysis. Detailed procedure was as follows: 4 μg of total plant DNA per analyzed plant was digested with restriction enzyme Xma JI and separated on a TAE-agarose gel (0.8%). The DNA was denatured and transferred to a positively charged nylon membrane (Hybond-N$^{+TM}$, Amersham) as described in Ausubel et al. (1999). The filter was hybridized with digoxigenin-labeled probes in DIG Easy Hyb Buffer (Roche Diagnostics GmbH, Mannheim, Germany), and hybridization signals were detected using the DIG Luminescent Detection Kit (Roche). The membrane was exposed to an X-OMAT LS film at room temperature for 2 hours.

For preparation of a DIG-labeled probe, tobacco genomic DNA was used as template to amplify a 520 bp fragment using the following pair of primers: oFCH69 (SEQ ID NO:24) (5'-CAT GGG AAC TGC TAT GTA GGC-3', corresponding to tobacco plastome sequence 47149-47169) and oFCH64 (SEQ ID NO:23) (5'-GAA TTA CCA AAC CAT TTG ACC C-3', corresponding to tobacco plastome sequence 47667-47647). The PCR DIG Probe Synthesis Kit from Roche was used. The PCR program was as follows: 2 min at 94° C., 1 cycle; 30 sec at 94° C., 30 sec at 55° C., 1 min at 72° C., 30 cycles; final extension at 72° C. for 10 min. The amplified fragment was gel purified using the QIAquick Gel Extraction Kit (QIAgen, Hilden, Germany) and then used for hybridization. This probe should result in a signal of 2780 bp from the transformed plastomes and a signal of 2198 bp from wild-type plastomes. The result showed that no wild-type plastid DNA could be detected in all 6 examined mutant lines.

Construction of Transformation Vector pICF7611 for Reconstitution of the ycf3 Gene Transformation vector pICF7611 was designed to transform the mutant Δycf3 line with the goal to reconstitute the ycf3 gene, remove the aadA gene, introduce the uidA gene at the same time, and transiently introduce the aphA-6 gene that confers resistance to kanamycin through one-flank integration.

For introduction of the uidA coding region into the upstream position of ycf3, two flanks (plastome nucleotides 45033-46266 and 46269-47205) were amplified by PCR adding desired restriction sites at the fragment ends (SphI/PstI and NcoI/SmaI), and a short ribosomal binding site (RBS) sequence serving as the signal to translate the reconstituted ycf3 gene as a newly formed artificial operon. The uidA gene and ycf3 are transcribed in the same direction under control of ycf3 5'-regulatory element. The following two pairs of oligonucleotide primers were used: oFCH139 (SEQ ID NO:71) (5'-Pst I-ATC ACT AGT TGT AGG GAG GGA TCC ATG CCT AGA TCA CGG ATAAA-3', (SEQ ID NO:67 5'-Pst I-ATC ACT AGT TGT AGG GAG GGA TCC-3' (ribosome binding site)), annealing with plastome nucleotides 46266-46247) and oFCH78 (SEQ ID NO:21) (5'-Sph I-GAA GTT TCT TTC TTT GCT ACA-3', annealing with plastome nucleotides 45033-45053); oFCH76 (SEQ ID NO:19) (5'-Nco I-GTA GCA ATC CAT TCT AGA AT-3', annealing with plastome nucleotides 46269-46288) and oFCH77 (SEQ ID NO:20) (5'-Sma I-CGG AAA GAG AGG GAT TCT AAC-3', annealing with plastome nucleotides 47205-46185). The PCR amplification using Taq polymerase (Promega) was performed as follows: 2 min at 94° C., 1 cycle; 45 sec at 94° C., 45 sec at 55° C., 2 min at 72° C., 30 cycles; final extension at 72° C. for 10 min. The two flanks were digested with the corresponding enzymes and ligated together with the gus coding region (prepared as a PstI/NcoI fragment) into pUC19 linearized with SmaI/SphI to give pICF601.

Figure 12:
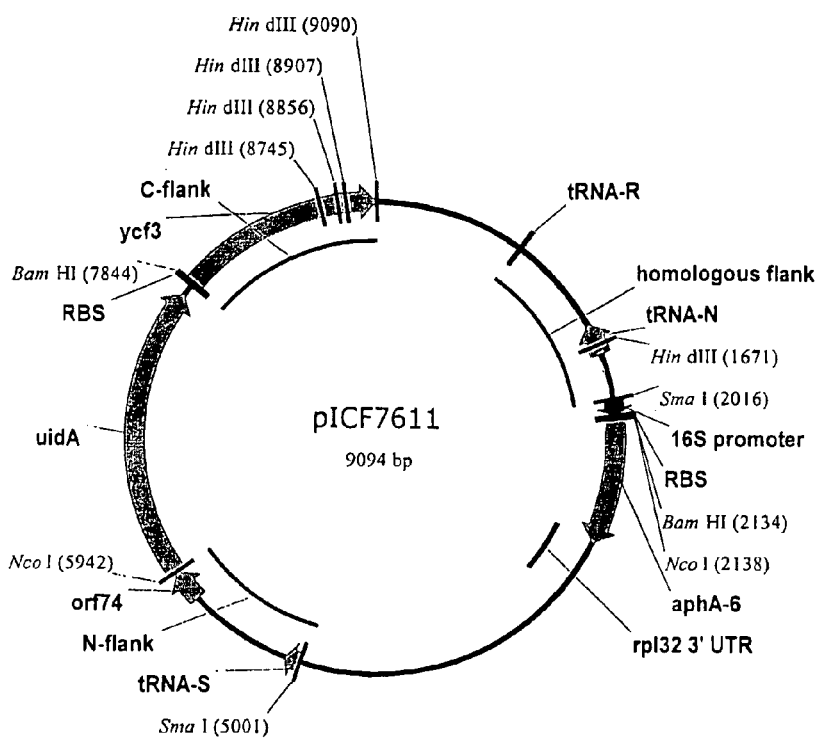
FIG. 12 shows a map of plastid transformation vector pICF7611.
Figure 13:
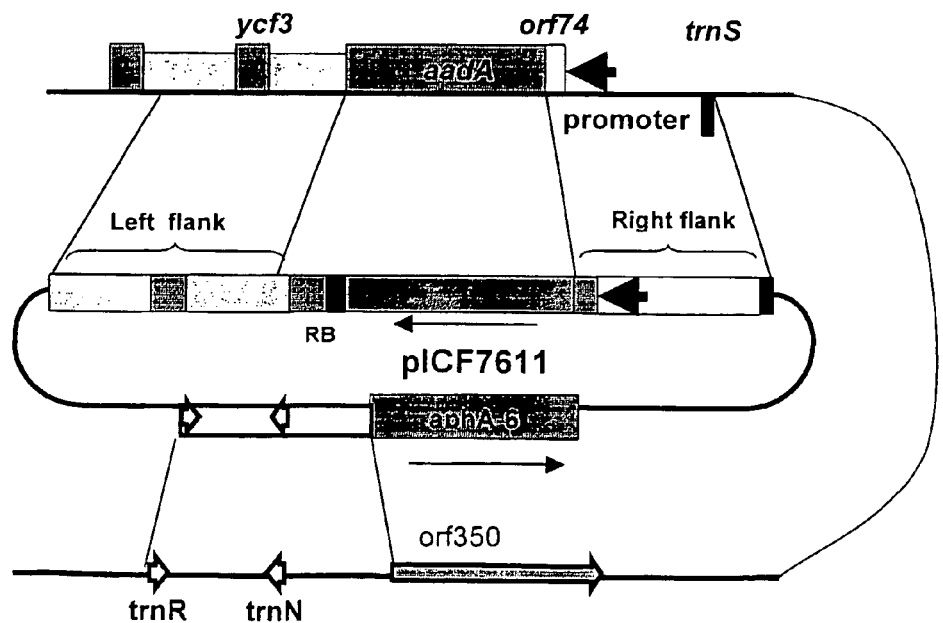
FIG. 13 shows a schematic view of vector pICF7611.

For transient introduction of the aphA-6 expression cassette into the plastid genome via one homologous flank, the aadA coding region and the attached 3'UTR of vector B1 (Mühlbauer et al., 2002) was removed by NcoI/KpnI digestion and replaced by the aphA-6 coding region and the adjacent 3'UTR of vector pICF606 (Huang et al., 2002) to give vector pICF746. The left flank and the aphA-6 expression cassette from vector pICF746 was taken as PmaCI/KpnI fragment, blunted by T4 DNA polymerase treatment and ligated into the single ScaI restriction site of vector pICF601 (dephosphorylated by calf intestine alkaline phosphatase treatment) to give the final transformation vector pICF7611 (FIGS. 12 and 13).

Plastid Transformation of Δycf3 Mutant Lines and Selection of Homoplastomic Lines PEG-mediated transmembrane DNA transfer into protoplasts is a reproducible method for plastid transformation of higher plants (Golds et al., 1993; O'Neill et al., 1993). Protoplast regeneration was recently optimized according to Dovzhenko et al., 1998).

A. Protoplast isolation: Leaves from sterile homoplastomic Δycf3 mutants grown under low light conditions on solid VBW-medium were cut in 1 mm stripes and incubated overnight with 0.25% cellulase R10 and 0.25% macerozyme R10 (Yakult, Honsha Japan) dissolved in F-PIN medium. Following standard filtration, flotation and sedimentation procedures (Koop et al., 1996) protoplasts were resuspended in transformation medium, the total number of protoplasts was determined, and the density was adjusted to $5 \times 10^6$ protoplasts per ml.

F-PIN medium (pH 5.8 (KOH), osmolarity: 550 mOsm): $KNO_3$(1012 μg/ml), $CaCl_2 \cdot 2H_2O$ (440 μg/ml), $MgSO_4 \cdot 7H_2O$ (370 μg/ml), $KH_2PO_4$ (170 μg/ml), $NH_4$-succinate (10 ml of 2M stock), EDTA-Fe(III)·Na-salt (40 μg/ml), KJ (0,75 μg/ml), $H_3BO_3$ (3 μg/ml), $MnSO_4 \cdot H_2O$ (10 μg/ml), $ZnSO_4 \cdot 7H_2O$ (2 μg/ml), $Na_2MoO_4 \cdot 2H_2O$ (0.25 μg/ml), $CuSO_4 \cdot 5H_2O$ (0.025 μg/ml), $CoCl_2 \cdot 6H_2O$ (0.025 μg/ml), inositol (200 μg/ml), pyridoxin-HCl (2 μg/ml), thiamin-HCl (1 μg/ml), biotin (0,02 μg/ml), nicotinic acid (2 μg/ml), BAP (1 μg/ml), NAA (0,1 μg/ml), Polybuffer 74 (10 ml), sucrose (~130 000 μg/ml).

Transformation medium (pH 5.8 (KOH), osmolarity: 550 mOsm): $MgCl_2 \cdot 6H_2O$ (3050 μg/ml), MES (1000 μg/ml), mannitol (~80000 μg/ml).

B. Plastid transformation and protoplast embedding: 50 μg DNA (transformation vector pICF761), 7 μl F-PCN, and 100 μl (500.000 cells) of protoplast suspension were added to 125 μl 40% PEG solution, mixed carefully and incubated for 7.5 min. Another 125 μl of F-PCN were added, mixed and incubated for 2 min. The volume was filled up to 3 ml (with F-PCN) and 3 ml of F-alginate medium was added. Alginate embedding in thin layers is performed by applying 625 μl of protoplast-alginate mixture to propylene grids on the surface of $Ca^{2+}$-medium. After solidification grids were removed and placed upside down into liquid F-PCN medium for equilibration (10 ml, 60 min) and then transferred to a new petri dish with 2 ml F-PCN. The embedded protoplasts were incubated in darkness for the initial 20 hours, then transferred to low light conditions (a usual 16 h day/8 h dark cycle) (Dovzhenko et al., 1998).

F-PCN medium (pH 5,8 (KOH), osmolarity: 550 mOsm): $KNO_3$(1012 μg/ml), $CaCl_2 \cdot 2H_2O$ (440 μg/ml), MgSO$_4$·7H$_2$O (370 µg/ml), KH$_2$PO$_4$ (170 µg/ml), NH$_4$-succinate (10 ml of 2M stock), EDTA-Fe(III) Na-salt (40 µg/ml), KJ (0.75 µg/ml), H$_3$BO$_3$ (3 µg/ml), MnSO$_4$·H$_2$O (10 µg/ml), ZnSO$_4$·7H$_2$O (2 µg/ml), Na$_2$MoO$_4$·2H$_2$O (0.25 µg/ml), CuSO$_4$·5H$_2$O (0,025 µg/ml), COCl$_2$·6H$_2$O (0.025 µg/ml), inositol (200 µg/ml), pyridoxin-HCl (2 µg/ml), thiamin-HCl (1 µg/ml), biotin (0.02 µg/ml), nicotinic acid (2 µg/ml), BAP (1 µg/ml), NAA (0,1 µg/ml), Polybuffer 74 (10 ml), sucrose (~20000 µg/ml), glucose (65 000 µg/ml).

F-alginate medium (pH 5.8 (KOH), osmolarity: 550 mOsm): MES (1370 µg/ml), MgSO$_4$·7H$_2$O (2500 µg/ml), MgCl$_2$ 6H$_2$O (2040 µg/ml), mannitol (~77000 µg/ml), alginate (24000 µg/ml).

Ca$^{2+}$-medium (pH 5.8 (KOH), osmolarity: 550 mOsm): MES (1950 µg/ml), CaCl$_2$·2H$_2$O (2940 µg/ml), mannitol (~82000 µg/ml), agar purified (10000 µg/ml).

One week after transformation, embedded protoplasts were transferred to solid RMOP medium containing 25 µg/ml kanamycin and cultivated at low light conditions for two weeks. Afterwards, every two weeks grids were transferred to fresh medium and cultivated at strong light conditions until no further regenerates appeared. First green regenerates appeared after 6 weeks and were transferred individually to petri dishes. As expected, primary ycf3-reconstituted transformants displayed kanamycin-resistance and a segregation phenotype in the light, while still being heteroplastomic. In order to amplify ycf3-reconstituted plastid DNA molecules, to eliminate ycf3-deleted genomes, and to remove the aphA-6 maker gene, the transformants were transferred to B5 medium without antibiotics for segregation. Green sectors appeared after 3 weeks of culture. Material from green sectors was further subcultured on non-selective medium and subjected to several further cycles of regeneration in order to obtain marker-free homoplastomic ycf3-reconstituted transformants. The resulting lines showing a green phenotype were rooted on solid B5-medium, following transfer to the greenhouse for propagation.

Molecular Analysis of the Secondary Transplastomic Plants

Plastid transformants were identified by PCR amplification. The total DNA isolated from primary transformants, which displayed a green phenotype and were able to grow photoautotrophically, were used as a template for PCR analysis using the following oligonucleotide primers: oSM61 (SEQ ID NO:16) (5'-TCACACCGATACCAT-CAGCG-3', derived from the 5' portion of the uidA coding region), oSM62 (SEQ ID NO:17) (5'-ATTGTTTGCCTC-CCTGCTGC-3', derived from the 3' portion of the uidA coding region), oFCH27 (SEQ ID NO:25) (5'-TGC TCA AGA CTT TAG TGG ATC-3', annealing with plastome nucleotides 44799-44819), oSM58 (SEQ ID NO:26) (5'-TATTCCGACTTCCCCAGAGC-3', annealing with plastome nucleotides 109138-109157), oFCH168 (SEQ ID NO:27) (5'-TCA GTC GCC ATC GGA TGT TT-3', derived from the 5' portion of the aphA-6 coding region) and oFCH169 (SEQ ID NO:28) (5'-ACC AAT CTT TCT TCA ACA CG-3', derived from the 3' portion of the aphA-6 coding region). oSM61 and oSM62, which should result in an amplification product of 500 bp from the reconstituted plants, and no product from unchanged first round transformants, were used to detect the presence of the uidA gene. The combination of oFCH27 and oSM61 can determine whether the second round transformants carry correct gus insertions or not by amplifying a product of about 3000 bp from correctly transformed plastomes. oFCH168 and oFCH169 were used to detect the presence of the aphA-6 gene. oSM58 and oFCH 169 were used to detect the integration of the complete vector sequence (containing the aphA-6 gene) via one homologous flank. In total 2 unique ycf3-reconstituted tobacco plastid transformants were obtained from one PEG transformation experiment. The data show that the uidA gene is integrated into the plastid genome by two-homologous-flanks integration, whereas the aphA-6 gene is introduced through one-flank integration.

Additional proof of correct integration and of the homoplastomic genotype was given by DNA gel blot analysis. Genomic DNAs isolated from sterile grown plants were digested with Xma JI. The probe used was the same as that for Δycf3 mutants (detailed procedures for DNA blotting and hybridization see above). The probe generates a signal of 2219 bp for wild-type plastome, a signal of 4123 bp for plastomes correctly transformed in the second round, and a signal of 2793 bp for unchanged first round transformants.

To confirm the removal of the aadA marker and the aphA-6 marker, further hybridizations of the blot (of which the former probe had been removed by a stripping procedure) were done using a 480 bp fragment of the aadA-gene and a 500 bp fragment of the aphA-6 gene as probe. For probe generation primers oFCH59 and oFCH60 for aadA, oFCH168 and oFCH169 for aphA-6 were used in a PCR DIG labeling reaction according to the protocol of the supplier (Roche).

Example 4

Stable Introduction of a Gus Gene Into the Plastome by Transient Selection for a One Flank Mediated Integration of the aphA-6 Gene Transformation and Selection of Kanamycin-Resistant Transformants The transformation vector pICF7611 (construction see example 3) was transformed to wild-type tobacco via the PEG-mediated method (for detail see example 3).

One week after transformation embedded protoplasts were transferred to solid RMOP medium containing 25 µg/ml kanamycin. Every 2 weeks the grids were transferred to fresh medium until no further regenerates appeared. First green regenerates appeared after 6 weeks and were transferred individually to petri dishes. Primary transformants were subjected to several further cycles of regeneration on RMOP medium containing 25 µg/ml kanamycin in order to obtain homoplastomic transformants. For excision of the aphA-6 marker gene, homoplastomic transformants were subjected to several additional rounds of regeneration on non-selective medium in order to obtain marker-free transformants. The resulting lines showing a green phenotype were rooted on solid B5-medium, and then transferred to the greenhouse for propagation.

Analysis by PCR and Southern Blotting

Plastid transformants were identified by PCR amplification. Total DNA isolated from primary transformants, which displayed green phenotype and kanamycin resistance was used as a template for PCR analysis using the following oligonucleotide primers: oSM61 (SEQ ID NO:16) (5'-TCA-CACCGATACCATCAGCG-3', derived from the 5' portion of the uidA coding region), oSM62 (SEQ ID NO:17) (5'-ATTGTTTGCCTCCCTGCTGC-3', derived from the 3' portion of the uidA coding region), oFCH27 (SEQ ID NO:25) (5'-TGC TCA AGA CTT TAG TGG ATC-3', annealing with plastome nucleotides 44799-44819), oSM58 (SEQ ID NO:26) (5'-TATTCCGACTTCCCCAGAGC-3', annealing with plastome nucleotides 109138-109157), oFCH168 (SEQ ID NO:27) (5'-TCA GTC GCC ATC GGA TGT TT-3', derived from the 5' portion of the aphA-6 coding region), and oFCH 169 (SEQ ID NO:28) (5'-ACC AAT CTT TCT TCA ACA CG-3', derived from the 3' portion of the aphA-6 coding region). oSM61 and oSM62, which should result in an amplification product of 500 bp from the transformants and no product from wild-type, were used to detect the presence of the uidA gene. The combination of oFCH27 and oSM61 can determine, whether the transformants carry correct uidA insertions by amplifying a product of about 3000 bp from correctly transformed plastomes. oFCH168 and oFCH169 were used to detect the presence of the aphA-6 gene. oSM58 and oFCH169 were used to detect the integration of the complete vector sequence (containing the aphA-6 gene) via one homologous flank. In total, 2 tobacco plastid transformants were obtained from one PEG transformation experiment. The data show that the uidA gene is stably integrated into the plastid genome by integration via two homologous flanks, whereas the aphA-6 gene is introduced through one-flank integration.

Additional proof of correct integration and of the homoplastomic genotype was given by DNA gel blot analysis. Genomic DNAs isolated from sterile grown plants were digested with Xma JI. The probe used was the same as that for Δycf3 mutants (detailed procedures for DNA blotting and hybridization see example 3). The probe generates a signal of 2219 bp for wild-type plastome, a signal of 4123 bp for plastomes correctly transformed. To confirm the removal of the aphA-6 marker, further hybridization of the blot (of which the former probe had been removed by a stripping procedure) was done using a 500 bp fragment of the aphA-6 gene as probe. For probe generation primers oFCH168 and oFCH169 for aphA-6 were used in a PCR DIG labeling reaction according to the protocol of the supplier (Roche).

Example 5

Inactivation/Reactivation of rpoA and Stable Introduction of an Interferon Gene by Transient Selection for a One Flank Mediated Integration of the aphA-6 Gene Plastid chromosomes encode four RNA polymerase genes, designed rpoA, B, C1 and C2 that resemble the three RNA polymerase core genes of *eubacteria*. The genes for rpoB, C1 and C2 are arranged in an operon (transcribed by NEP), while the gene for rpoA is located in a large cluster of genes that mainly encode ribosomal proteins. Since the level of the sense transcript of rpoA gene decreases in the PEP (plastid-encoded polymerase) mutants (Krause et al., 2000), rpoA might be transcribed by PEP.

Deletion of rpoA from the plastid genome results in a pigment-deficient phenotype (De Santis-Maciossek et al., 1999). The pigment-deficient ΔrpoA plants (white plants) are unable to grow photoautotrophically. However, if maintained on sucrose-containing medium to compensate for the lack of photosynthesis, they grow normally but at a reduced rate compared with wild-type plants.

Construction of Transformation Vector pICF836 for Targeted Inactivation of the rpoA Gene A transformation vector, designed to inactivate the rpoA gene by replacing the first 110 bp of rpoA coding region (corresponding to plastome nucleotides 81359-81468) with the uidA coding region, was constructed. This vector does not contain any 3' regulatory elements. In addition, no promoter elements were introduced, and the Gus gene is expected to be transcribed and translated by the endogenous rpoA upstream regulatory element.

This vector contains the uidA coding region, flanked by 5'- and 3'-homologous sequences which were amplified from the tobacco chloroplast genome by PCR using the following two pairs of primers: oFCH112 (SEQ ID NO:29) (5'-Nco I-TAC TAT TAT TTG ATT AGA TC-3', annealing with plastome nucleotides 81471-81490) and oFCH113 (SEQ ID NO:30) (5'-Sma I-TAA TTA CTG MT CGC TTC CCA-3', annealing with plastome nucleotides 82470-82450); oFCH295 (SEQ ID NO:31) (5'-HindIII -TTA AAA CTT ATT T TGC TAA-3', annealing with plastome nucleotides 80455-80475) and oFCH296 (SEQ ID NO:32) (5'-Pst I-TAT GM AGG CCA AGC CGA CA-3', annealing with plastome nucleotides 81358-81339). The PCR amplification using Pfu polymerase (Promega) was performed as follows: 2 min at 94° C., 1 cycle; 45 sec at 94° C., 45 sec at 55° C., 2 min at 72° C., 30 cycles; final extention at 72° C. for 10 min. The two flanks were digested with the corresponding enzymes and ligated together with the uidA coding sequence (prepared as a Pst I/Nco I fragment) into pUC19 linearized with Sma I/HindIII to give pICF835.

Figure 14:
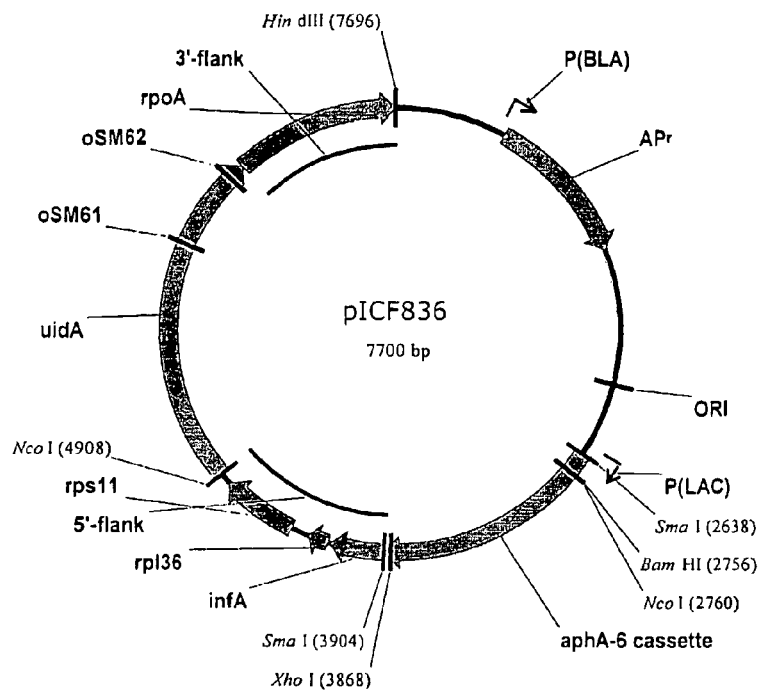
FIG. 14 shows a map of plastid transformation vector pICF836.

For transient introduction of the aphA-6 gene, the aphA-6 cassette was prepared as a Xma I fragment and ligated into pICF835 linearized with Xma I to give the final transformation vector pICF836 (FIG. 14). The aphA-6 cassette is situated outside of the homologous flanks.

Primary Transformation and Selection of Homoplastomic ΔrpoA Mutants

The transformation vector pICF836 was transformed to wild-type tobacco via the PEG-mediated method (for detail see example 3).

One week after transformation embedded protoplasts were transferred to solid RMOP medium containing 25 μg/ml kanamycin. Every 2 weeks the grids were transferred to fresh medium until no further regenerates appeared. First green regenerates appeared after 6 weeks and were transferred individually to petri dishes. As expected, primary rpoA⁻ transformants displayed kanamycin-resistance and a green phenotype in the light while still being heteroplastomic. For segregation and excision of the aphA-6 marker gene, the transformant colonies were transferred to RMOP medium without inhibitors. White sectors appeared after 3 to 5 weeks of culture. Material from white sectors was further subcultured on non-selective medium and subjected to 5 further cycles of regeneration in order to obtain marker-free homoplastomic mutant transformants. The resulting lines showed a white phenotype. The transplastomic lines were rooted and propagated on solid VBW-medium to obtain mutant plant material for the secondary transformation.

Analysis by PCR and Southern Blotting

Plastid transformants were identified by PCR amplification. Total DNA isolated from primary transformants which displayed kanamycin resistance, was used as a template for PCR analysis using the following oligonucleotide primers: oSM61 (SEQ ID NO:16) (5'-TCA CAC CGA TAC CAT CAG CG-3', derived from the 5' portion of the uidA coding region), oSM62 (SEQ ID NO:17) (5'-ATT GTT TGC CTC CCT GCT GC-3', derived from the 3' portion of the uidA coding region), oFCH121 (SEQ ID NO:33) (5'-TAA ATC CCT AAC TTT AGG TC-3', corresponding to tobacco plastome sequence 80240-80259), oFCH168 (SEQ ID NO:27) (5'-TCA GTC GCC ATC GGA TGT TT-3', derived from the 5' portion of the aphA-6 coding region), and oFCH169 (SEQ ID NO:28) (5'-ACC AAT CTT TCT TCA ACA CG-3', derived from the 3' portion of the aphA-6 coding region). oSM61 and oSM62, which should result in an amplification product of 500 bp from the transformants and no product from wild-type, were used to detect the presence of the uida gene. The combination of oFCH121 and oSM61 can determine, whether the transformants carry correct gus insertions by amplifying a product of about 1620 bp from correctly transformed plastomes. oFCH168 and oFCH169 were used to detect the presence of the aphA-6 gene by amplifying a product of about 500 bp. In total, 4 tobacco plastid transformants were obtained from one PEG transformation experiment. The results show that the uidA gene is stably integrated into the plastid genome by integration via two homologous flanks, whereas the aphA-6 gene is introduced through one-flank integration. The data are also consistent with phenotypic appearance of the respective lines, which indicated that the pigment deficiency was correlated with deletion of rpoA.

Additional proof of correct integration and of the homoplastomic genotype was given by DNA gel blot analysis. Genomic DNAs isolated from sterile grown plants were digested with Eco RI. For preparation of a DIG-labled probe, tobacco genomic DNA was used as template to amplify a 520 bp fragment using the following pair of primers: oFCH206 (SEQ ID NO:34) (5'-TGA GTC AGA GAT ATA TGG AT-3', corresponding to tobacco plastome sequence 81971-81990) and oFCH113 (SEQ ID NO:30) (5'-TAA TTA CTG AAT CGC TTC CCA-3', annealing with plastome nucleotides 82470-82450). The PCR DIG Probe Synthesis Kit from Roche was used. The PCR program was as follows: 2 min at 94° C., 1 cycle; 30 sec at 94° C., 30 sec at 55° C., 1 min at 72° C., 30 cycles; final extention at 72° C. for 10 min. The amplified fragment was gel purified using the QIAquick Gel Extraction Kit (QIAgen, Hilden, Germany) and then used for hybridization. Detailed procedures for DNA blotting and hybridization see example 3. This probe should result in a signal of 3133 bp from the transformed plastomes and a signal of 2384 bp from wild-type plastomes. The result showed that no wild-type plastid DNA could be detected in all 4 examined mutant lines. To confirm the removal of the aphA-6 marker, further hybridization of the blot (of which the former probe had been removed by a stripping procedure) was done using a 500 bp fragment of the aphA-6 gene as probe. For probe generation primers oFCH168 and oFCH169 for aphA-6 were used in a PCR DIG labeling reaction according to the protocol of the supplier (Roche).

Construction of the Transformation Vector pICF838 for Reconstitution of the rpoA Gene and Introduction of the Interferone Gene Transformation vector pICF838 was designed to transform the mutant ΔrpoA line with the goal to reconstitute the rpoA gene, introduce the interferon gene at the same time, and transiently introduce the aphA-6 gene that confer resistance to kanamycin.

For introduction of the Prrn16S promoter, T7G10 leader, and interferon coding region into the upstream position of rpoA, two flanks (plastome nucleotides 81471-82470 and 80455-81468) were amplified by PCR adding desired restriction sites at the fragment ends and a short ribosomal bonding site (RBS) sequence serve as the signal to translate the reconstituted rpoA gene as a newly formed artificial operon. The interferon gene and rpoA are transcribed in the same direction under control of the Prrn16S promoter. The following two pairs of oligonucleotide primers were used: oFCH297 (SEQ ID NO:35) (5'-Pst I-GGT ACT ATT ATT TGA TTA GAT-3', annealing with plastome nucleotides 81469-81489) and oFCH298 (SEQ ID NO:36) (5'-Hin dIII-TAA TTA CTG AAT CGC TTC CCA-3', annealing with plastome nucleotides 82470-82450); oFCH299 (SEQ ID NO:37) (5'-Eco RI-TTA AM CTT ATT TTT TGC TAA-3', annealing with plastome nucleotides 80455-80475) and oFCH300 (SEQ ID NO:72) (5'-Sac I-TC ACT AGT TGT AGG GAG GGA TCC (RBS) ATG GTT CGA GAG AAA GTA AC-3', annealing with plastome nucleotides 81468-81449). The PCR amplification using Taq polymerase (Promega) was performed as follows: 2 min at 94° C., 1 cycle; 45 sec at 94° C., 45 sec at 55° C., 2 min at 72° C., 30 cycles; final extension at 72° C. for 10 min.

The Prrn16S promoter-interferon fragment was first cut from pICF781-3 with Pst I/Kpn I, and then ligated into the pUC19 linearized with Pst I/Kpn I to give pICF834. The two amplified flanks were digested with the corresponding enzymes and one after another ligated together with the Prrn16S promoter-interferon fragment into pICF834 to give pICF837.

Figure 15:
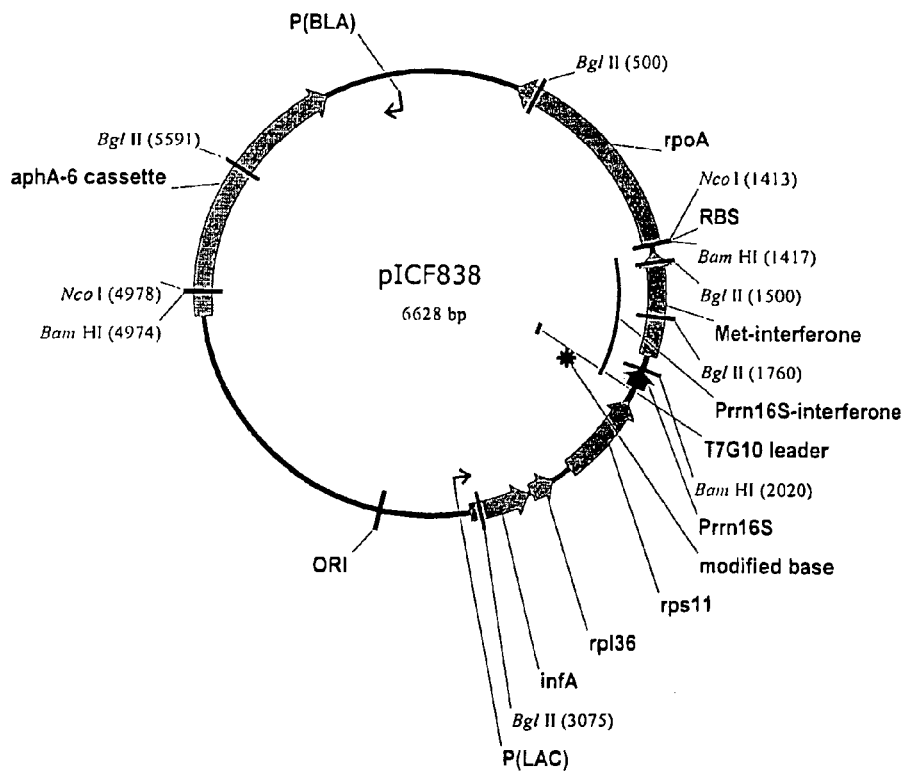
FIG. 15 shows a map of plastid transformation vector pICF838.
Figure 16:
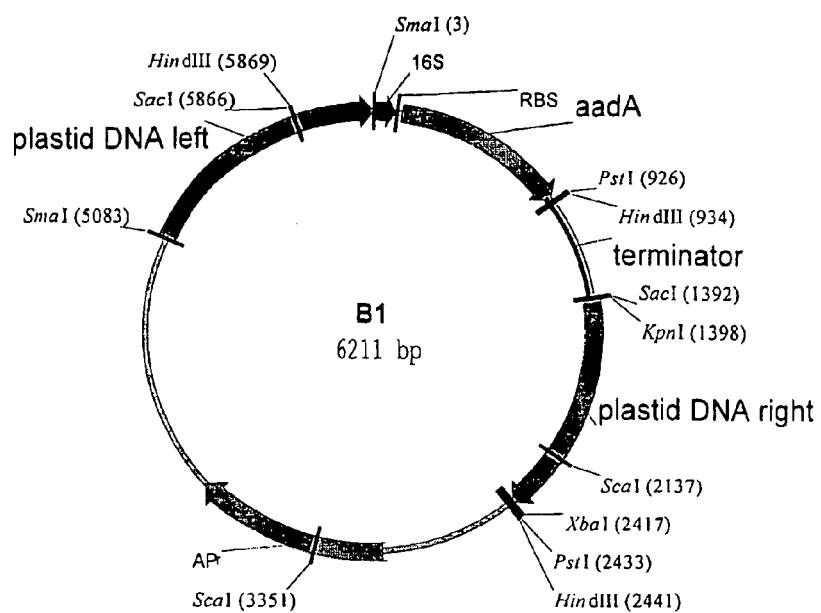
FIG. 16 shows a map of plastid transformation vector pICFB1.

For transient introduction of the aphA-6 gene, the aphA-6 cassette was prepared as a Sma I fragment and ligated into pICF837 linearized with Sca I to give the final transformation vector pICF838 (FIG. 15). The aphA-6 cassette is situated outside of the homologous flanks.

Plastid Transformation of ΔrpoA Mutant Lines and Selection of Homoplastomic Lines The transformation vector pICF838 was transformed to ΔrpoA mutant lines via the PEG-mediated method (for detail see example 3).

After transformation, embedded protoplasts were cultivated in the dark. One week later, embedded protoplasts were transferred to solid RMOP medium containing 15 μg/ml kanamycin and cultivated at low light conditions for two weeks. Afterwards, every two weeks grids were transferred to fresh medium and cultivated at normal growth conditions until no further regenerates appeared. First green regenerates appeared after 6 weeks and were transferred individually to petri dishes. As expected, primary rpoA-reconstituted transformants displayed kanamycin-resistance and a segregation phenotype in the light, while still being heteroplastomic. In order to amplify rpoA-reconstituted plastid DNA molecules, to eliminate rpoA-deleted genomes, and to remove the aphA-6 maker gene, the transformants were transferred to B5 medium without antibiotics for segregation. Green sectors appeared after 3 weeks of culture. Material from green sectors was further subcultured on non-selective medium and subjected to several further cycles of regeneration in order to obtain marker-free homoplastomic rpoA-reconstituted transformants. The resulting lines showing a green phenotype were rooted on solid B5-medium and were transferred to the greenhouse for propagation.

Molecular Analysis of the Secondary Transplastomic Plants

Plastid transformants were identified by PCR amplification. The total DNA isolated from primary transformants which displayed green phenotype and were able to grow photoautotrophically were used as a template for PCR analysis using the following oligonucleotide primers: oMF228 (SEQ ID NO:38) (5'-GGA ATT CCAT ATG TGT GAT CTG CCT CM ACC CAC AG-3', derived from the 5' portion of the interferon coding region), oMF229 (SEQ ID NO:39) (5'-CGGGGTACCTCATTCCTTACTTCT-TAAACTTTC-3', derived from the 3' portion of the interferon coding region), oFCH121 (SEQ ID NO:33) (5'-TAA ATC CCT AAC TTT AGG TC-3', corresponding to tobacco plastome sequence 80240-80259), oFCH168 (SEQ ID NO:27) (5'-TCA GTC GCC ATC GGA TGT TT-3', derived from the 5' portion of the aphA-6 coding region) and oFCH169 (SEQ ID NO:28) (5'-ACC AAT CTT TCT TCA ACA CG-3', derived from the 3' portion of the aphA-6 coding region). oMF228 and oMF229 which should result in an amplification product of 500 bp from the reconstituted plants and no product from unchanged first round transformants were used to detect the presence of the interferon gene. The combination of oFCH121 and oMF228 can determine whether the second round transformants carry correct interferone insertions by amplifying a product of about 1730 bp from correctly transformed plastomes. oFCH168 and oFCH169 were used to detect the presence of the aphA-6 gene. In total 11 unique rpoA-reconstituted tobacco plastid transformants were obtained from one PEG transformation protocol. The data show that the interferon gene is integrated into the plastid genome by two homologous flanks integration, whereas the aphA-6 gene is introduced through one-flank integration.

Additional proof of correct integration and the homoplastomic genotype was given by DNA gel blot analysis. Genomic DNAs isolated from sterile grown plants were digested with Eco RI/Pst I. The probe used was the same as that for ΔrpoA mutants (detailed procedures for DNA blotting and hybridization see example 3). The probe generates a signal of 2384 bp for wild-type plastome, a signal of 1247 bp for plastomes correctly transformed in the second round, and a signal of 3127 bp for unchanged first round transformants.

To confirm the removal of the aphA-6 marker, further hybridizations of the blot (of which the former probe had been removed by a stripping procedure) were done using a 500 bp fragment of the aphA-6 gene as probe. For probe generation primers oFCH168 and oFCH169 were used in a PCR DIG labeling reaction according to the protocol of the supplier (Roche).

Example 6

Stable Introduction of an Interferon Gene Into the Plastome by Transient Selection for a One Flank Mediated Integration of the aphA-6 Gene This example describes the generation of transplastomic plants devoid of antibiotic resistance genes using transient marker integration, whereby visual identification of transformed tissue during segregation is supported by GFP expression. The transformation vector described in this example (pICF846) is based on the rpoA reconstitution vector pICF838 (see example 5); this vector cannot only be used for reconstitution of mutants, but also for transformation of wild-type plants, leading to insertion of sequences of interest (in this case the interferon coding sequence) upstream of rpoA in the plastome. In order to allow visual identification of transformants, a sequence encoding GFP is inserted between the interferon and rpoA coding sequences. For this purpose, a cassette consisting of an artificial ribosomal binding site (Eibl et al., 1999), a downstream box from the tobacco rbcL gene, and a GFP coding sequence is inserted into the KpnI restriction site of plasmid pICF837 (see example 5); the aphA-6 marker cassette is hereafter inserted outside of the flanking regions into the ScaI site, as described above (example 5).

Transformation vector pICF846 is used for transformation of wild-type tobacco via the PEG-mediated method as described in example 3. Selection of transformants is made on 25 μg/ml kanamycin as described in example 4. Green fluorescence of transformants can be visualized in UV light provided by a hand lamp or a fluorescence microscope provided with appropriate filters. Homoplastomic transformants are subjected to several additional rounds of regeneration on non-selective medium in order to allow excision of the antibiotic resistance marker. Excision of the complete transformation vector including the sequences of interest can be easily recognized due to loss of green fluorescence. Plant material retaining fluorescence is analyzed for loss of the aphA-6 gene. Material showing complete loss of the selection marker is propagated.

Example 7

Autonomously Replicating Plastid Transformation Vector pICFB1 Providing an Integration Cassette Construction of Plastid Transformation Vector pICFB1

A cassette consisting of the aminoglycoside 3'-adenyltransferase (aadA) from *E. coli* under the control of the tobacco rrn16 promoter was cloned as follows a DNA fragment containing the rrn16 promoter was amplified by PCR from tobacco (*Nicotiana tabacum* cv. *Petite Havana*) DNA with primers "5-24" (SEQ ID NO:40) (5'-ccgaattcgccgtcgttcaatgag-3') and "3-21" (SEQ ID NO:41) (5'-cacgatatcgcccggagttg-3'). The amplified fragment was cut with EcoRI and EcoRV.

A linker DNA fragment encompassing the ribosomal binding site (RBS) of the tobacco rbcL gene was constructed by annealing primer "5-rbs" (SEQ ID NO:42) (5'-ctcgatatcactagttgtagggaggga-3') and primer "3-rbs" (SEQ ID NO:43) (5'-gtgccatggatccctcct-3'). The overhangs were filled in with Klenow DNA polymerase, and the fragment was cut with EcoRV and NcoI.

Plasmid pUC-atpX-AAD (provided by Dr. M. Goldschmidt-Clermont, Department of Plant Biology and Molecular Biology, University of Geneva, Switzerland; Goldschmidt-Clermont, 1991), containing the bacterial aadA coding sequence fused to a 440 bp fragment of the *Chlamydomonas reinhardtii* rbcL downstream region, was cut with EcoRI and NcoI to remove the original promoter fragment. The EcoRV and NcoI treated RBS-fragment and the EcoRI and EcoRV treated rrn16 promoter fragment were inserted into the promoterless pUC-atpX-AAD vector simultaneously, yielding plasmid pUC16SaadA. An additional SmaI/XmaI-site was created upstream of the rrn16 promoter by insertion of a linker oligonucloetide (gaattccggggaattc) into the EcoRI-site (pUC16SaadA-Sma).

Tobacco (*Nicotiana tabacum* cv. *Petite Havana*) plastid DNA sequence 112061 to 113058 (Accession Number Z00044) was amplified with PCR from isolated tobacco DNA using primers b1-1 (SEQ ID NO:45) (5'-ggggtaccgaatttgattcacaaagttg-3') and b1-2 (SEQ ID NO:46) (5'-gctctagatgtggtattccacctcttgc-3'). The resulting fragment was restricted with KpnI and XbaI and inserted into the corresponding sites of plasmid pUC16SaadA-Sma (downstream of the aadA gene). A second tobacco plastid DNA fragment (109986 to 111112) was amplified with primers b1-3 (5'-tcccccccgggctcagaggattagagcacg-3') and b1-4 (SEQ ID NO:47) (5'-tcccccccgggagtccgaccacaacgacc-3'), restricted with XmaI, and inserted into the corresponding site of plasmid described above, upstream of the chimeric aadA gene, with the b1-4-end of the fragment next to the rrn16 promoter. In the resulting transformation vector pICFB1

(FIG. 1), the aadA cassette is flanked by plastid sequences, which allow integration of the chimeric gene into the plastome, replacing plastome sequence 111113 to 112060. In addition, this vector can be sustained as an intact plasmid in transformed chloroplasts.

Transformation of N. tabacum Plastids by Biolistic Delivery

Tobacco seeds (*Nicotiana tabacum* cv. *Petite Havana*) were surface sterilized (1 min in 70% ethanol, 10 min in 5% Dimanin C, Bayer, Leverkusen, Germany), washed 3 times for 10 min in sterile $H_2O$ and put on B5 medium (see below). Plants were grown at 25° C. in a 16 h light/8 h dark cycle (0.5-1 $W/m^2$, Osram L85W/25 Universal-White fluorescent lamps).

Six leaves from 4 weeks old, sterile grown *Nicotiana tabacum* plants were cut and transferred to solid RMOP-medium (preparation see below). 35 µl of a gold suspension (0.6 micron particles, Biorad, Hercules, Calif., USA; 60 mg/ml in ethanol) were transferred into a sterile reaction tube (Treff, Fisher Scientific, Ingolstadt, Germany), collected by centrifugation and washed with 1 ml sterile $H_2O$. The gold pellet was resuspended in 230 µl sterile $H_2O$ and 250 µl 2.5 M $CaCl_2$, and 25 µg of plasmid DNA (transformation vector pICFB1) were added. After thoroughly resuspending the mixture, 50 µl 0.1 M spermidin were added, mixed and incubated for 10 min. on ice. The coated gold particles were collected by centrifugation (1 min., 10000 rpm), washed two times with 600 µl ethanol, and finally resuspended in 72 µl ethanol. 5.4 µl of gold-suspension per bombarded leaf were applied to a macrocarrier. Bombardment was carried out with a Bio-Rad (Hercules, Calif., USA) PDS-1000/He Biolistic particle delivery system using the following parameters:

rupture disc 900 psi; helium pressure 1100 psi; vacuum 26-27 inches Hg; macrocarrier at the top level; leaf piece at the third level.

Two days after bombardment leaves were cut into small pieces (ca. 3×3 mm) and transferred to RMOP-medium containing 500 µg/ml spectinomycin. Leaf pieces were cut again and transferred to fresh medium after 2 weeks, then every 3 weeks until no further regenerates appeared. Green regenerates were retrieved and transferred to individual plates. The lines were subjected to repeated cycles of shoot generation by cutting small leaf pieces, which form new regenerates on RMOP-medium with 500 µg/ml spectinomycin. Rooting of selected regenerates was done on B5-medium containing 500 µg/ml spectinomycin.

Molecular Analysis of Plastid Transformants

Isolation of Plant DNA 100 mg of fresh leaf tissue were disrupted in 200 µl AP1 buffer (DNeasy plant mini kit, QIAGEN, Hilden, Germany)+1 µl reagent DX (foaming inhibition, QIAGEN) using mixer mill MM 300 (Retsch, Germany) in a 1.5 ml microcentrifuge tube with one 3 mm tungsten carbide bead (2×1 min at 25 Hz). DNA was then purified using the DNeasy plant mini kit.

Southern Analysis

1 µg of total plant DNA per analysed plant was digested with NcoI and separated on a 1%-agarose gel. DNA was denatured and transferred to a positively charged nylon membrane (Hybond-N+™, Amersham Pharmacia Biotech, UK) according to a standard protocol (Ausubel et al., 1999: Short protocols in molecular biology, Wiley, 4$^{th}$ edition, Unit 2.9A). The membrane was hybridised with an $\alpha^{32}$P-labeled probe in 250 mM sodium phosphate, 7% SDS at 65° and washed with 0.5×SSC, 0.1% SDS at the same temperature. Hybridisation signals were detected using a Phosphoimager (Fujifilm BAS 1500).

A 1131 bp SmaI-fragment from plasmid pICFB1, corresponding to tobacco plastome sequence 109986 to 111112 (and 131514 to 132640) was used as a probe for detection of wild type plastome, transformed plastome and extrachromosomal transformation vector. The fragment was gel purified using the QIAquick Gel Extraction Kit (QIAgen, Hilden, Germany) and labeled with Klenow DNA polymerase and random primers. This probe hybridizes to NcoI-fragments of 17836 bp and 7055 bp in wild type plastid DNA, corresponding to the two copies of the sequence in Inverted Repeat A or B, respectively (FIG. 17, lane 1). In plastome molecules showing integration of the aadA cassette at the targeted locus by homologous recombination, a 4761 bp fragment is detected instead of the 7055 bp fragment due to a new NcoI-site (FIG. 17, lanes 2 and 3). Extrachromosomal transformation vector is detected in its linearized form (6211 bp NcoI-fragment, FIG. 17, lanes 2 and 3). The stronger labeling of this band indicates that the extrachromosomal element is present in a higher copy number than the plastome. The extrachromosomal element was not lost after 5 cycles of repetitive shoot regeneration (FIG. 17, lane 3).

Recovery of pICFB1 From Transplastomic Plants

In order to test the intactness of the transformation vector after propagation in plants, isolated plant DNA from transplastomic plant line 239-2 (3 cycles of repetitive shoot regeneration) was used for transformation of *E. coli* (standard $CaCl_2$ method). This transformation yielded ampicillin-resistant bacteria colonies, which were used for plasmid preparation according to the standard alkaline lysis method. Restriction analysis of plasmids isolated from these colonies showed the identical restriction pattern as the original plastid transformation vector pICFB1 (FIG. 18), demonstrating that the plasmid is propagated in transplastomic plants without recombinatory rearrangements and can be recovered as the original transformation vector.

Example 8

Autonomously Replicating Plastid Transformation Vectors pICF652, pICF653, pICF654, pICF655

In order to construct autonomously replicating plastid transformation vectors which do not allow integration of parts of them into the plastome by flanking homologous recombination events, plasmid pICFB1 was modified to contain only one stretch of plastid sequences. In addition, the terminator sequence of the chimeric aadA gene was removed to allow continuous transcription around the circular plasmid.

Transformation vector pICF652, containing only the left plastid DNA flank of pICFB1 together with a terminatorless aadA sequence (FIG. 19), was created by restriction of plasmid pICFB1 (see example 7) with PstI and subsequent religation.

Transformation vector pICF653, containing only the right flank of pICFB1 together with a terminatorless aadA sequence (FIG. 20), was created by excision of the right flank from pICFB1 with SacI and XbaI and insertion of the T4 DNA polymerase treated 1.1 kb fragment into plasmid pUC16SaadA-Sma (see example 7), restricted with PstI and HindIII and treated with T4 DNA polymerase to remove the terminator sequence. Ligation resulted in two different plasmids carrying the insert in two orientations, named pICF6531 and pICF6532, which were both used for plant transformation.

Transformation vectors pICF654 and pICF655, containing only part of the right flank of pICFB1 together with a terminatorless aadA sequence (FIGS. 21 and 22), were constructed in the same way as pICF653, but using a 0.3 kb ScaI-XbaI fragment from pICFB1 (for pICF654) or a 0.8 kb SacI-ScaI fragment (for pICF655).

The resulting plasmids were used for transformation of tobacco as described in example 7 to define elements essential for autonomous replication in plastids.

The presence and relative copy number of autonomously replicating plastid transformation vectors in plastids of transformed plant lines is examined after three cycles of repetitive shoot regeneration as described in example 7.

Example 9

Autonomously Replicating Plastid Expression Vectors

The fragments conferring autonomous replication in plastids identified according to example 8 are selected for construction of transgene expression cassettes. In these expression cassettes, a gene of interest which contains a 5'-upstream sequence conferring translation, is inserted downstream of the terminator-less aadA-cassette. For this purpose, the uidA coding sequence combined with a 52 bp fragment from the noncoding sequence of the tobacco rps19/rpl22 intergenic region (SEQ ID NO:48) (ctgcagataaaaaaaatctacatgcttatgattcagtagtaggaggcaaacc) is excised from plasmid pIC582 (see example 11) with PstI and KpnI and blunted with T4 DNA polymerase. This fragment is inserted into the T4 DNA polymerase-treated PstI-site of pICF652, giving plastid expression vector pICF652-GUS. Similarly, this fragment is also inserted into the T4 DNA polymerase-treated KpnI-site of pICF653 and pICF655 to create plastid expression vectors pICF653-GUS and pICF655-GUS, respectively. For construction of plastid expression vector pICF654-GUS, said fragment is ligated together with the 0.3 kb ScaI-XbaI fragment into PstI/HindIII-restricted plasmid pUC16SaadA-Sma as described in example 8. The correct orientation of the expression cassette is determined by restriction analysis.

The resulting plasmids are used for transformation of tobacco as described in example 7.

Example 10

Autonomously Replicating Plastid Transformation Vector petAOri1, petAOri2, petAOri3 and petAOri4 Using Selection Based on Photoautotrophy Plasmids petAOri1-4 contain the same replication elements defined in the experiments in example 8, but use the petA gene as a selection marker. These vectors are designed for transformation of petA-deficient plants, restoring the ability for photoautotrophic growth. PetA deficient tobacco plants have been created by transformation with pIC558, where the petA coding sequence was deleted by an aadA cassette. Vector petAOri0 contains a dicistronic operon composed of 5' regulatory elements, the petA coding sequence, a spacer (RBS), and the coding sequence of a gene of interest (uidA). From this vector four derivatives are constructed (petAOri1, petAOri2, petAOri3, petAOri4) with additional DNA fragments conferring autonomous replication.

Construction of Transformation Vector pIC558 for Inactivation of the Plastid Encoded petA Gene All cloning procedures were carried out using standard protocols as described in example 7 and in Ausubel et al., 1999.

Vector pIC558 comprises two flanking sequences derived from the tobacco plastome flanking an aadA-cassette (pUC16SaadA-Sma, Koop et al., 1996, see example 7). The homologous sequences are 5' and 3' regions of the petA gene, 1 kb each. The aadA-cassette replaces the petA gene (962 bp) and 300 bp of the petA 3' region.

Both flanking fragments were amplified by PCR using the following oligonucleotide pairs as primers: oSK13 (SEQ ID NO:7) (5'-GGAATTCCATATGGTATAAAACTCATGT-GTGTAAGAAA-3') and oSK14 (SEQ ID NO:8) (5'-TC-CCCCGGGGGTCCAATCATTGATCGCGAAA-3'), generating a NdeI and a SmaI site at the ends, and oSK15 (SEQ ID NO:49) (5'-TTCCCCGGGTTCTAAATAGAAAGA AAGTCAAATTTG-3') and oSK16 (SEQ ID NO:3) (5'-CATGCATGCGAATGAATAAGATTCTCTTAGCTC-3'), generating a SmaI and a SphI site at the fragment ends. The PCR program used was as follows: 3 min at 94° C., 1 cycle; 45 sec at 94° C., 45 sec at 55° C., 1.5 min at 72° C., 30 cycles; final extension at 72° C. for 10 min. The digested fragments (left/right flank) and the aadA-cassette as SmaI fragment were cloned in one step into the pUC19 vector which was digested with NdeI and SphI. Construct pIC558 was analyzed by restriction experiments. The PCR amplified fragment were sequenced to prove the correct sequence of the flanking regions.

Primary Transformation and Selection of Homoplastomic ΔpetA Mutants

Plastid transformation by particle gun with vector pIC558 and selection was carried out as described in example 7. Homoplastomic petA deficient plants can be used as target for plastid transformation using vectors petAOri1, petAOri2, petAOri3, petAOri4.

Analysis of potential transformants was done as described in example 7.

Construction of Plastid Transformation Vectors petAOri1, petAOri2, petAOri3, petAOri4

Construction of vectors petAOri1, petAOri1, petAOri2, petAOri3, petAOri4 was done in the following way: the petA coding sequence was amplified by PCR using primers 'petAfor' (SEQ ID NO:50) (5' aaaaggarccatgcaaactagaaat-gcttttcttg 3') generating a BamHI restriction site at the 5' end, and 'petArev' (SEQ ID NO:51) (5'ctagaaattcatttcggc-caattgaa 3'). The PCR program used was as follows: 3 min at 94° C., 1 cycle; 45 sec at 94° C., 45 sec at 55° C., 1.5 min at 72° C., 30 cycles; final extension at 72° C. for 10 min. The 5' regulatory elements of vector pUC16SaadA-Sma (Koop et al., 1996, see example 7) were cut out by EcoRI/BamHI digestion. The amplified petA gene fragment and the 5' regulatory elements were cloned in on step into vector pUC19 which was digested with EcoRI and SmaI.

To clone the RBS and the uidA gene downstream to the petA gene, a DNA fragment containing the RBS and the uidA gene was cut out from vector pUC16SRBSuidA (Koop et al., 1996) by KpnI and partial EcoRV digestion. The isolated fragment was blunted and ligated into the vector containing the petA coding sequence and the 5' regulatory elements. As cloning site for this ligation the XbaI site was used, which was blunted as well.

The construct was analyzed by restriction experiments and the PCR amplified petA coding sequence was sequenced to prove the correct sequence.

This vector, petAOri0, was used for the construction of vectors petAOri1, petAOri2, petAOri3, petAOri4: petAOri0 was cut with HindIII and the sticky ends were blunted by T4 DNA polymerase treatment. To construct vector petAOri1 the left flank of vector pICFB1 (see example 7) was cut out by SmaI digestion and ligated into the blunted HindIII site of vector petAOri0. To construct vector petAOri2 the right flank of vector pICFB1 was cut out by SacI/XbaI digestion, blunted and ligated into the blunted HindIII site. To construct vector petAOri3, a 0.3 kb fragment of the right flank of vector pICFB1 was cut out by ScaI/XbaI digestion, blunted and ligated into the blunted HindIII site. To construct vector petAOri4, a 0.8 kb fragment of the right flank of vector pICFB1 was cut out by SacI/ScaI digestion, blunted and ligated into the blunted HindIII site.

The constructs were analyzed by restriction experiments to prove correct cloning. Plastid transformation vector petAOri0 is shown in FIG. 23.

Secondary Transformation and Selection of Reconstituted Homoplastomic ΔpetA Mutants Homoplastomic petA deficient plants can be used as target for plastid transformation using vectors petAOri1, petAOri2, petAOri3, petAOri4. Plastid transformation by particle gun with these vectors is carried out as described in example 7. Selection of transformants is done on RMOP medium with reduced sucrose content (0.3%). Transformants showing reconstitution of petA are able to use photosynthetic energy for growing. Transformants should show also a decrease of hcf (high chlorophyll fluorescence) during increasing cycles of regeneration. Analysis of potential transformants is done as described in example 7.

Example 11

Autonomously Replicating Shuttle Vector pICMFI1

The fragments mediating autonomous replication in plastids (identified according to example 8) are selected for construction of a shuttle vector, which confers stable integration of one or more genes of interest into the plastome.

Construction of Plasmid pICF567-Cloning Vector With Extended Multicloning Site

The multicloning site of plasmid pUC19 between EcoRI and SphI recognition sites was replaced by the synthetic oligonucleotide (SEQ ID NO:52) 5'-AATTCGGGC-CCGTCGACCCTGCA GGCCCGGGGATCCATATGC-CATGGTCTAGATGATCATCACCAT-CATCACTAATCTAGAGAGCTCCTCG AGGCGGCCGCGCATGCATG-3' resulting in plasmid pICF567.

Construction of Plasmid pICF582-Promoterless Plastid Transformation Vector

Plasmid pICF567 was digested with Bsp120I and HindIII. The vector fragment of 2641 bp was purified by agarose gel electrophoresis resulting in fragment pICF567-B/H. The N. tabacum plastome psbA 3'-region from bp 357-1335 was amplified by PCR with the primers (SEQ ID NO:53) 5'-TAT-AGGGCCCAGCTATAGGTTTACATTTTTACCC-3' and (SEQ ID NO:54) 5'-CATGCTGCAGCAAGAAMTAAC-CTCTCCTTC-3' using DNA isolated from Nicotiana tabacum cv. Petite Havana as template. The N. tabacum plastome rpl23'-region from bp 155394-353 was amplified by PCR with the primers (SEQ ID NO:55) 5'-TTTCCTG-CAGTTATTCATGATTGAGTATTC-3' and (SEQ ID NO:56) 5'-CCAGAAAGAAGTATGCTTTGG-3' using DNA isolated from Nicotiana tabacum cv. Petite Havana as template. The amplified psbA 3'-region was digested with Bsp120I and PstI and purified with the PCR-purification-kit from Qiagen (Hilden, Germany) resulting in left-flank-B/P. The amplified rpl2 3'-region was digested with HindIII and PstI and purified with the PCR-purification-kit from Qiagen (Hilden, Germany) resulting in right-flank-P/H. The three fragments pICF567-B/H, left-flank-B/P and right-flank-P/H were ligated simultaneously by T4-ligase resulting in plasmid pICF569.

The E. coli aadA gene was amplified by PCR with the primers (SEQ ID NO:57) 5'-TGAATTCCCATGGCTCGT-GAAGCGG-3' and (SEQ ID NO:58) 5'-TATGGATCCT-TGCCAACTACCTTAGTGATCTC-3' using plasmid pFaadA II (Koop et al., 1996) as template. The PCR product was digested with NcoI and BamHI and ligated into pIC567, previously digested with the same restriction enzymes, resulting in pICF506. The N. tabacum rpl32 3'-UTR was amplified by PCR with the primers(SEQ ID NO:73) 5'-ACAAGAGCTCATAAGTAATAAAACGTTC-GAATAATT-3' and (SEQ ID NO:74) 5'-AATTCCTCGAG-TAGGTCGATGGGGAAAATG-3' using N. tabacum DNA as template. The N. tabacum rpl32 3'-UTR was digested with SacI and XhoI and ligated into pICF506, previously digested with the same restriction enzymes, resulting in pICF519.

The E. coli aadA-sequence and N. tabacum rpl32-3'-UTR was amplified by PCR with the primers (SEQ ID NO:75) 5'-GGATCCATGCGTGMGCGGTTATCGCCG-3' and (SEQ ID NO:76) 5'-AATTCCTCGAGTAGGTCGATGGG-GAAAATG-3'. The E. coli uidA-sequence was amplified by PCR with the primers (SEQ ID NO:61) 5'-CTGGGTACCT-TATTGTTTGCCTCCCTGCTGCG-3' and (SEQ ID NO:62) 5'-CATGCCATGGTCCGTCCTGTAGAA-3' using plasmid pRAJ275 (Mike Bevan, gene bank accession U02456.1) as template. The PCR-products were purified with the PCR-purification-kit from Qiagen resulting in aadA+Trpl32 and uidA respectively. 6 pmol aadA+Trpl32 and 50 pmol oligonucleotide (SEQ ID NO:63) 5'-GGGGTACCAGTTG-TAGGGAGGGATCCATGCGTGAAGC-3' were incubated with Taq-polymerase in 1×-Taq-buffer (MBI) including 0.2 mM dNTPs for 20 min. at 72° C. The resulting fragment contains a 5'-RBS-region resulting in RBS+aadA+Trpl32. It was digested with KpnI and XhoI resulting in RBS+aadA+Trpl32-K/X. The PCR-product uidA was digested with KpnI and NcoI resulting in uidA-N/K. Plasmid pICF567 was digested with PstI and XbaI and purified on a 0.8% agarose gel. The vector fragment at 2690 bp was purified, resulting in pICF567-P/X. 0.6 pmol pICF567-P/X and 300 pmol of the synthetic oligonucleotide Srps19/rpI22 (SEQ ID NO:64) (5'-CTATACCATGGTTTGCCTCCTACTACT-GAATCATAAGCATGTAGATTTTTTTTATCTGCA-3') were incubated with T4-ligase and the second strand was subsequently filled in with Taq-polymerase at 72° C. The resulting product was digested with NcoI and XhoI resulting in pICF567-N/X. 25 fmol pICF567-N/X, 25 fmol uidA-N/K and 25 fmol RBS+aadA+Trpl32-K/X were ligated with T4-ligase resulting in vector pICF576.

Plasmid pICF576 was digested with PstI and Mph1103I. The fragment containing SpsaA/B+uidA+RBS+aadA+Trpl32 was purified on an agarose-gel and ligated into pICF569, previously linearized with PstI, resulting in plasmid pICF582.

Construction of pICMFI1—Vector for Marker-Free Integration

The aadA-gene from pICF582 was removed by digestion with KpnI and SacI. The protruding ends were removed with Klenow-fragment and the vector was relegated with T4-ligase resulting in pICF582A. The psbA B rpl2 flanks including the heterologous uidA-gene were removed from pICF582A with Bsp120I and HindIII. The ends of the psbA - uidA - rpl2-fragment were filled in with Klenow-fragment and ligated into plasmid pICF6521 (see example 8), previously linearized with NdeI and blunted with Klenow-fragment, resulting in pICMF1.

Construction of pICMFI2-Vector for Marker-Free Integration

The construction was carried out as described for pICMFI1, but pICF6531 (see example 8) was used instead of pICF6521.

Construction of pICMFR-Vector for Marker Removal by Recombination

The vector region preceding aadA was amplified from pICMF2 by PCR using primers (SEQ ID NO:65) 5'-gatcggtaccatgttctttcctgcgttat-3' and (SEQ ID NO:66) 5'-gatcggtaccaaagtgtaaagcctggggtg-3'. The PCR-product was digested with KpnI and ligated into pICMFI2, previously linearized with KpnI. The resulting plasmids were sequenced, and a plasmid (pICMFR) was chosen where the orientation of the integrated PCR-product 3' of aadA is the same as in the template region 5' of aadA, so that the aadA sequence is flanked by a direct repeat. The aadA cassette can therefore be excised by homologous recombination between these two sequence elements.

Example 12 aphA-6 μs a Selection Marker for Plastid Transformation of Higher Plants

Vector Cloning a) Construction of Transformation Vectors pICF6061 and pICF6062

Vectors for introducing foreign sequences between the trnN and trnR genes in the inverted repeat region are based on vector pKCZ (Zou, 2001) containing tobacco flanks for homologous recombination (plastome nucleotides 131106-132277 and 132278-133396, according to GenBank accession number Z00044). The aadA expression cassette (Koop et al., 1996) between these flanks was removed by NotI digestion and replaced with an aphA-6 expression cassette obtained as a Bsp120I/NotI fragment from an intermediate construct (pICF603). Since Bsp120I and NotI are compatible, two clones were obtained: pICF6061 (16S rRNA promoter proximal to right flank) and pICF6062 (16S rRNA promoter proximal to left flank). The expression cassette was assembled from PCR amplified plastid regulatory elements 16S rRNA promoter (plastome nucleotides 102571-102659), psbA 5'UTR (1598-1680), rpl323'UTR (115221-115511) and the aphA-6 coding sequence (pSK.KmR, Bateman and Purton 2000).

b) Construction of the Transformation Vector pICF599

For introduction of the aphA-6 expression cassette between petA and orf99 genes in the large single copy region two flanks (plastome nucleotides 63335-65597 and 65598-66597) were amplified by PCR adding desired restriction sites at the fragment ends (NdeI/SmaI and SmaI/SphI). Both flanks were digested with the corresponding enzymes and ligated together with the aphA-6 cassette (prepared as a SmaI fragment) into pUC19 linearized with NdeI/SphI to give pICF599. The expression unit in this plasmid contains the tobacco plastid 16S rRNA promoter, a synthetic ribosomal binding site (RBS, atcactagttgtagggagggatcc, (SEQ ID NO:67) Koop et al. 1996), the aphA-6 coding sequence and the rpl323'UTR in the same reading direction as the petA gene. The aphA-6 cassette was obtained from an intermediate construct based on pUC16S-aadA-SmaI (a modified pUC16S-aadA with an additional SmaI-site for full cassette excision, Koop et al. 1996) in which the aadA coding sequence and the rbcL-3'-UTR from C. reinhardtii were replaced with the aphA-6 coding sequence and the rpl323'UTR from vector pICF606 following NcoI/NotI digestion and religation.

c) Construction of the Transformation Vector pICF637

For introduction of the aphA-6 coding sequence into the upstream position of the ycf3 coding region in the large single copy region, two flanks (plastome nucleotides 45033-46266 and 46269-47205) were amplified by PCR adding desired restriction sites at the fragment ends (SphI/PstI and NcoI/SmaI). Additionally, a synthetic RBS (SEQ ID NO:67) (atcactagttgtagggagggatcc, Koop et al. 1996) was introduced by PCR between the PstI site and the ycf3 coding region serving as translation signal for the ycf3 gene. Both flank fragments were digested with the corresponding enzymes and ligated together with the aphA-6 coding sequence (prepared as a PstI/NcoI fragment from pSK.KmR) into pUC19 linearized with SmaI/SphI to give pICF637. The coding sequences of aphA-6 and ycf3 genes are thus transcribed in the same direction under control of endogenous ycf3 upstream regulatory elements forming a new artificial operon in the transformed plastome.

Plant Material

Surface sterilized seeds of *Nicotiana tabacum* L. cv. *Petit Havana* were germinated on B5 medium (Gamborg et al. 1968) containing 2% sucrose and 0.6% agar. Seedlings were transferred to 700 ml glass jars containing 100 ml B5 medium. Extra ventilation was supplied by foam plug inserts made in the lids. Culture conditions were 16 h day length (approximately 0.5-1.0 W·m$^{-1}$, Sylvania standard F58W/125-T8 Universal-White lamps) at 27+/−1° C.

Protoplast Isolation and Grid Embedding

Protoplast isolation and alginate embedding was made essentially as described in Dovzhenko et al. (1998) and Koop et al. (1996) with slight modifications. Prior to embedding protoplasts were resuspended in F-PCN at a density of 1.7×10$^5$ protoplasts/ml and then mixed with an equal volume of alginate to give a final plating density of 5.5×10$^4$ per grid.

Selection Conditions

The conditions for selecting kanamycin-resistant regenerants after grid bombardment and PEG transformation were determined by a selection trial placing grids containing eight days old alginate-embedded micro colonies on RMOP medium and different concentrations of kanamycin (0, 10, 25, 50, 75, 100 mg/l). Evaluation of an appropriate selection condition was made after 4 weeks of incubation in the culture room.

Transformation and Selection a) Leaf bombardment: Three to four weeks old tobacco leaves (~45×55 mm) were precultured for one day on RMOP medium and then bombarded with DNA coated gold particles as described in Mühlbauer et al. (2002) using a DuPont particle gun. Two days after shooting leaves were cut in small peaces (2×2 mm) and transferred to selection medium (RMOP+25-50 mg/l kanamycin. Transfer to fresh medium was performed routinely every 3-4 weeks.

b) Grid bombardment: Alginate-embedded protoplasts were cultured for 6-7 days in liquid medium (F-PCN) until they reached a the 32-64 cell stage. After draining the grids they were transferred to solid medium (RMOP) and precultured for one day before they were used for bombardment. Gold loading, bombardment and selection were performed as described above.

c) PEG transformation: Polyethylene glycol-mediated DNA transfer into chloroplasts was made as described in Koop et al. (1996) and Kofer et al. (1998). Selection of transformed cells was started 7 days after transformation by transferring the alginate-embedded protoplasts to agar-solidified RMOP medium containing 25-50 mg/l kanamycin. Transfer to fresh medium was made every 3 weeks for a total period of up to 12 weeks of selection.

In order to amplify transformed plastomes and eliminate wild-type plastomes, primary transformants (cycle-0) were subjected to several additional rounds of regeneration (small leaf explants, 2×2 mm) on selective medium, here designated as cycle-1, cycle-2 etc.

DNA Isolation

Vector DNA was isolated using plasmid preparation kits (Qiagen, Hilden, Germany) according to the manufacturer's protocol. DNA prepared for PEG transformation was additionally Na-acetate/ethanol precipitated and dissolved in TE buffer pH 5.6. Total plant DNA was isolated using a plant DNA isolation kit (Qiagen DNeasy). Callus or leaf tissue (100-200 mg) was macerated in a 1.5 ml Eppendorf tube using Mixer Mill MM 300 (Retsch, Haan, Germany) and a tungsten carbide bead (3 mm) as described in the manufacturer's protocol. DNA was eluted in 100 µl elution buffer and the concentration determined with a fluorometer (VersaFluor, Biorad, München, Germany) and a fluorescent DNA quantification kit (Biorad).

Determination of Kanamycin Resistance Levels in Transformants and Progeny

Kanamycin resistance levels of different transformants were determined by cutting leaf discs with a sterile cork borer (5 mm in diameter) and placing them on RMOP medium containing various kanamycin concentrations (0-200 mg/l). The growth of explants was evaluated after 4 weeks of culture.

Progeny analysis (T1) was performed with seeds collected from wild type and self-pollinated transformants grown in the glasshouse. Seed from multiple seedpods were surface sterilized and germinated on agar-solidified B5 medium or B5 medium containing 200 mg/l kanamycin. The appearance of the seedlings was evaluated after 2 weeks of culture under standard culture conditions.

Results aphA-6 Gene Expression in *E. coli*

Prior to plant transformation functionality of all vectors was tested in *E. coli*. Plasmids pICF599, pICF6061/2 (aphA-6 gene under control of the 16S rRNA promoter) conferred resistance to at least 50 mg/l kanamycin, while pICF637 conferred resistance to only 25 mg/l kanamycin (ycf3-promoter driven aphA-6 gene).

Determination of Kanamycin Selection Conditions

In order to determine a suitable kanamycin selection level for alginate-embedded protoplast-derived micro colonies, grids were placed on RMOP medium containing various kanamycin concentrations (0-100 mg/l). A kanamycin level below 25 mg/l did not sufficiently suppress development, whereas levels above 50 mg/l were too stringent, causing extensive browning and limited colony growth. Therefore, initially a level of 25 mg/l kanamycin was used for selecting transformants after grid bombardment. The selection level was increased to 50 mg/l kanamycin once it was established that the 16S rRNA-promoter driven aphA-6 gene can confer resistance up to 200-500 mg/l kanamycin. PEG treated protoplasts were selected on a similar kanamycin concentration.

Recovery of Kanamycin Resistant Regenerants a) Grid Bombardment

Bombardment of protoplast-derived micro colonies was performed with the aphA-6 gene in combination with kanamycin selection. Critical for the success of the technique were grids containing micro colonies of the correct developmental stage (32-64 cells) and a high plating efficiency. Table 2 summarizes the results obtained from all transformation experiments using the aphA-6 gene as a selection marker. Kanamycin-resistant regenerants were obtained over a 12 week selection period following bombardment. Occasionally, early events were visible after only 24 days of culture.

b) PEG Transformation

The aphA-6 gene was used for the recovery of kanamycin-resistant transformants following PEG-mediated DNA delivery. From two experiments made with pICF599 a number of regenerants were obtained following selection of grids on 25 mg/l kanamycin (see Table 2). The time period for the appearance of the resistant regenerants was generally similar to that described for the grid bombardment.

One problem encountered from early grid selection experiments using 25 mg/l kanamycin was the regeneration of a number of untransformed escapes. In order to avoid the problem of analyzing untransformed lines all green regenerants were removed from grids and pre-selected by culturing on fresh selection medium. Transformed lines remained green and developed normally, while escapes rapidly bleached. At a higher kanamycin concentration 50 mg/l a significantly lower number of regenerants were generally observed.

PCR Analysis

The first analysis of green regenerants was made by PCR analysis using material from grid bombardments and PEG transformations (see Table 1 for primer sequences). In order to show the presence of the aphA-6 gene initial analysis was made with primers oFCH168 and oFCH169. From 20 tested lines 19 gave the expected fragment of 480 bp. To prove correct integration of the aphA-6 gene into the different plastome insertion sites PCR was performed using one internal aphA-6-primer and a second primer located outside one of the flanks used for homologous recombination. pICF6061 and pICF6062 contain the same aphA-6 expression cassette which is cloned in different orientations with respect to the flanking sequences. As such, two different primer combinations (oSH58 and oFCH169, oSH58 and oFCH168) were necessary to show integration between trnN and trnR in the tobacco plastome. For the analysis of regenerants T101-1 and T177-1 (pICF6061-transformants) the primer combination oSH58 and oFCH169 was used giving the expected band of 1978 bp in both cases. For the opposite orientation, regenerant T349-1 (pICF6062-transformant) was analyzed using primers oSH58 and oFCH168 and resulting in the correct product of 2297 bp. Introduction of the aphA-6 gene between petA and orf99 is shown for regenerants T330-2 and T330-4 (pICF599-transformants). For this analysis primers oSK116 and oFCH169 were used resulting in a 2961 bp fragment. With regard to the third insertion site, correct plastome integration results in the formation of an artificial operon with the aphA-6 coding region under the control of the ycf3 regulatory elements. The primer combination oFCH27 and oFCH168 was used for analyzing regenerants T109-1, T109-2 and T109-3 (pICF637-transformants) and resulted in expected fragments of 2239 bp. Control reactions were performed with each of the above mentioned primer combinations using DNA prepared from a wild-type plant.

In 7 transformation experiments a total of 18 independent transformants were recovered from 35 bombarded grids, on average 1 transformant from every 2 grids. From two PEG transformation experiments a total of 9 transformants were obtained from 18 grids, on average 1 transformant from every 2 grids. Importantly, all three of the new plastome insertion sites described in this paper function as we were able to obtain transformants in all cases. The general transformation efficiency with each of the four vectors was comparable, even with experiments involving pICF637, where expression of the aphA-6 coding region is controlled by regulatory elements present in the plastome and not on the transformation vector.

Southern Analysis

PCR-positive lines from all three insertion sites were further analyzed by Southern hybridization to confirm the predicted plastome integration. Probes were chosen that hybridized to both, transformed and wild-type plastomes in order to estimate the ratio of untransformed and transformed plastomes in these lines. Total DNA from pICF6061-transformants and an untransformed control were digested with BamHI and hybridized with probe P1 covering the left flank (1117 bp). The control showed a fragment of 7076 bp, whereas both transformants (T1011-1, T177-1) gave the expected fragment of 2753 bp due to the aphA-6 expression cassette carrying an additional BamHI site. For the analysis of pICF599-transformants total DNA was restricted with BglII and hybridized with probe P2, a 300 bp fragment of the left flank. The wild-type control showed a fragment of 7661 bp, whereas signals of 4426 bp (lines T330-2 and T330-4) were generated from transgenic plastomes due to the presence of a BglII site in the aphA-6 expression cassette. In the third case, DNA from pICF637-transformants and an untransformed control were XmaJI digested and analyzed by probing with P3, a 518 bp fragment located outside of the right flank. The wild-type control showed a band of 2198 bp, whereas in all three transformed lines T109-1, T109-2 and T109-3 a larger fragment of 3028 bp was observed, due to the insertion of the aphA-6 coding sequence.

Depending on the number of cycles of regeneration on selection, differences in the ratio of transformed and untransformed plastomes are seen. In the case of transformed line T330-4, a pICF599-transformant, plant tissue from cycle-0 was analyzed on the Southern blot and as such is clearly heteroplastomic with respect to wild-type plastome content whereas in line T330-2 (cycle-1) wild-type plastomes are almost undetectable. Also transformants analyzed from later cycles (cycle-IV, pICF637-transformants and cycle-V, pICF6061-transformants) that had been in culture for more than 6 months still showed faint signals of comparable size of the wild-type. This time period is sufficient for production of homoplastomic lines.

aphA-6 Expression Studies

Studies of aphA-6 expression in leaf explants were made with plants that had been regenerated on selection so that the transgenic plastome content in each line was comparable based on Southern analysis. Variations regarding kanamycin tolerance were observed in transformants containing a 16S rRNA promoter driven aphA-6 gene (pICF6061-transformants) compared to those carrying aphA-6 under the control of the ycf3 regulatory elements (pICF637-transformants). Leaf explants were placed on RMOP medium containing 0, 25 and 200 mg/l kanamycin and evaluated after 4 weeks. Transformants from pICF6061 showed comparable growth on all tested levels. In contrast, pICF637-transformants were unable to grow on the highest level of kanamycin but did show proliferation on 25 mg/l. The 16S rRNA promoter is the strongest plastid promoter described to date, whereas the strength of the promoter driving ycf3 expression is unknown. Control explants from wild-type leaves failed to grow on any of the chosen kanamycin concentrations. In an additional experiment the upper limits of kanamycin resistance were determined showing a tolerance level of 500 mg/l for plants carrying a 16S rRNA promoter-driven aphA-6 gene and 50 mg/l for plants with the aphA-6 marker under the control of the ycf3 regulatory elements.

Analysis of Progeny

Transplastomic plants selected in vitro after multiple cycles of kanamycin selection were transferred to the glasshouse for seed collection following self-pollination. Wild-type seeds germinated normally on B5 medium but bleached following germination on B5 medium containing 200 mg/l kanamycin. In contrast, seeds from pICF599- and pICF637-transformants germinated and remained green on 200 mg/l kanamycin but were slightly less vigorous than transgenic seeds plated on non-selective medium. Neither of the transformed lines showed any segregation with the respect to kanamycin resistance indicating both to be homoplastomic.

TABLE 1

Primers for PCR analysis and probe synthesis

| Name | Sequence | Binding position |
|---|---|---|
| Primers used for analysis of kanamycin-resistant regenerants | | |
| oFCH168 | TCAGTCGCCATCGGATGTTT (SEQ ID NO:27) | 168-187[a] |
| oFCH169 | ACCAATCTTTCTTCAACACG (SEQ ID NO:28) | 628-647[a] |

TABLE 1-continued

Primers for PCR analysis and probe synthesis

| Name | Sequence | Binding position |
| --- | --- | --- |
| oFCH27 | TGCTCAAGACTTTAGTGGATC (SEQ ID NO:25) | 44799-44819[b] |
| oSH58 | TATTCCGACTTCCCCAGAGC (SEQ ID NO:5) | 109138-109157[b] |
| oSK116 | AAAATAGATTCATTAGTCCGATACC (SEQ ID NO:13) | 63308-63332[b] |

Primers used for generation of DIG-labeled southern-probes

| | | |
| --- | --- | --- |
| oSH140 | CTGGTCGACTTGCTGTTGCATCGAAAGAG (SEQ ID NO:68) | 111500-111520[b] and 131106-131126[b] |
| oSH141 | AGAGCGGCCGCAATTGTGACCTCTCGGGAG (SEQ ID NO:69) | 110348-110367[b] and 132259-132278[b] |
| oSK71 | TCCCCCGGGTAGAAAACTATTGATACGTCTTATGG (SEQ ID NO:10) | 65572-65597[b] |
| oSK111 | AAAACTGCAGATTCGCAGATTTGTCGACATCAA (SEQ ID NO:70) | 65298-65320[b] |
| oFCH64 | GAATTACCAAACCATTTGACCC (SEQ ID NO:23) | 47646-47667[b] |
| oFCH69 | CATTGGAACTGCTATGTAGGC (SEQ ID NO:24) | 47149-47169[b] |

All primer sequences are given in the 5' to 3' orientation.
[a] aphA-6 gene sequence according to NCBI accession number X07753
[b] tobacco plastome sequence according to NCBI accession number Z00044

TABLE 2

Chloroplast transformation experiments

| Transformation number | Vector | Method* | Target Tissue | Analyzed regenerants | Trans- formants |
| --- | --- | --- | --- | --- | --- |
| 95 | pICF6062 | PG | micro colonies (4 grids) | 0 | 0 |
| 101 | pICF6061 | PG | micro colonies (3 grids) | 1 | 1 |
| 109 | pICF637 | PG | micro colonies (4 grids) | 4 | 4 |
| 177 | pICF6061 | PG | micro colonies (8 grids) | 1 | 1 |
| 330 | pICF599 | PEG | protoplasts (9 grids) | 5 | 4 |
| 348 | pICF6061 | PG | micro colonies (6 grids) | 5 | 5 |
| 349 | pICF6062 | PG | micro colonies (5 grids) | 3 | 3 |
| 350 | pICF599 | PG | micro colonies (6 grids) | 6 | 6 |
| 376 | pICF599 | PEG | protoplasts (9 grids) | 5 | 5 |

*PG particle gun, PEG polyethylene glycol

REFERENCES

U.S. Pat. No. 5,877,402
U.S. Pat. No. 5,693,507
U.S. Pat. No. 5,451,513
Ausubel et al., 1999: Short protocols in molecular biology, Wiley, 4th edition.
Aviv, D and Galun, E 1985, J. Hered. 76:135-136.
Bateman and Purton (2000) Mol. Gen. Genet. 263, 404-410.
Carrer H., Hockenberry T. N., Svab Z., Maliga P. (1993), Mol. Gen. Genet., 241, 49-56.
Daniell, H., Muthukumar, B., and Lee, S. B. (2001) Curr. Genet. 39, 109-116.
Daniell, H., et al. (1990) Proc. Natl. Acad. Sci. USA 87, 88-92
De Santis-Maciossek G, Kofer W, Bock A, Schoch S, Maier R M, Wanner G, Rüdiger W, Koop H U, Herrmann R G 1999, Plant J. 199918:477-89
Dovzhenko A, Bergen U, Koop HU 1998, Protoplasma 204: 114-18
Eibl, C., et al. (1999) Plant J., 19, 333-345.
Galvin S. B., 1998, Curr. Opin. Biotechnol., 9, 227-232.
Golds, T., Maliga, P., and Koop, H.-U. (1992) Biotechnology 11, 95-97 Goldschmidt-Clermont, M. (1991) Nucleic Acids Research 19, 4083-4089
Gray M. W., Origin and Evolution of Plastid Genomes and Genes, in: Bogorad L. and Vasil I. K. (eds.), Cell Culture and Somatic Cell Genetics of Plants, Volume 7A, Academic Press, San Diego, 1991.
Heifetz, P., 2000, Biochimie, 82, 655-666.
Iamtham, S, and Day, A., 2000, Nature Biotechnology 18, 1172-1176.
Koop et al. (1996) Planta 199, 193-201
Krause K, Maier R M, Kofer W, Krupinska K, Herrmann R G 2000, Mol. Gen. Genet. 263: 1022-1030

Maliga, P., Carrer, H., Kanevski, I., Staub, J., and Svab, Z. (1993) Phil. Trans. R. Soc. Lond. B 342, 203-208

Kunnimalaiyaan and Nielsen (1997) J. Plant Biochem. Biotechnol. 6,1-7

Marechal-Drouard L., Kuntz M., Weil J. H., tRNAs and tRNA Genes of Plastids, in: Bogorad L. and Vasil I. K. (eds.), Cell Culture and Somatic Cell Genetics of Plants, Volume 7A, Academic Press, San Diego, 1991.

Martin et al. (1988) Mol. Microbiol. 2, 615-625.

Palmer J. D., Plastid Chromosomes: Structure and Evolution, in: Bogorad L. and Vasil I. K.(eds.), Cell Culture and Somatic Cell Genetics of Plants, Volume 7A, Academic Press, San Diego, 1991.

The *Arabidopsis* Genome Initiative, 2000, Nature, 408, 796-815.

Sidorov, V. A., Kasten, D., Pang, S.-Z., Hajdukiewicz, P. T. J., Staub, J. M., and Nehra, N. S. (1999) Plant J. 19, 209-216

Ruf S Kossel H, Bock R1997, J. Cell Biol. 139: 95-102.

Staub and Maliga (1994) Proc. Natl. Acad. Sci. USA 91, 7468-7472

Staub and Maliga (1995) Mol. Gen. Genet. 249, 37-42

Suzuki et al. (1997) Plant J. 11, 635-648

Svab, Z., Hajdukiewicz, P., and Maliga, P. (1990) Proc. Natl. Acad. Sci. USA 87, 8526-8530.

Svab, Z., and Maliga, P. (1993) Proc. Natl. Acad. Sci. USA 90, 913-917

Zoubenko, O. V., Allison, L. A., Svab, Z., and Maliga, P. (1994) Nucl. Acids Res. 22, 3819-3824

Zou Z. (2001), Ph. D. Dissertation for Ludwigs-Maximilian-Universität, Munich

SEQUENCE LISTING

```
<160> NUMBER OF SEQ ID NOS: 70

<210> SEQ ID NO 1
<211> LENGTH: 1127
<212> TYPE: DNA
<213> ORGANISM: Nicotiana tabacum

<400> SEQUENCE: 1
gctcagagga ttagagcacg tggctacgaa ccacggtgtc gggggttcga atccctcctc      60
gcccacaacc ggcccaaaag ggaagtacct ttccctctgg gggtaggaaa atcatgatcg     120
ggatagcgaa ccaaaagcta tggaacttgg gtgtgggtct tttgtcgaaa tggaatggct     180 tttcttttc tctttttatt tatcgtgaat gggggaatca ttacacatag tatgcccggt     240
cagcatattt ttttgtttta cgccccgtaa ctcttcctca gccaggcttg ggcagaatag     300
cagagcaagt attagtagca taacaaaaaa gccttcctcg tcattaatat ctttgctcgc     360
ggcaattgtg acctctcggg agaatcgatg actgcatctt tgatgcagtg ctagtatatc     420
tgagacttct taattggcta gttgtaaata gccccagggc tatggaacaa aggattatct     480
cggacctaga ccgaggtatt gatggtgatt ttctaatctc gcagaacaga atgtgatacg     540
atgagataga atgcaataga aacaaagaca gggaacgggt tacctactct taacgggcaa     600
agcgagcccc tttattctga attctttaat tcagaatcaa tcaaatctcc ccaagtagga     660
ttcgaaccta cgaccaatcg gttaacagcc gaccgctcta ccactgagct actgaggaac     720
aacaggagat tcgatctcat agagttcaat tcccgttccc aacccatgac caatatgagc     780
tcgaagcttc cttcgtaact cccggaactt cttcgtagtg gctcccttac atgcctcatt     840
tcagagggaa cctcaaagtg gctctatttc attatattcc atccatatcc caattccatt     900
catttaatat ccctttggtg tcattgacat aacagatgtc gtttctagtc tatctctttc     960
tatttctttt ctatatatgg aaagttcaaa aatcatcata taataatcca gaaattgcaa    1020
tagaaaagaa ataagggagg tttgtgatga tttttcaatc ttttctacta ggtaatctag    1080
tatccttatg catgaagata atcaattcgg tcgttgtggt cggactc                  1127

<210> SEQ ID NO 2
<211> LENGTH: 1017
<212> TYPE: DNA
<213> ORGANISM: Nicotiana tabacum
```

-continued

```
<400> SEQUENCE: 2
gaatttgatt cacaaagttg aaaagagtaa gtaataaact aataaaaaga ttgaaacata      60
agctaaatac aagaaaagat aagaagagat gcgtccgccc cctatatatt tgataccttc     120
tcctacaatg aaactaataa ccccaacccc gttagtcatc ccatcaatta ctcgtcgatc     180
aaaaaaatga gtaaattcag ctaatcctct tatcccacca actaagaatc ttgtataaaa     240
agcatctatg taagcacgat tatatgacca atcatatatg ccatttataa ttttgtccca     300
cagaattctc ttaggaccct ttttaacaaa agaattaatt aactcaaaat ttttttaaaga    360 agaataaatg ggtttatata aaaggatgc tataaatatt ccgaaataag ctatactgac      420
tgaaagaact gcatccttta aaaattcatt ccaatccatc gaattattcg acttttgatg     480
caaaagattt atagatggag ctaaccattt cgataatata tccaaattcc ctccctcttg     540
gttgaaagga attcctatag atccaacaaa caaagtaaag agtcctaata caaatattgg     600
gaatagcata gtattgtccg attcataagg ataggaataa accgctttat gctcaaaatg     660
agcaatagtc ataaaaggtc gtgtcatctt tcttccattt ttatcaattg gatatttagt     720
ttttgcaaaa aaataagtac tttcattatt attcatagtt aataaacaag agttttttctt    780 aactccgttt ttaccccata gagatattga atagaagggg gttttttgtt tcccaccata    840
atttggaaaa tgagcgttta aatgcccttc aaaagtaagt aaatagatcc gaaacatata    900
aaatgcggtt aatcccgccg tggcccaagc tattattgcg aaaattggcg aatacaacca    960
actatcatta agaatttcat ctttggacca aaaacaagca agaggtggaa taccaca       1017

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
ctatcagagg tagttggcgt c                                                21

<210> SEQ ID NO 4
<211> LENGTH: 21
<212> TYPE: DNA
<213> ORGANISM: Artificial Sequence
<220> FEATURE:
<223> OTHER INFORMATION: PCR primer

<400> SEQUENCE: 4
cactacattt cgctcatcgc c                                                21

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
tattccgact tccccagagc                                                  20

<210> SEQ ID NO 6
<211> LENGTH: 17
<212> TYPE: DNA
<213> ORGANISM: Artificial Sequence
<220> FEATURE:
```

```
<223> OTHER INFORMATION: PCR primer

<400> SEQUENCE: 6
ggcatcagag cagattg                                              17

<210> SEQ ID NO 7
<211> LENGTH: 38
<212> TYPE: DNA
<213> ORGANISM: Artificial Sequence
<220> FEATURE:
<223> OTHER INFORMATION: PCR primer

<400> SEQUENCE: 7
ggaattccat atggtataaa actcatgtgt gtaagaaa                       38

<210> SEQ ID NO 8
<211> LENGTH: 31
<212> TYPE: DNA
<213> ORGANISM: Artificial Sequence
<220> FEATURE:
<223> OTHER INFORMATION: PCR primer

<400> SEQUENCE: 8
tcccccgggg gtccaatcat tgatcgcgaa a                              31

<210> SEQ ID NO 9
<211> LENGTH: 33
<212> TYPE: DNA
<213> ORGANISM: Artificial Sequence
<220> FEATURE:
<223> OTHER INFORMATION: PCR primer

<400> SEQUENCE: 9
catgcatgcg aatgaataag attctcttag ctc                            33

<210> SEQ ID NO 10
<211> LENGTH: 35
<212> TYPE: DNA
<213> ORGANISM: Artificial Sequence
<220> FEATURE:
<223> OTHER INFORMATION: PCR primer

<400> SEQUENCE: 10
tcccccgggt agaaaactat tgatacgtct tatgg                          35

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
tgctggccgt acatttgtac g                                         21

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
cactacattt cgctcatcgc c                                         21
```

```
<210> SEQ ID NO 13
<211> LENGTH: 25
<212> TYPE: DNA
<213> ORGANISM: Artificial Sequence
<220> FEATURE:
<223> OTHER INFORMATION: PCR primer

<400> SEQUENCE: 13
aaaatagatt cattagtccg atacc                                          25

<210> SEQ ID NO 14
<211> LENGTH: 18
<212> TYPE: DNA
<213> ORGANISM: Artificial Sequence
<220> FEATURE:
<223> OTHER INFORMATION: PCR primer

<400> SEQUENCE: 14
caggaaacag ctatgacc                                                  18

<210> SEQ ID NO 15
<211> LENGTH: 31
<212> TYPE: DNA
<213> ORGANISM: Artificial Sequence
<220> FEATURE:
<223> OTHER INFORMATION: PCR primer

<400> SEQUENCE: 15
gactagtcta gaaattcatt tcggccaatt g                                   31

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
tcacaccgat accatcagcg                                                20

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
attgtttgcc tccctgctgc                                                20

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18
aatcgtacca gtctctactg g                                              21

<210> SEQ ID NO 19
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 19
gtagcaatcc attctagaat                                                   20

<210> SEQ ID NO 20
<211> LENGTH: 21
<212> TYPE: DNA
<213> ORGANISM: Artificial Sequence
<220> FEATURE:
<223> OTHER INFORMATION: PCR primer

<400> SEQUENCE: 20
cggaaagaga gggattctaa c                                                 21

<210> SEQ ID NO 21
<211> LENGTH: 21
<212> TYPE: DNA
<213> ORGANISM: Artificial Sequence
<220> FEATURE:
<223> OTHER INFORMATION: PCR primer

<400> SEQUENCE: 21
gaagtttctt tctttgctac a                                                 21

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
tacgcttttt gaaggtgaag t                                                 21

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
gaattaccaa accatttgac cc                                                22

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
cattggaact gctatgtagg c                                                 21

<210> SEQ ID NO 25
<211> LENGTH: 21
<212> TYPE: DNA
<213> ORGANISM: Artificial Sequence
<220> FEATURE:
<223> OTHER INFORMATION: PCR primer

<400> SEQUENCE: 25
tgctcaagac tttagtggat c                                                 21

<210> SEQ ID NO 26
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 26
tattccgact tccccagagc                                                    20

<210> SEQ ID NO 27
<211> LENGTH: 20
<212> TYPE: DNA
<213> ORGANISM: Artificial Sequence
<220> FEATURE:
<223> OTHER INFORMATION: PCR primer

<400> SEQUENCE: 27
tcagtcgcca tcggatgttt                                                    20

<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
accaatcttt cttcaacacg                                                    20

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
tactattatt tgattagatc                                                    20

<210> SEQ ID NO 30
<211> LENGTH: 21
<212> TYPE: DNA
<213> ORGANISM: Artificial Sequence
<220> FEATURE:
<223> OTHER INFORMATION: PCR primer

<400> SEQUENCE: 30
taattactga atcgcttccc a                                                  21

<210> SEQ ID NO 31
<211> LENGTH: 21
<212> TYPE: DNA
<213> ORGANISM: Artificial Sequence
<220> FEATURE:
<223> OTHER INFORMATION: PCR primer

<400> SEQUENCE: 31
ttaaaactta tttttgcta a                                                   21

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
```
tatgaaaggc aagccgaca                                               20

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
taaatcccta actttaggtc                                              20

<210> SEQ ID NO 34
<211> LENGTH: 20
<212> TYPE: DNA
<213> ORGANISM: Artificial Sequence
<220> FEATURE:
<223> OTHER INFORMATION: PCR primer

<400> SEQUENCE: 34
tgagtcagag atatatggat                                              20

<210> SEQ ID NO 35
<211> LENGTH: 21
<212> TYPE: DNA
<213> ORGANISM: Artificial Sequence
<220> FEATURE:
<223> OTHER INFORMATION: PCR primer

<400> SEQUENCE: 35
ggtactatta tttgattaga t                                            21

<210> SEQ ID NO 36
<211> LENGTH: 21
<212> TYPE: DNA
<213> ORGANISM: Artificial Sequence
<220> FEATURE:
<223> OTHER INFORMATION: PCR primer

<400> SEQUENCE: 36
taattactga atcgcttccc a                                            21

<210> SEQ ID NO 37
<211> LENGTH: 21
<212> TYPE: DNA
<213> ORGANISM: Artificial Sequence
<220> FEATURE:
<223> OTHER INFORMATION: PCR primer

<400> SEQUENCE: 37
ttaaaactta tttttttgcta a                                           21

<210> SEQ ID NO 38
<211> LENGTH: 36
<212> TYPE: DNA
<213> ORGANISM: Artificial Sequence
<220> FEATURE:
<223> OTHER INFORMATION: PCR primer

<400> SEQUENCE: 38
ggaattccat atgtgtgatc tgcctcaaac ccacag                            36

<210> SEQ ID NO 39
<211> LENGTH: 33
<212> TYPE: DNA
<213> ORGANISM: Artificial Sequence

```
<220> FEATURE:
<223> OTHER INFORMATION: PCR primer

<400> SEQUENCE: 39
cggggtacct cattccttac ttcttaaact ttc                              33

<210> SEQ ID NO 40
<211> LENGTH: 24
<212> TYPE: DNA
<213> ORGANISM: Artificial Sequence
<220> FEATURE:
<223> OTHER INFORMATION: PCR primer

<400> SEQUENCE: 40
ccgaattcgc cgtcgttcaa tgag                                        24

<210> SEQ ID NO 41
<211> LENGTH: 20
<212> TYPE: DNA
<213> ORGANISM: Artificial Sequence
<220> FEATURE:
<223> OTHER INFORMATION: PCR primer

<400> SEQUENCE: 41
cacgatatcg cccggagttg                                             20

<210> SEQ ID NO 42
<211> LENGTH: 27
<212> TYPE: DNA
<213> ORGANISM: Artificial Sequence
<220> FEATURE:
<223> OTHER INFORMATION: PCR primer

<400> SEQUENCE: 42
ctcgatatca ctagttgtag ggaggga                                     27

<210> SEQ ID NO 43
<211> LENGTH: 18
<212> TYPE: DNA
<213> ORGANISM: Artificial Sequence
<220> FEATURE:
<223> OTHER INFORMATION: PCR primer

<400> SEQUENCE: 43
gtgccatgga tccctcct                                               18

<210> SEQ ID NO 44
<211> LENGTH: 29
<212> TYPE: DNA
<213> ORGANISM: Artificial Sequence
<220> FEATURE:
<223> OTHER INFORMATION: PCR primer

<400> SEQUENCE: 44
tccccccggg ctcagaggat tagagcacg                                   29

<210> SEQ ID NO 45
<211> LENGTH: 28
<212> TYPE: DNA
<213> ORGANISM: Artificial Sequence
<220> FEATURE:
<223> OTHER INFORMATION: PCR primer

<400> SEQUENCE: 45
ggggtaccga atttgattca caaagttg                                    28
```

```
<210> SEQ ID NO 46
<211> LENGTH: 28
<212> TYPE: DNA
<213> ORGANISM: Artificial Sequence
<220> FEATURE:
<223> OTHER INFORMATION: PCR primer

<400> SEQUENCE: 46
gctctagatg tggtattcca cctcttgc                                      28

<210> SEQ ID NO 47
<211> LENGTH: 28
<212> TYPE: DNA
<213> ORGANISM: Artificial Sequence
<220> FEATURE:
<223> OTHER INFORMATION: PCR primer

<400> SEQUENCE: 47 tcccccggg agtccgacca caacgacc                                       28

<210> SEQ ID NO 48
<211> LENGTH: 52
<212> TYPE: DNA
<213> ORGANISM: Nicotiana tabacum

<400> SEQUENCE: 48
ctgcagataa aaaaaatcta catgcttatg attcagtagt aggaggcaaa cc           52

<210> SEQ ID NO 49
<211> LENGTH: 36
<212> TYPE: DNA
<213> ORGANISM: Artificial Sequence
<220> FEATURE:
<223> OTHER INFORMATION: PCR primer

<400> SEQUENCE: 49
ttccccgggt tctaaataga aagaaagtca aatttg                             36

<210> SEQ ID NO 50
<211> LENGTH: 36
<212> TYPE: DNA
<213> ORGANISM: Artificial Sequence
<220> FEATURE:
<223> OTHER INFORMATION: PCR primer

<400> SEQUENCE: 50
aaaaggarcc atgcaaacta gaaatgcttt ttcttg                             36

<210> SEQ ID NO 51
<211> LENGTH: 26
<212> TYPE: DNA
<213> ORGANISM: Artificial Sequence
<220> FEATURE:
<223> OTHER INFORMATION: PCR primer

<400> SEQUENCE: 51
ctagaaattc atttcggcca attgaa                                        26

<210> SEQ ID NO 52
<211> LENGTH: 113
<212> TYPE: DNA
<213> ORGANISM: Artificial Sequence
<220> FEATURE:
<223> OTHER INFORMATION: extended multicloning site of pICF567

<400> SEQUENCE: 52
```

```
aattcgggcc cgtcgaccct gcaggcccgg ggatccatat gccatggtct agatgatcat      60
catcaccatc atcactaatc tagagagctc ctcgaggcgg ccgcgcatgc atg             113
```

<210> SEQ ID NO 53
<211> LENGTH: 34
<212> TYPE: DNA
<213> ORGANISM: Artificial Sequence
<220> FEATURE:
<223> OTHER INFORMATION: PCR primer

<400> SEQUENCE: 53

```
tatagggccc agctataggt ttacattttt accc                                  34
```

<210> SEQ ID NO 54
<211> LENGTH: 31
<212> TYPE: DNA
<213> ORGANISM: Artificial Sequence
<220> FEATURE:
<223> OTHER INFORMATION: PCR primer

<400> SEQUENCE: 54

```
catgctgcag caagaaaata acctctcctt c                                     31
```

<210> SEQ ID NO 55
<211> LENGTH: 30
<212> TYPE: DNA
<213> ORGANISM: Artificial Sequence
<220> FEATURE:
<223> OTHER INFORMATION: PCR primer

<400> SEQUENCE: 55

```
tttcctgcag ttattcatga ttgagtattc                                       30
```

<210> SEQ ID NO 56
<211> LENGTH: 21
<212> TYPE: DNA
<213> ORGANISM: Artificial Sequence
<220> FEATURE:
<223> OTHER INFORMATION: PCR primer

<400> SEQUENCE: 56

```
ccagaaagaa gtatgctttg g                                                21
```

<210> SEQ ID NO 57
<211> LENGTH: 25
<212> TYPE: DNA
<213> ORGANISM: Artificial Sequence
<220> FEATURE:
<223> OTHER INFORMATION: PCR primer

<400> SEQUENCE: 57

```
tgaattccca tggctcgtga agcgg                                            25
```

<210> SEQ ID NO 58
<211> LENGTH: 32
<212> TYPE: DNA
<213> ORGANISM: Artificial Sequence
<220> FEATURE:
<223> OTHER INFORMATION: PCR primer

<400> SEQUENCE: 58

```
tatggatcct tgccaactac cttagtgatc tc                                    32
```

<210> SEQ ID NO 59

```
<211> LENGTH: 30
<212> TYPE: DNA
<213> ORGANISM: Nicotiana tabacum

<400> SEQUENCE: 59
tttcctgcag ttattcatga ttgagtattc                                    30

<210> SEQ ID NO 60
<211> LENGTH: 21
<212> TYPE: DNA
<213> ORGANISM: Nicotiana tabacum

<400> SEQUENCE: 60
ccagaaagaa gtatgctttg g                                             21

<210> SEQ ID NO 61
<211> LENGTH: 32
<212> TYPE: DNA
<213> ORGANISM: Artificial Sequence
<220> FEATURE:
<223> OTHER INFORMATION: PCR primer

<400> SEQUENCE: 61
ctgggtacct tattgtttgc ctccctgctg cg                                 32

<210> SEQ ID NO 62
<211> LENGTH: 24
<212> TYPE: DNA
<213> ORGANISM: Artificial Sequence
<220> FEATURE:
<223> OTHER INFORMATION: PCR primer

<400> SEQUENCE: 62
catgccatgg tccgtcctgt agaa                                          24

<210> SEQ ID NO 63
<211> LENGTH: 37
<212> TYPE: DNA
<213> ORGANISM: Artificial Sequence
<220> FEATURE:
<223> OTHER INFORMATION: PCR primer

<400> SEQUENCE: 63
ggggtaccag ttgtagggag ggatccatgc gtgaagc                            37

<210> SEQ ID NO 64
<211> LENGTH: 60
<212> TYPE: DNA
<213> ORGANISM: Artificial Sequence
<220> FEATURE:
<223> OTHER INFORMATION: PCR primer

<400> SEQUENCE: 64
ctataccatg gtttgcctcc tactactgaa tcataagcat gtagattttt tttatctgca   60

<210> SEQ ID NO 65
<211> LENGTH: 29
<212> TYPE: DNA
<213> ORGANISM: Artificial Sequence
<220> FEATURE:
<223> OTHER INFORMATION: PCR primer

<400> SEQUENCE: 65
gatcggtacc atgttctttc ctgcgttat                                     29
```

```
<210> SEQ ID NO 66
<211> LENGTH: 30
<212> TYPE: DNA
<213> ORGANISM: Artificial Sequence
<220> FEATURE:
<223> OTHER INFORMATION: PCR primer

<400> SEQUENCE: 66
gatcggtacc aaagtgtaaa gcctggggtg                                     30

<210> SEQ ID NO 67
<211> LENGTH: 24
<212> TYPE: DNA
<213> ORGANISM: Artificial Sequence
<220> FEATURE:
<223> OTHER INFORMATION: PCR primer

<400> SEQUENCE: 67
atcactagtt gtagggaggg atcc                                           24

<210> SEQ ID NO 68
<211> LENGTH: 29
<212> TYPE: DNA
<213> ORGANISM: Artificial Sequence
<220> FEATURE:
<223> OTHER INFORMATION: PCR primer

<400> SEQUENCE: 68
ctggtcgact tgctgttgca tcgaaagag                                      29

<210> SEQ ID NO 69
<211> LENGTH: 30
<212> TYPE: DNA
<213> ORGANISM: Artificial Sequence
<220> FEATURE:
<223> OTHER INFORMATION: PCR primer

<400> SEQUENCE: 69
agagcggccg caattgtgac ctctcgggag                                     30

<210> SEQ ID NO 70
<211> LENGTH: 33
<212> TYPE: DNA
<213> ORGANISM: Artificial Sequence
<220> FEATURE:
<223> OTHER INFORMATION: PCR primer

<400> SEQUENCE: 70
aaaactgcag attcgcagat ttgtcgacat caa                                 33
```

The invention claimed is:

1. A process of generating transgenic plants or plant cells transformed on their plastome and being devoid of a selection marker, comprising the following steps:
   (a) transforming plastids of a plant or plant cell with a DNA comprising:
      (i) at least one sequence of interest,
      (ii) sequences flanking said at least one sequence of interest necessary for stable integration of said at least one sequence of interest into the plastid genome, and
      (iii) a selection marker functional in a plastid and located outside of said sequences flanking said sequence(s) of interest, wherein said selection marker is not flanked by plastid DNA sequences;
   (b) allowing integration of said at least one sequence of interest into the plastome in the presence of selective pressure;
   (c) allowing loss of said selection marker sequence by releasing selective pressure; and
   (d) recovering cells and/or plants being genetically transformed on their plastomes and being devoid of said selection marker.

2. The process of claim 1, wherein said sequence of interest comprises a sequence which allows visual identification of cells containing transformed plastomes.

3. The process of claim 1, wherein the plant or plant cells to be transformed has a mutation in the plastome which causes an easily distinguishable phenotype, and whereby said process restores said easily distinguishable mutant phenotype, thereby allowing identification of transformed cells.

4. The process of claim 1, wherein, in a previous step, a photosynthesis-related gene is rendered dysfunctional or is eliminated.

5. The process of claim 4, wherein said photosynthesis related gene is selected from the group consisting of rpoA, petA, ycf3, ycf9, and rpoB.

6. The process of claim 4, wherein said DNA contains said photosynthesis-related gene functional for allowing positive selection of said transformation.

7. The process of claim 1, wherein the selection marker encodes bacterial aminoglycoside phosphotransferase A-6.

8. The process of claim 1, wherein a nucleotide sequence of the plastome is deleted.

9. The process of claim 8, wherein said flanking sequences (ii) are homologous to plastome sequences that flank said nucleotide sequence of the plastome to be deleted.

10. The process of claim 1, wherein a point mutation is created in the plastome.

11. The process of claim 1 wherein steps (c) and/or (d) comprise allowing segregation of leaf sectors each containing a particular type of plastome.

12. A transformation vector comprising a DNA comprising:
(a) at least one sequence of interest,
(b) sequences flanking said at least one sequence of interest necessary for stable integration of said at least one sequence of interest into the plastid genome, and
(c) a selection marker functional in a plastid and located outside of said sequences flanking said sequence(s) of interest, wherein said selection marker is not flanked by plastid DNA sequences.

13. The process of claim 1, wherein the DNA further comprises a nucleotide sequence conferring replication of said DNA in a plant cell.

14. The process of claim 1, wherein the DNA further comprises a nucleotide sequence conferring non-autonomous replication of said DNA in a plant cell.

* * * * *

UNITED STATES PATENT AND TRADEMARK OFFICE
CERTIFICATE OF CORRECTION

| | |
|---|---|
| PATENT NO. | : 7,371,923 B2 |
| APPLICATION NO. | : 10/482549 |
| DATED | : May 13, 2008 |
| INVENTOR(S) | : Koop et al. |

It is certified that error appears in the above-identified patent and that said Letters Patent is hereby corrected as shown below:

Column 4, Line 19: Please correct "concomittantly"
        To read -- concomitantly --

Column 7, Line 11: Please correct "replicaion,"
        To read -- replication, --

Column 7, Line 17: Please correct "the maintain of"
        To read -- the maintenance of --

Column 7, Line 20: Please correct "allow to remove said"
        To read -- allow removal of said --

Column 10, Line 56-57: Please correct "with conco-mittant insertion"
        To read -- with conco-mitant insertion --

Column 10, Line 58: Please correct "concomittant"
        To read -- concomitant --

Column 17, Line 23: Please correct "criticism on plant"
        To read -- criticism of plant --

Column 24, Line 22: Please correct "(SEQ ID:3)"
        To read -- (SEQ ID NO:3) --

Column 29, Line 9: Please correct "(SEQ ID NO:21(5'-"
        To read -- (SEQ ID NO:21)(5'- --

Column 29, Line 42: Please correct "5 leaves from 4 weeks old"
        To read -- Five leaves from 4 week old --

Column 31, Line 9: Please correct "(Hybond-N$^{+TM}$, Amersham)"
        To read -- (HYBOND-N$^{+TM}$, Amersham) --

Column 40, Line 61: Please correct "b1-3 (5'-"
        To read -- b1-3 (SEQ ID NO:44)(5'- --

Column 41, Line 15: Please correct "4 weeks old,"
        To read -- 4 week old, --

UNITED STATES PATENT AND TRADEMARK OFFICE
CERTIFICATE OF CORRECTION

PATENT NO.        : 7,371,923 B2
APPLICATION NO. : 10/482549
DATED              : May 13, 2008
INVENTOR(S)       : Koop et al.

It is certified that error appears in the above-identified patent and that said Letters Patent is hereby corrected as shown below:

Column 41, Line 63: Please correct "(Hybond-N$^+$™, Amersham"
    To read -- (HYBOND-N$^+$™, Amersham --

Column 47, Line 5: Please correct "was relegated with"
    To read -- was religated with --

Column 77, Line 50, please add to the Sequence Listing after SEQ ID NO: 70 as follows <210> 71
<211> 44
<212> DNA
<213> Artificial Sequence <220>
<223> PCR primer
<400> 71
atcactagtt gtagggaggg atccatgcct agatcacgga taaa                    44

<210> 72
<211> 43
<212> DNA
<213> Artificial Sequence

<220>
<223> PCR primer

<400> 72
tcactagttg tagggaggga tccatggttc gagagaaagt aac                     43

<210> 73
<211> 36
<212> DNA
<213> Artificial Sequence

UNITED STATES PATENT AND TRADEMARK OFFICE
CERTIFICATE OF CORRECTION

PATENT NO. : 7,371,923 B2
APPLICATION NO. : 10/482549
DATED : May 13, 2008
INVENTOR(S) : Koop et al.

It is certified that error appears in the above-identified patent and that said Letters Patent is hereby corrected as shown below:

<220>
<223> PCR primer

<400> 73
acaagagctc ataagtaata aaacgttcga ataatt                36

<210> 74
<211> 30
<212> DNA
<213> Artificial Sequence

<220>
<223> PCR primer

<400> 74
aattcctcga gtaggtcgat ggggaaaatg                30

<210> 75
<211> 28
<212> DNA
<213> Artificial Sequence

<220>
<223> PCR primer

<400> 75
ggatccatgc gtgaagcggt tatcgccg                28

<210> 76
<211> 30
<212> DNA
<213> Artificial Sequence

UNITED STATES PATENT AND TRADEMARK OFFICE
CERTIFICATE OF CORRECTION

PATENT NO.       : 7,371,923 B2
APPLICATION NO.  : 10/482549
DATED            : May 13, 2008
INVENTOR(S)      : Koop et al.

It is certified that error appears in the above-identified patent and that said Letters Patent is hereby corrected as shown below:

<220>
<223> PCR primer

<400> 76
aattcctcga gtaggtcgat ggggaaaatg                                    30

Column 80, Line 1, Claim 11: Please correct "claim 1 wherein"
                          To read -- claim 1, wherein --

Signed and Sealed this

Thirty-first Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,371,923 B2
APPLICATION NO. : 10/482549
DATED : May 13, 2008
INVENTOR(S) : Koop et al.

It is certified that error appears in the above-identified patent and that said Letters Patent is hereby corrected as shown below:

On the Title of the patent, Item (73) Assignee:
Please correct "Icon Genetics AG, Munich (DE)"
To read -- Icon Genetics GmbH, Munchen (DE) --

Signed and Sealed this

Twenty-sixth Day of May, 2009

JOHN DOLL
*Acting Director of the United States Patent and Trademark Office*